United States Patent [19]
Prasit et al.

[11] Patent Number: 5,204,344
[45] Date of Patent: Apr. 20, 1993

[54] (QUINOLIN-2-YLMETHOXY)INDOLES AS INHIBITORS OF THE BIOSYNTHESIS OF LEUKOTRIENES

[75] Inventors: Petpiboon Prasit, Kirkland; Rejean Fortin; John H. Hutchinson, both of Montreal; Michel L. Belley, St. Laurent; Serge Léger, Dollard-des-Ormeaux; John Gillard, Baie D'Urfe; Richard Frenette, Laval, all of Canada

[73] Assignee: Merck Frosst Canada, Inc., Montreal, Canada

[21] Appl. No.: 650,825

[22] Filed: Feb. 5, 1991

Related U.S. Application Data

[63] Continuation-in-part of Ser. No. 552,300, Jul. 18, 1990, abandoned, which is a continuation-in-part of Ser. No. 397,144, Aug. 22, 1989, abandoned.

[51] Int. Cl.[5] .................. A01N 43/42; C07D 215/04; C07D 401/00
[52] U.S. Cl. .......................... 514/227.8; 514/228.2; 514/235.5; 514/253; 514/312; 514/313; 514/314; 514/826; 514/914; 540/597; 544/62; 544/114; 544/121; 544/128; 546/152; 546/153; 546/155; 546/162; 546/168; 546/170; 546/171; 546/172; 546/173; 546/174; 546/175; 546/176; 546/177; 546/178; 546/180; 546/182
[58] Field of Search ............ 546/174, 173, 152, 172, 546/175, 176, 182, 153, 155, 156, 159, 162, 168, 170, 171, 177, 178, 180; 544/62, 114, 121, 128, 235, 349, 363; 540/597

[56] References Cited

U.S. PATENT DOCUMENTS

| 4,475,431 | 12/1990 | Crossley et al. | 546/174 |
| 4,629,733 | 12/1986 | Muller et al. | 514/418 |
| 4,923,881 | 5/1990 | Oku et al. | 514/311 |

FOREIGN PATENT DOCUMENTS

| 0166591A2 | 1/1986 | European Pat. Off. | |
| 0200101 | 4/1986 | European Pat. Off. | |
| 0181568A2 | 5/1986 | European Pat. Off. | |
| 027566A1 | 7/1988 | European Pat. Off. | |
| 419049 | 3/1991 | European Pat. Off. | 546/174 |
| 1228848 | 4/1971 | United Kingdom | |

OTHER PUBLICATIONS

S. Biniecki and J. Jakubowski, 98: Chem. Abst. 197936n (1983).
R. Pakula, et al., Sci. Pharm. 53: 139–46 (1985).
A. K. Sheinkman, et al., Chem. 67: 54017n (1967).

Primary Examiner—C. Warren Ivy
Assistant Examiner—Raymond Covington
Attorney, Agent, or Firm—Joseph F. DiPrima; Mark R. Daniel; David A. Muthard

[57] ABSTRACT

Compounds having the formula I:

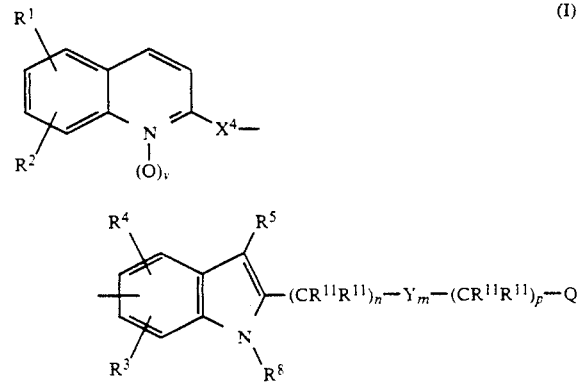

are inhibitors of leukotriene biosynthesis. These compounds are useful as anti-asthmatic, anti-allergic, anti-inflammatory, and cytoprotective agents. They are also useful in treating diarrhea, hypertension, angina, platelet aggregation, cerebral spasm, premature labor, spontaneous abortion, dysmenorrhea, and migraine.

22 Claims, No Drawings

(QUINOLIN-2-YLMETHOXY)INDOLES AS INHIBITORS OF THE BIOSYNTHESIS OF LEUKOTRIENES

RELATED APPLICATION

The present patent application is a continuation-in-part of copending application Ser. No. 552,300, filed 18 Jul. 1990, now abandoned, which is a continuation in part of copending application Ser. No. 397,144, filed 22 Aug. 1989, now abandoned.

BACKGROUND OF THE INVENTION

European Patent Applications 166,591 and 275,667 disclose a series of indole-based compounds with activity as prostaglandin antagonists and inhibitors of leukotriene biosynthesis respectively. In EP 181,568 and EP 200,101 are disclosed a series of compounds, containing two aromatic nuclei, which are described as possessing activity as lipoxygenaseinhibitors. In EP 279,263 is disclosed a series of indoles, benzofurans and benzothiophenes which are described as possessing activity as lipoxygenase inhibitors. U.S. Pat. No. 4,629,733 describes novel indolinones which are antithrombotic and inhibit both phosphodiesterase and tumor metastasis. The chemical preparation of quinolylindoles is referred to by Sheinkman, et al., Chem. Ab., Vol. 67, 54017 (1967), without mentioning any utility for such compounds. A number of N-acyl derivatives of indole3-acetic acid are described as potential anti-inflammatory agents by Biniecki, et al., Chem. Ab., Vol. 98, 197936 (1983), by Pakula, et al., Chem. Ab., Vol. 105, 190835 (1986), and in British Pat. Spec. 1,228,848.

SUMMARY OF THE INVENTION

The present invention relates to compounds having activity as leukotriene biosynthesis inhibitors, to methods for their preparation, and to methods and pharmaceutical formulations for using these compounds in mammals (especially humans).

Because of their activity as leukotriene biosynthesis inhibitors, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema. These compounds are also useful to inhibit the pathologic actions of leukotrienes on the cardiovascular and vascular systems, actions such as result in angina or endotoxin shock. The compounds of the present invention are useful in the treatment of inflammatory and allergic diseases of the eye, including allergic conjunctivitis. The compounds are also useful as cytoprotective agents and for the treatment of migraine headache.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma or stress-induced cell damage; and glycerol induced renal failure.

The compounds of this invention are inhibitors of the biosynthesis of 5-lipoxygenase metabolites of arachidonic acid, such as 5-HPETE, 5-HETE and the leukotrienes. Leukotrienes $B_4$, $C_4$, $D_4$ and $E_4$ are known to contribute to various disease conditions such as asthma, psoriasis, pain, ulcers and systemic anaphylaxis. Thus inhibition of the synthesis of such compounds will alleviate these and other leukotriene-related disease states.

DETAILED DESCRIPTION OF THE INVENTION

The present invention provides novel compounds of the formula I:

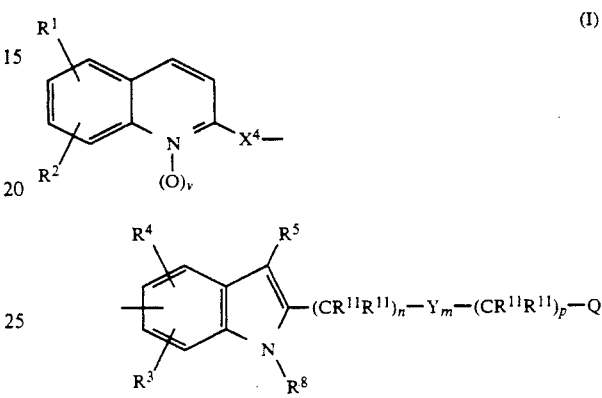

wherein:

$R^1$, $R^2$, $R^3$, $R^4$ and $R^{10}$ are independently hydrogen, halogen, lower alkyl, lower alkenyl, lower alkynyl, $-CF_3$, $-CN$, $-NO_2$, $N_3$, $-C(OH)R^{11}R^{11}$, $-CO_2R^{12}$, $-SR^{14}$, $-S(O)R^{14}$, $-S(O)_2R^{14}$, $-S(O)_2NR^{15}R^{15}$, $-OR^{15}$, $-NR^{15}R^{15}$, $-C(O)R^{16}$ or $-(CH_2)_tR^{21}$;

$R^5$ is hydrogen, $-CH_3$, $CF_3$, $-C(O)H$, $X^1-R^6$ or $X^2-R^7$;

$R^6$ and $R^9$ are independently alkyl, alkenyl, $-(CH_2)_uPh(R^{10})_2$ or $-(CH_2)_uTh(R^{10})_2$;

$R^7$ is $-CF_3$ or $R^6$;

$R^8$ is hydrogen or $X^3-R^9$;

each $R^{11}$ is independently hydrogen or lower alkyl, or two $R^{11}$'s on same carbon atom are joined to form a cycloalkyl ring of 3 to 6 carbon atoms;

$R^{12}$ is hydrogen, lower alkyl or $-CH_2R^{21}$;

$R^{13}$ is lower alkyl or $-(CH_2)_rR^{21}$;

$R^{14}$ is $-CF_3$ or $R^{13}$;

$R^{15}$ is hydrogen, $-C(O)R^{16}$, $R^{13}$, or two $R^{15}$'s on the same nitrogen may be joined to form a monocyclic heterocyclic ring of 4 to 6 atoms containing up to 2 heteroatoms chosen from O, S or N;

$R^{16}$ is hydrogen, $-CF_3$, lower alkyl, lower alkenyl, lower alkynyl or $-(CH_2)_rR^{21}$;

$R^{17}$ is $-(CH_2)_s-C(R^{18}R^{18})-(CH_2)_s-R^{19}$ or $-CH_2-C(O)NR^{15}R^{15}$;

$R^{18}$ is hydrogen or lower alkyl;

$R^{19}$ is a) a monocyclic or bicyclic heterocyclic ring containing from 3 to 9 nuclear carbon atoms and 1 or 2 nuclear hetero atoms selected from N, S or O with each ring in the heterocyclic radical being formed of 5 or 6 atoms, or b) the radical $W-R^{20}$;

$R^{20}$ is alkyl or $-C(O)R^{23}$;

$R^{21}$ is phenyl substituted with 1 or 2 $R^{22}$ groups;

$R^{22}$ is hydrogen, halogen, lower alkyl, lower alkoxy, lower alkylthio, lower alkylsulfonyl, lower alkylcarbonyl, $-CF_3$, $-CN$, $-NO_2$ or $-N_3$;

$R^{23}$ is alkyl, cycloalkyl, or monocyclic monoheterocyclic ring;

$R^{24}$ is the residual structure of a standard amino acid, or $R^{18}$ and $R^{24}$ attached to the same N can cyclize to form a proline residue;

m is 0 to 1;
n is 0 to 3;
p is 1 to 3 when m is 1;
p is 0 to 3 when m is 0;
r is 0 to 2;
s is 0 to 3;
t is 0 to 2;
u is 0 to 3;
v is 0 or 1;
W is O, S or $NR^{15}$;
$X^1$ is O, or $NR^{15}$;
$X^2$ is C(O), $CR^{11}R^{11}$, S, S(O) or $S(O)^2$;
$X^3$ is C(O), $CR^{11}R^{11}$, $S(O)_2$ or a bond;
$X^4$ is CH=CH, $CH_2-Y^1$ or $Y^1-CH^2$;
Y is $X^1$ or $X^2$;
$Y^1$ is O, S, $S(O)_2$ or $CH^2$;
Q is $-CO_2R^{12}$, $-C(O)NHS(O)_2R^{14}$, $-NHS(O)_2R^{14}$, $-S(O)_2NHR^{15}$ $-C(O)NR^{15}R^{15}$, $-CO_2R^{17}$, $-C(O)NR^{18}R^{24}$, $-CH_2OH$, or 1H- or 2H-tetrazol-5-yl;
and the pharmaceutically acceptable salts thereof.

A preferred embodiment of Formula I is that in which $X^4$ is $CH_2$-$Y^1$, $Y^1$ is O and the remaining sustituents are as defined for Formula I.

A preferred embodiment of Formula I is that in which
$R^1$, $R^2$, $R^3$ and $R^4$ are hydrogen;
$R^5$ is $X^2-R^7$ or $-OR^6$;
$R^7$ is $R^6$;
$R^8$ is $R^9$;
$R^{10}$ is hydrogen or halogen;
m is 0;
n is 1 to 3;
u is 0 in $R^6$ and 1 in $R^9$;
v is 0;
$X^2$ is $CR^{11}R^{11}$ or S;
$X^4$ is $CH_2-Y^1$;
$Y^1$ is O;
Q is $-CO_2R^{12}$; and the remaining substituents are as defined for Formula I;
and the pharmaceutically acceptable salts thereof.

Definitions

The following abbreviations have the indicated meanings:
Me = methyl
Bz = benzyl
Ph = phenyl
t-Bu = tert-butyl
i-Pr = isopropyl
c-$C_6H_{11}$ = cyclohexyl
c-Pr = cyclopropyl
c- = cyclo
Ac = acetyl
Tz = 1H- or 2H- tetrazol-5-yl
Th = 2- or 3- thienyl
c-$C_5H_9$ = cyclopentyl
1-Ad = 1-adamantyl.

Alkyl, alkenyl, and alkynyl are intended to include linear, branched, and cyclic structures and combinations thereof.

As used herein, the term "alkyl" includes "lower alkyl" and extends to cover carbon fragments having up to 20 carbon atoms. Examples of alkyl groups include octyl, nonyl, norbornyl, undecyl, dodecyl, tridecyl, tetradecyl, pentadecyl, eicosyl, 3,7-diethyl-2,2-dimethyl-4-propylnonyl, cyclododecyl, adamantyl, and the like.

As used herein, the term "lower alkyl" includes those alkyl groups of from 1 to 7 carbon atoms. Examples of lower alkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like.

The term "cycloalkyl" refers to a hydrocarbon ring having from 3 to 7 carbon atoms. Examples of cycloalkyl groups are cyclopropyl, cyclopentyl, cycloheptyl and the like.

"Lower alkenyl" groups include those alkenyl groups of 2 to 7 carbon atoms. Examples of lower alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl and the like.

"Lower alkynyl" groups include those alkynyl groups of 2 to 7 carbon atoms. Examples of lower alkynyl groups include ethynyl, propargyl, 3-methyl-1-pentynyl, 2-heptynyl and the like.

As used herein, the term "lower alkoxy" includes those alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

The term "monocyclic monoheterocyclic ring" which defines $R^{23}$ includes those monocyclic groups of 5 to 7 members containing only 1 heteroatom selected from N, S or O in the ring. Examples include tetrahydrofuran, tetrahydrothiophene, pyrrolidine, piperidine, tetrahydropyran, and the like.

The term "monocyclic or bicyclic heterocyclic ring" which defines $R^{19}$ may be 2,5-dioxo-1-pyrrolidinyl, (3-pyridinylcarbonyl) amino, 1,3-dihydro-1,3-dioxo-2H-isoindol-2-yl, 1,3-dihydro-2H-isoindol-2-yl, 2,4-imidazolinedion-1-yl, 2,6-piperidinedion-1-yl, 2-imidazolyl, 2-oxo-1,3-dioxolen-4-yl, piperidin-1-yl, morpholin-1-yl, piperazin-1-yl and the like.

The point of attachment of any heterocyclic ring may be at any free valence of the ring.

It is understood in the art that when the variable v is 1, the nitrogen of the quinolinyl N-oxide so formed is positively charged, and the oxygen is negatively charged.

The term standard amino acid is employed to include the following amino acids: alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine and valine. (See F. H. C. Crick, Symposium of the Society for Experimental Biology, 1958 (12) p. 140.)

It is understood that $R^1$ and $R^2$ may be located at any of positions 3,4,5,6,7 or 8 of the quinoline ring.

As used herein the term "lower alkylthio" includes those alkylthio groups of from 1 to 7 carbon atoms of a straight, branched or cyclic configuration. Examples of lower alkylthio groups include methylthio, propylthio, isopropylthio, cycloheptylthio, etc. By way of illustration, the propylthio group signifies $-SCH_2CH_2CH_3$.

The terms $Ph(R^{10})_2$ and $Th(R^{10})_2$ indicate a phenyl or thienyl group substituted with two $R^{10}$ substituents.

Halogen includes F, Cl, Br, and I.

It is intended that the definitions of any substituent (e.g., $R^1$, $R^2$, $R^{15}$, $Ph(R^{10})_2$, etc.) in a particular molecule be independent of its definitions elsewhere in the molecule. Thus, $-NR^{15}R^{15}$ represents $-NHH$, $-NHCH_3$, $-NHC_6H_5$, etc.

The monocyclic heterocyclic rings formed when two $R^{15}$ groups join through N include pyrrolidine, piperidine, morpholine, thiamorpholine, piperazine, and N-methylpiperazine.

The prodrug esters of Q (i.e., when $Q=CO_2R^{17}$) are intended to include the esters such as are described by Saari et al., J. Med. Chem., 21, No. 8, 746-753 (1978), Sakamoto et al, Chem. Pharm. Bull., 32, No. 6, 2241-2248 (1984) and Bundgaard et al., J. Med. Chem., 30, No. 3, 451-454 (1987).

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N¹-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

It will be understood that in the discussion of methods of treatment which follows, references to the compounds of Formula I are meant to also include the pharmaceutically acceptable salts.

The ability of the compounds of Formula I to inhibit biosynthesis of the leukotrienes makes them useful for inhibiting the symptoms induced by the leukotrienes in a human subject. This inhibition of the mammalian biosynthesis of leukotrienes indicates that the compounds and pharmaceutical compositions thereof are useful to treat, prevent or ameliorate in mammals and especially in humans: 1) pulmonary conditions including diseases such as asthma, 2) allergies and allergic reactions such as allergic rhinitis, contact dermatitis, allergic conjunctivitis, and the like, 3) inflammation such as arthritis or inflammatory bowel disease, 4) pain, 5) skin conditions such as psoriasis and the like, 6) cardiovascular conditions such as angina, endotoxin shock, and the like and 7) renal insufficiency arising from ischaemia induced by immunological or chemical (cyclosporin) etiology, and that the compounds are cytoprotective agents.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (Preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001-1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug (NSAID) that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of Compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |
| Tablet | mg/tablet |
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |
| Capsule | mg/capsule |
| Compound of Formula I | 25 |
| Lactose Powder | 573.5 |
| Magnesium Stearate | 1.5 |
| | 600 |

| Aerosol | Per canister |
| --- | --- |
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH₃)COOH or —CH₂CH₂COOH group (which optionally can be in the form of a pharmaceutically acceptable salt group, e.g., —CH(CH₃)COO⁻Na⁺ or —CH₂CH₂COO⁻Na⁺), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g. —CH₂COO⁻Na⁺), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

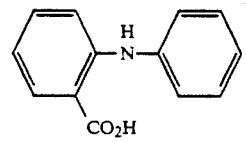

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

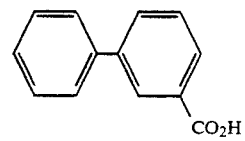

which can bear a variety of substituents and in which the free —COOH group can be in the form of a pharmaceutically acceptable salt group, e.g., —COO⁻Na⁺.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non narcotic analgesics/non-steroidal anti-inflammatory drugs which have the general formula:

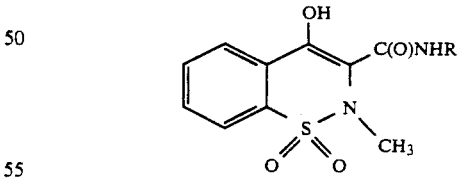

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDs, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ON03144, PR823, PV102, PV108, R830, RS2131, SCR152, SH440, SIR133, SPAS510, SQ27239, ST281, SY6001, TA60, TAI 901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDS are acetyl salicylic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$ or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. No. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in Nature, Vol. 316, pages 126–131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Compounds of the present invention can be prepared according to the following methods. Temperatures are in degree Celsius.

The starting methoxy phenylhydrazines II are either commercially available or are described in the chemical literature as are the acetamidophenols XXVI. The benzyl phenylhydrazine starting materials III are prepared as described in EP 166,591 (17102 IA) and the ketones IV and XXXI are prepared as described in EP 166,591 and EP 275,667 (17496 IA). The 2-(halomethyl)quinolines VII are available from literature methods described in "Quinolines" Parts I and II, G. Jones (ED.), John Wiley & Sons, Toronto, 1977 and 1982. The preparation of VII by halogenation of the corresponding 2-methylquinolines is also described in the Jones' volumes. The benzyl halides, $(R^{10})_2$ PhCH$_2$-Hal, are readily prepared and many such compounds are described in the prior art, such as U.S. Pat. No. 4,808,608 (17323 IB). Hal in VII and $(R^{10})_2$ PhCH$_2$-Hal represents Cl, Br or I.

Many syntheses of indoles are well-known in the chemical literature: see for example, "Heterocyclic compounds" Volume 25, Parts I, II, III, W. J. Houlihan (Ed.), Interscience, J. Wiley & Sons, N.Y., 1979, and "The Chemistry of Indoles" by R. J. Sundberg, Academic Press, N.Y., 1970. One of the most common syntheses is known as the Fischer Indole Synthesis, and is abbreviated in the following methods as "Fischer".

The —CO$_2$H and —CO$_2$R$^{12}$ groups in the intermediates and final products in the various methods can be transformed to other representatives of Q such as —CONHS(O)$_2$R$^{14}$, —NHS(O)$_2$R$^{14}$, —CONR$^{15}$R$^{15}$, —CH$_2$OH or tetrazol-5-yl by the methodology described in U.S. Pat. No. 4,808,608 (17323IB). The preparation of the pro-drug forms (Q is —CO$_2$R$^{17}$) from the acids may be effected by the methodology of EP 104,885 (16830 IA).

It will be apparent to one skilled in the art that the various functional groups ($R^1$, $R^2$, Y, Q, etc.) must be chosen so as to be compatible with the chemistry being carried out. Such compatibility can often be achieved by protecting groups, or by specific variations in the sequence of the reactions.

When $R^5$ is S-R$^7$, the corresponding sulfoxides and sulfones can be prepared by oxidation of the sulfides with one or two equivalents of an oxidizing agent such as m-chloroperbenzoic acid or monoperoxyphthalic acid or oxone (Trost, J. Org. Chem., 1988, pg. 532).

Many of the following methods involve a basic hydrolysis of an ester function to obtain the corresponding carboxylic acid. In all cases, the free acid is obtained by acidification of the reaction mixture with a suitable acid such as hydrochloric, sulfuric, acetic, trifluoroacetic acid, etc.

Compounds VIII, XI, XV, XIX, XXXVI, XL, XLIV, L, LI, LVIII, LIX and their precursor esters are all examples of the Formula I compounds of the present invention.

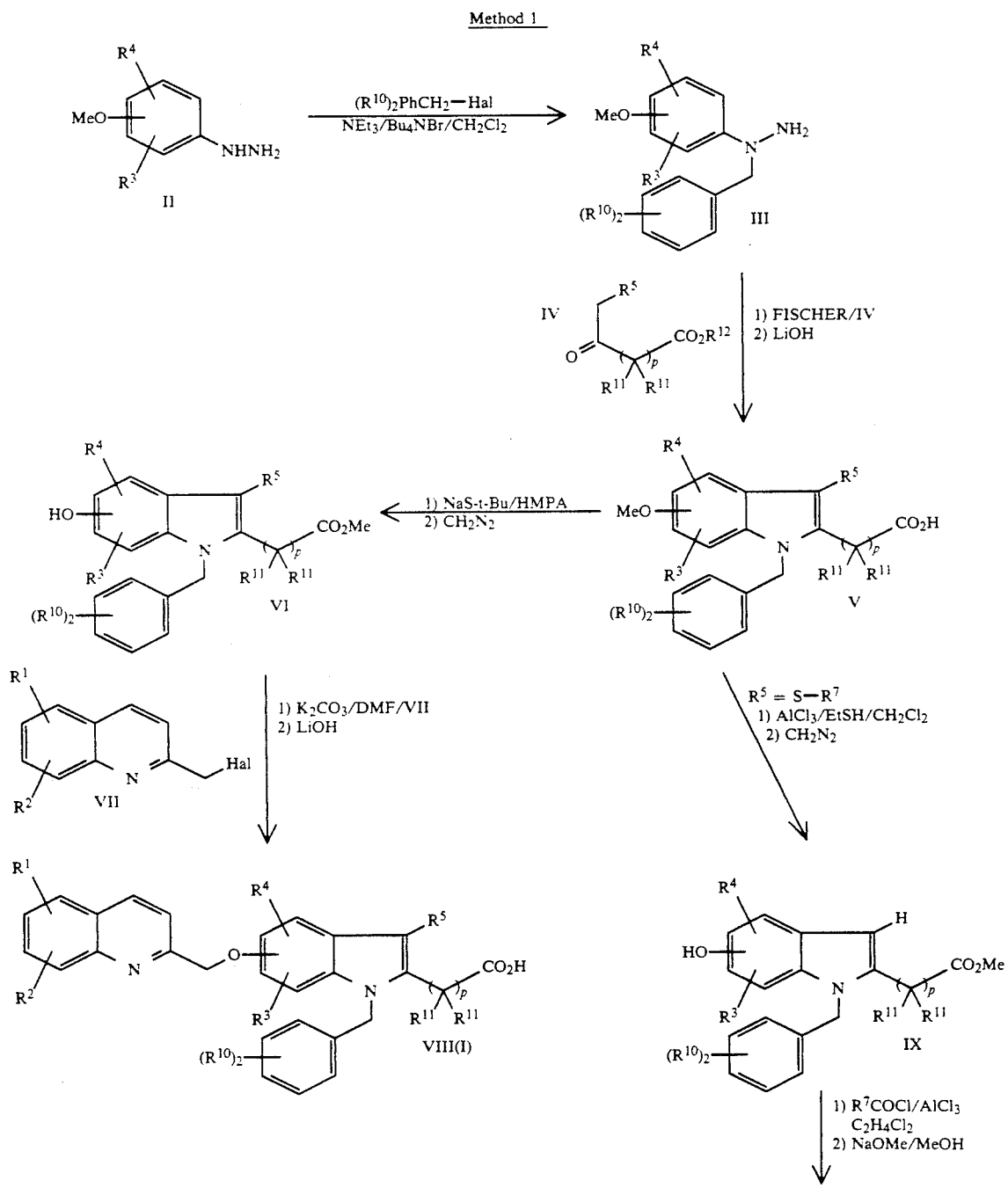

-continued

Method 1

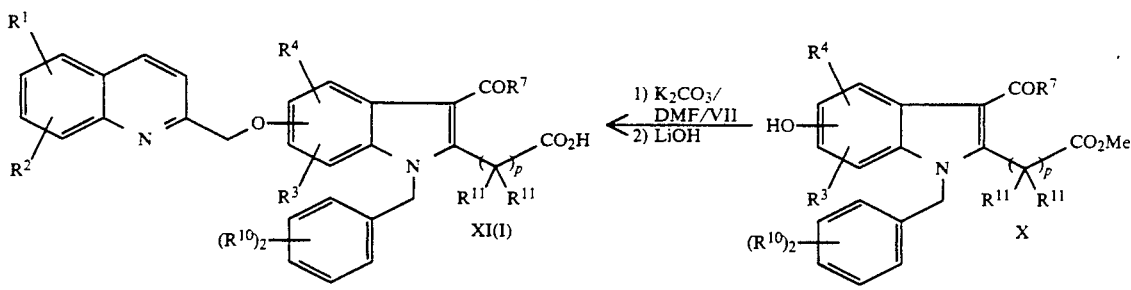

Method 1

Intermediate V is prepared by a Fischer reaction between benzylphenylhydrazine III and ketone IV, followed by hydrolysis with an aqueous solution of an alkali hydroxide or other suitable hydroxide in mixture with a suitable water miscible organic solvent such as tetrahydrofuran (THF) or methanol (MeOH). The methoxy acid V is demethylated by heating with an alkali salt of an aliphatic thiol in a suitable solvent such as hexamethylphosphorictriamide (HMPA) or N-methylpyrrolidone (NMP). The reaction mixture is acidified and the crude acid so obtained is converted to the methyl ester VI by treatment with diazomethane. The phenol VI is coupled to the 2-halomethylquinoline VII, by stirring with a base (preferably an alkali hydride or carbonate) in a suitable solvent such as dimethyl formamide (DMF), NMP, acetone or the like. The resulting ester is hydrolysed by base to yield VIII, a compound of the present invention.

When intermediate V contains a sulfide group attached to position 3, treatment with a Lewis acid, such as $AlCl_3$, and an aliphatic thiol, simultaneously effects demethylation and removes the sulfide group. Suitable solvents for this reaction are methylene chloride, 1,2-dichloroethane, etc. The resulting acid is then converted to the methyl ester IX with diazomethane. A Friedel-Crafts reaction between IX and an acid chloride, $R^7COCl$, simultaneously introduces the acyl substituent into the 3-position of the indole ring and onto the phenolic hydroxyl group. The acyl group is removed from the phenol by treatment with sodium methoxide in MeOH to yield acylphenol X. Phenol X is coupled with VII as described for the coupling of VI and VII above. In these coupling reactions, it is at times advantageous to add a catalyst such as potassium iodide or tetraethylammonium bromide, especially when Hal is chlorine. A final hydrolysis yields compound XI.

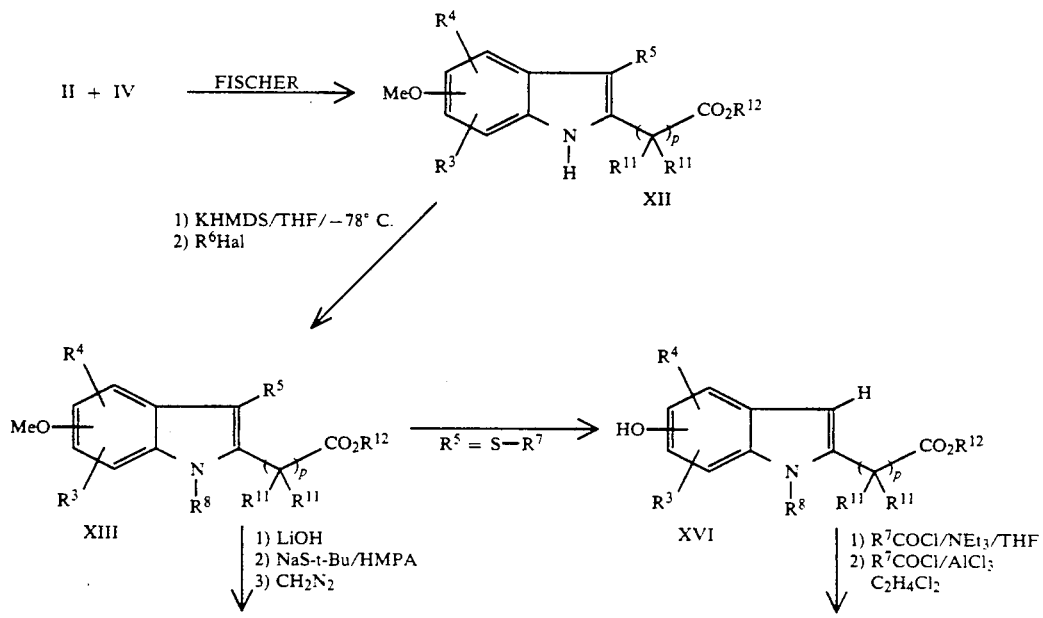

-continued
METHOD 2

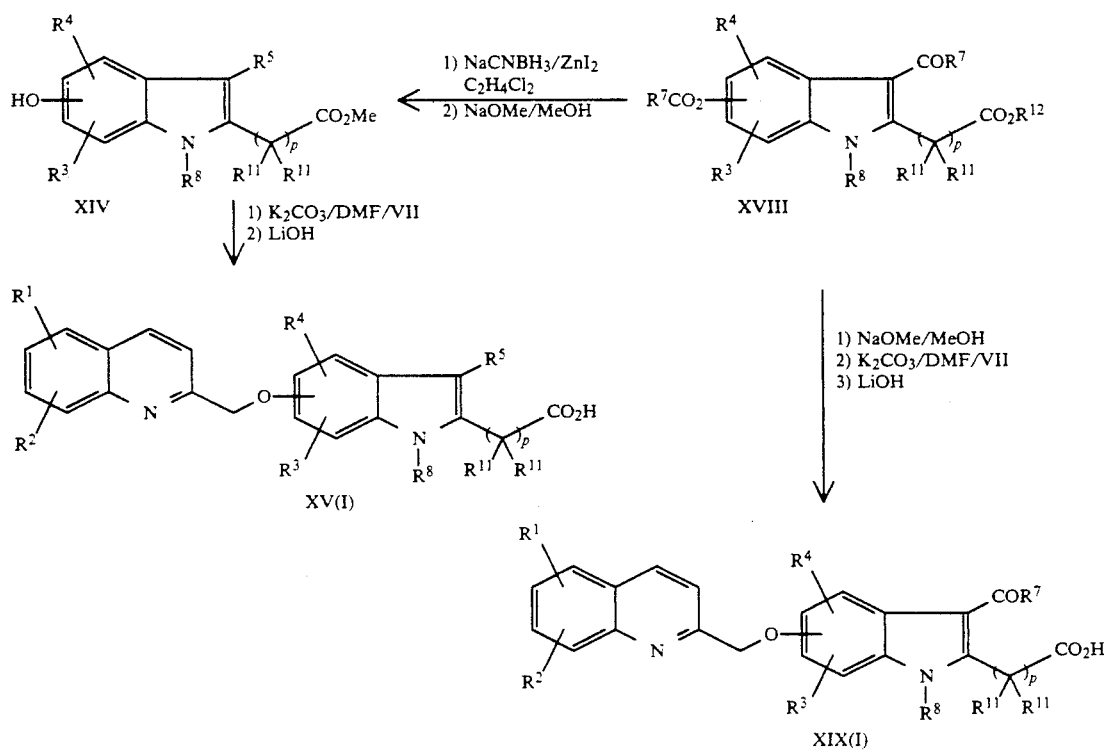

Method 2

Intermediate XII is prepared by a Fischer reaction between methoxyphenyl hydrazine II and ketone IV, followed by alkylation of the indole nitrogen, after deprotonation using potassium hexamethyldisilazane in an ether solvent such as tetrahydrofuran (THF), with an alkyl or aralkyl halide.

The methoxy group in XIII is removed using the conditions of Method 1. The corresponding phenol XIV is now coupled with the 2-halomethylquinoline VII by stirring with a base (preferably an alkali hydride or carbonate) in a suitable solvent such as DMF, NMP or the like. The resulting ester is hydrolysed using base to yield XV a compound of the present invention.

When intermediate XIII contains a sulfide at position 3, treatment with a Lewis acid such as AlCl$_3$ and an aliphatic thiol simultaneously effects demethylation and removes the sulfide group. Suitable solvents for this reaction are dichloromethane or dichloroethane. In a variation of Method 1, the phenolic hydroxyl in XVI is first acylated with the reagent R$^7$COCl (XVII) in the presence of a weak base such as triethylamine. A Friedel-Crafts reaction is then carried out on the O-acylated intermediate, with an additional mole of XVII and AlCl$_3$, to yield the intermediate XVIII. Acyl ester XVIII may then be reduced to a 3-alkyl indole XIV using sodium cyanoborohydride in dichloroethane using a zinc iodide catalyst.

Acyl ester XVIII is cleaved to the indole phenol by hydrolysis with sodium methoxide in methanol and is coupled to 2-halomethyl quinoline VII using a base such as an alkali hydride or carbonate in a solvent such as DMF or NMP. Hydrolysis of the resulting compound using base yields the compound of the present invention XIX.

METHOD 3

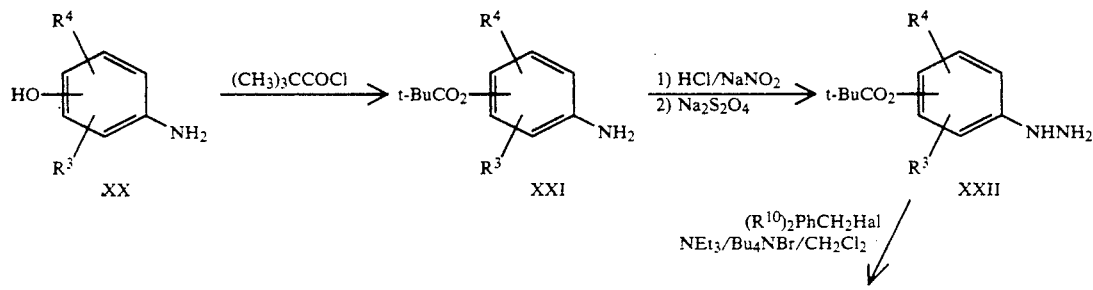

-continued
METHOD 3

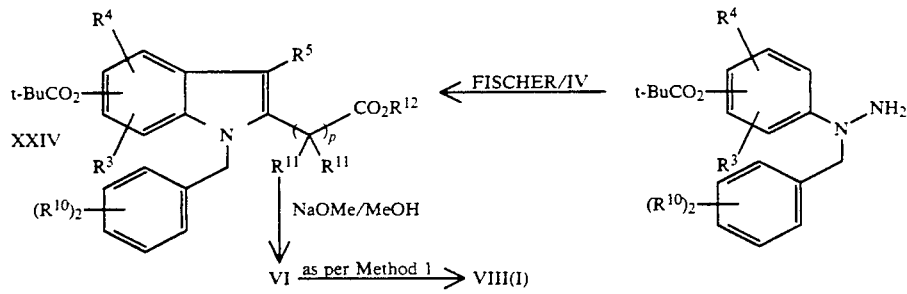

Method 3

A suitably substituted aminophenol XX is protected on oxygen by the use of pivaloyl chloride dissolved in $CH_2Cl_2$ using triethyl amine as base. The pivaloate ester XXI is then diazotized using hydrochloric acid and sodium nitrite in an aqueous solvent and the transient diazonium species reduced in situ to the hydrazine XXII using sodium hydrosulfite in water. Benzylation of the hydrazine is effected as described in Method 1.

The O-pivaloyl-N-benzylhydrazine XXIII is subjected to a Fischer indolization using the appropriate ketone IV to produce the indole XXIV. Cleavage of the O-pivaloyl group using sodium methoxide in methanol transforms the product into the phenolic indole VI which is converted to the products of this invention as described in Method 1.

XXII + IV $\xrightarrow{\text{FISCHER}}$ Method 4

-continued
Method 4

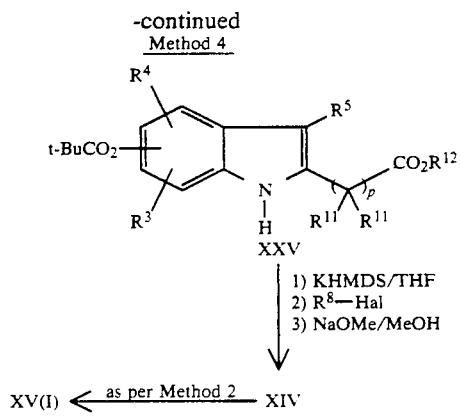

Method 4

The pivaloyloxyphenylhydrazine XXII is used directly in the Fischer indolization using ketone IV. N-Alkylation of the indole XXV, as described in Method 2, followed by removal of the pivaloyl group as described, yields the phenolic indole XIV which is converted as described in Method 2 to the products of this invention.

Method 5

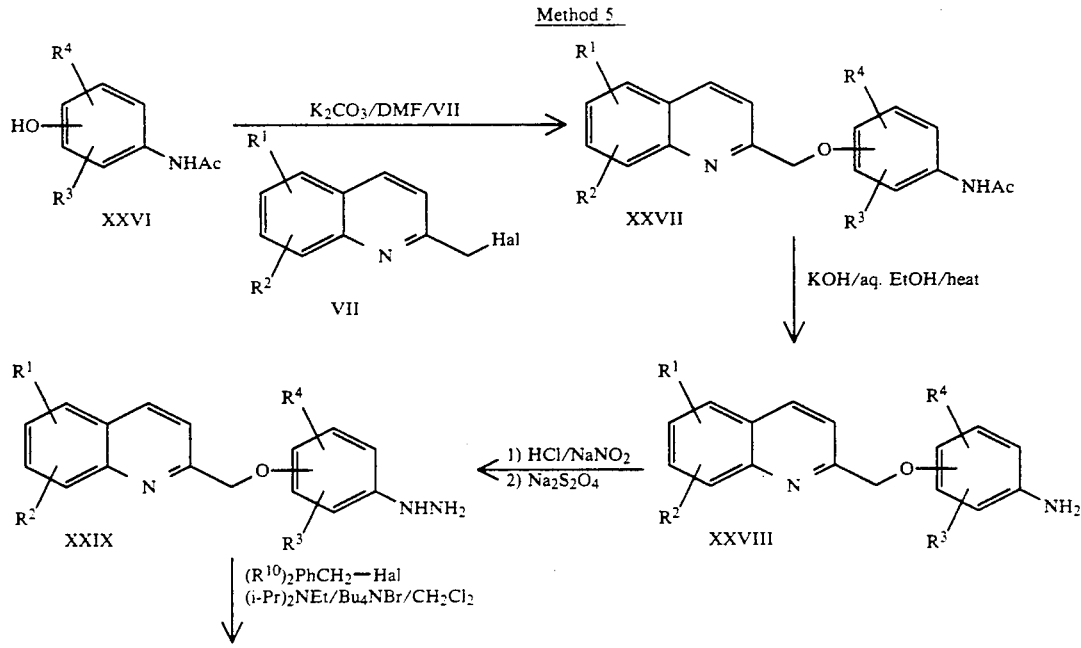

-continued  
Method 5

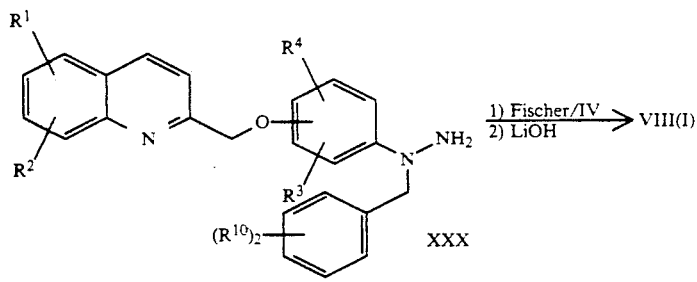

Method 5

A suitable N-acetylated aminophenol XXVI is reacted with VII using an alkali hydride or carbonate, such as potassium carbonate as a base in a polar solvent like DMF or NMP. The quinolinylmethoxy acetanilide XXVII is then de-acetylated using standard basic conditions, preferably using alcoholic potassium hydroxide under reflux to produce the quinolinylmethoxy aniline derivative XXVIII. Conversion of the quinolinylmethoxy aniline derivative to the hydrazine analogue XXIX is effected through reduction of the intermediate diazonium salt using sodium hydrosulfite in an aqueous medium.

The hydrazine XXIX is then N-benzylated using a benzyl halide in an organic solvent such as methylene chloride containing an amine base such as diisopropylethylamine and preferably tetra-n-butylammonium bromide as catalyst.

The hydrazine XXX is then processed using a Fischer indolization with ketone IV according to Methods 1, 2, 3 and 4 to produce compounds of the present invention.

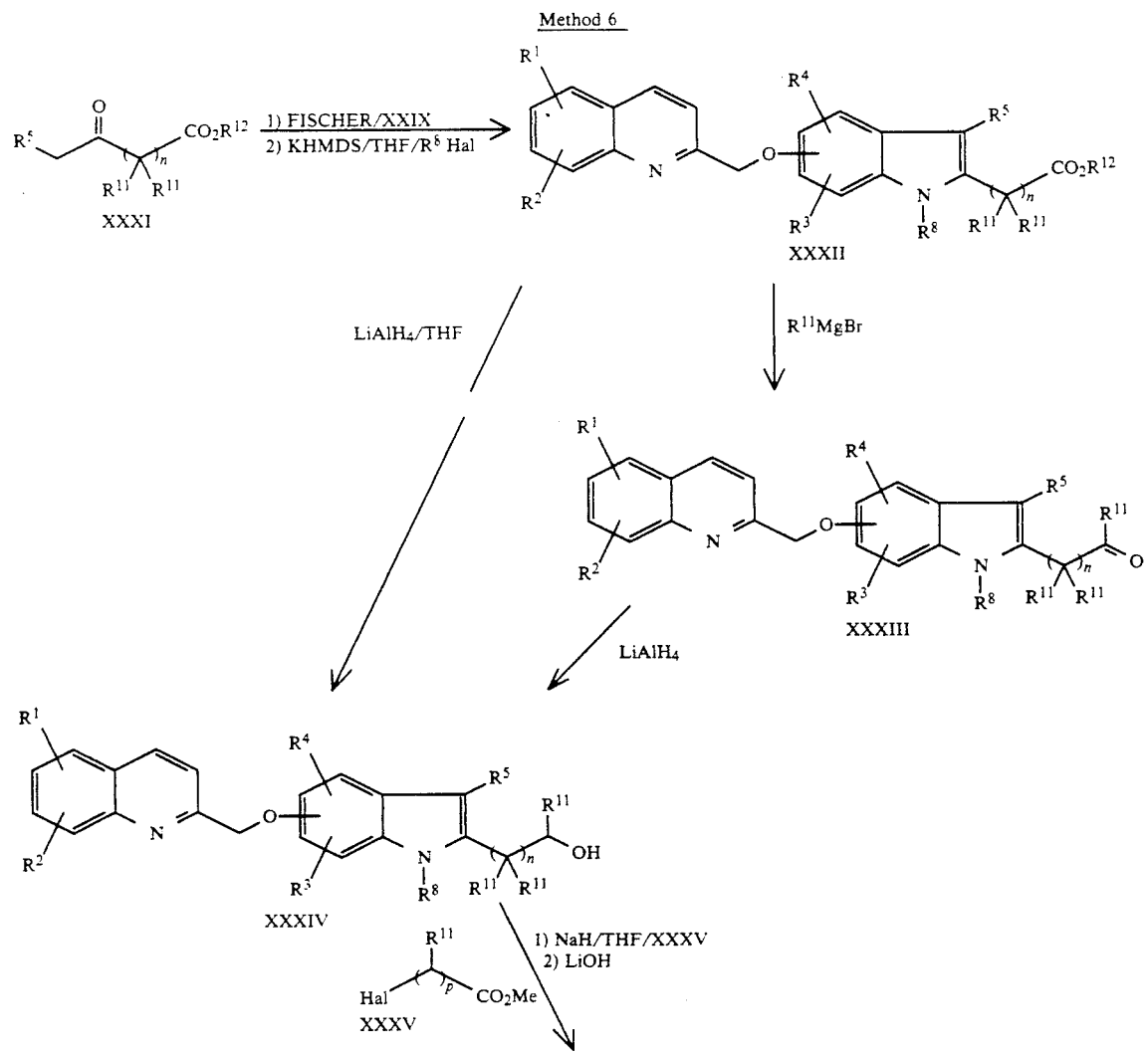

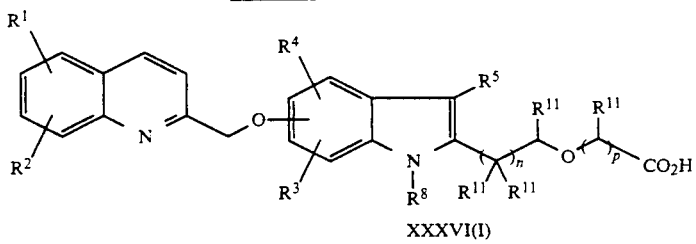

XXXVI(I)

Method 6

Hydrazine XXIX may also be transformed directly to unsubstituted indoles by a Fischer reaction with various ketones like XXXI. N-Alkylation of the indoles is effected using the conditions described in Method 2 to produce quinolinylmethoxyindole alkanoate esters XXXII. Such esters are transformed to ketones or carbinols via Grignard conditions using alkyl magnesium halides in ether solvents like diethyl ether or through the use of lithium aluminum hydride in ether solvents like THF. The carbinols XXXIV so produced may be further transformed into ester compounds of the present invention by reacting with α-halo esters XXXV using sodium hydride as base in a suitable solvent like THF. Subsequent hydrolysis of the esters using Method 1 leads to acid compounds of the present invention.

1 for the conversion of V to IX. Compound XXXVIII is then obtained by reaction of XXXVII with VII in the presence of a base in a suitable solvent, as described for the conversion of VI to VIII in Method 1. The introduction of $R^5$ in XXXIX is conveniently effected by an electrophilic reaction between XXXVIII and $R^5$-Cl ($R^5$ not $=X^1$-$R^6$). Such reactions are frequently catalysed by Lewis acids or proton acids such as $AlCl_3$, $SnCl_4$, $TiCl_4$, $BBr_3$, HCl, HBr and the like. They may be carried out in a variety of solvents, with a preference for non-protonic solvents such as dichloromethane, 1,2-dichloroethane, nitromethane, chlorobenzene and the like. It will be obvious to one skilled in the art, that the chlorine in $R^5$-Cl, in this and the other Methods, may often be replaced by another halogen or by a hydroxyl group, or $R^5$-Cl may be replaced by an acid anhydride $(R^7CO)_2O$. An alternative synthesis of XXXIX is to effect a Fischer

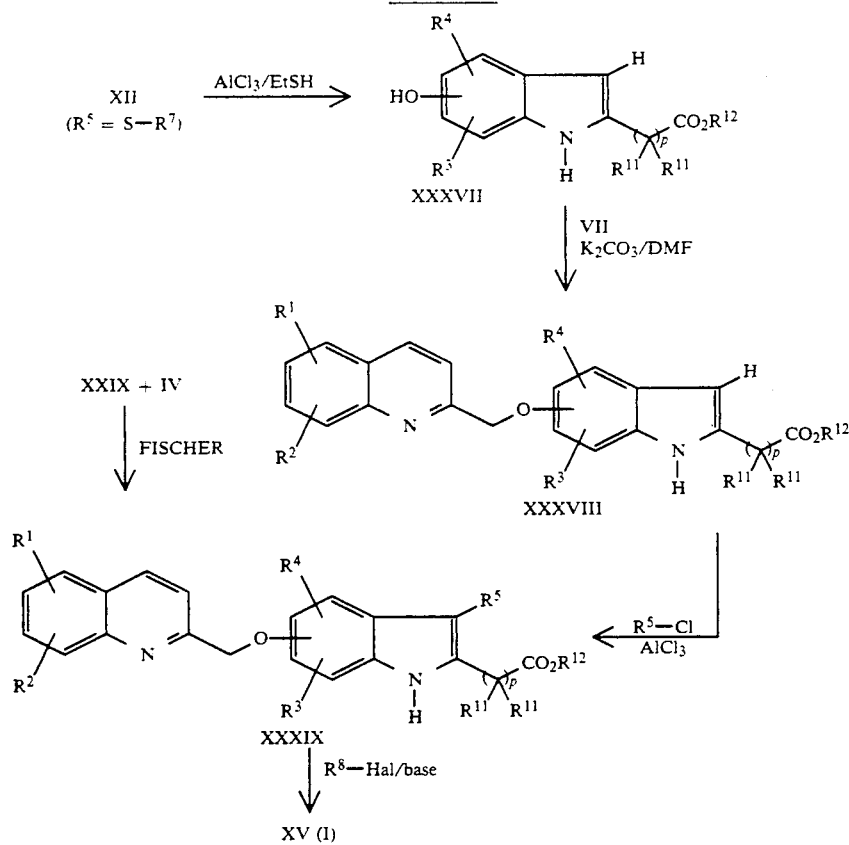

Method 7

Phenol XXXVII is obtained by treatment of XII ($R^5$=S-$R^7$) with a Lewis acid and a thiol, as in Method reaction between compounds IV and XXIX. Introduction of $R^8$ into XXXIX, is accomplished by alkylation with R[8]-Hal and a base as described previously for Methods 2, 4 and 6. Finally, hydrolysis of the ester will yield XV. Alternatively, the ester group in XXXIX can be hydrolysed, and the corresponding free acid (R[12]=H) alkylated on the indole nitrogen with R[8]-Hal and an aqueous base, such as NaOH, and a phase-transfer catalyst, such as methyltrioctylammonium chloride. Alkylation of the acid corresponding to XXXIX (R[12]=H) can also be effected using a strong base such as sodium hydride in a solvent such as DMF. This latter procedure usually gives the ester of XV in which the carboxyl group has also been alkylated. The free acid XV can be obtained by standard hydrolysis procedures. If R[8] in XV or the ester precursor of XV is alkenyl, it can be reduced to alkyl using hydrogen gas, and a Pt or Pd catalyst in a suitable solvent, at atmospheric pressure.

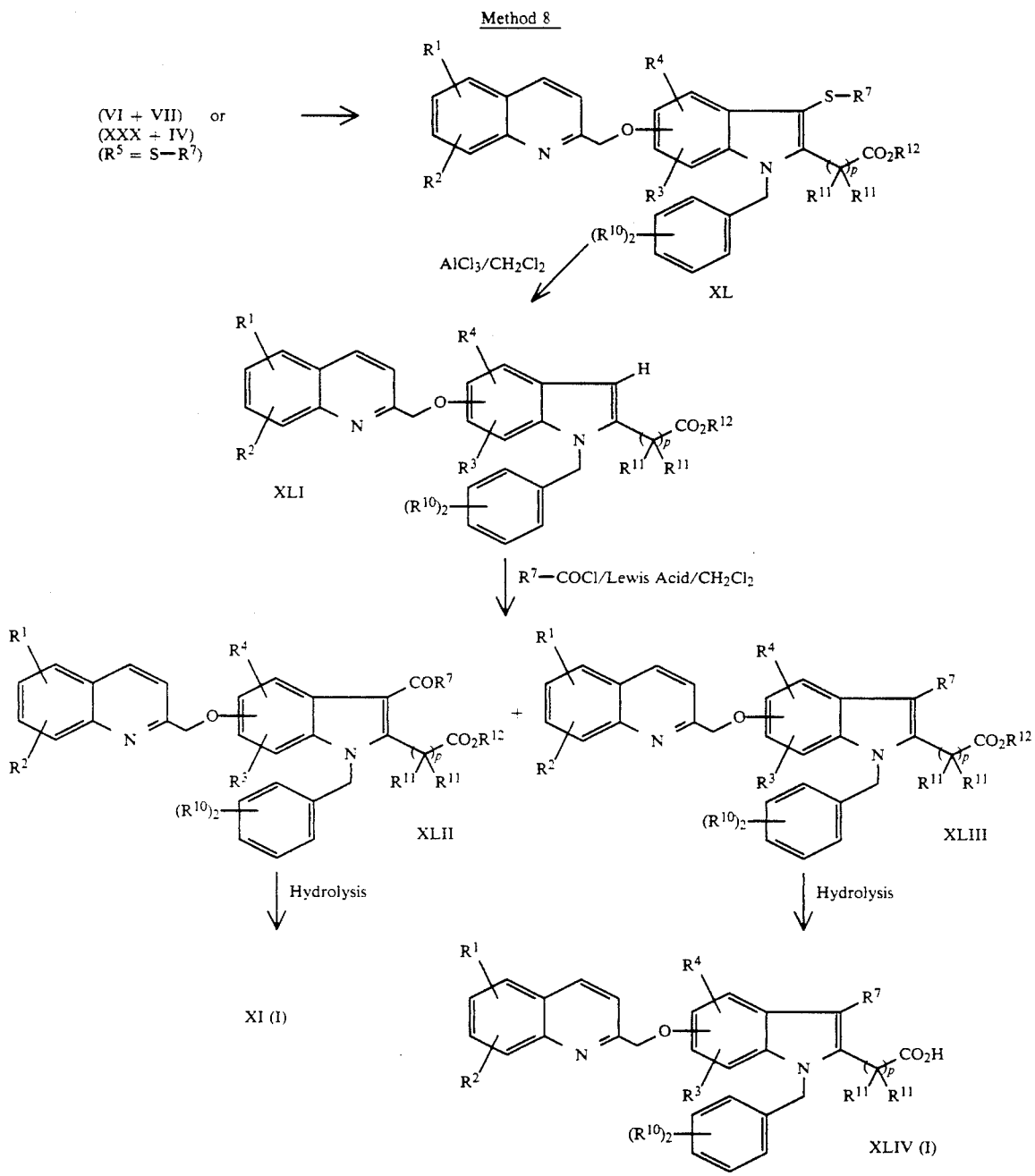

Method 8

Method 8

Compound XL may be prepared either by the coupling of VI to VII (Method 1) or by a Fischer reaction between IV and XXX (Method 5). Compound XL may be desulfurized by treatment with a Lewis acid such as AlCl₃, or by reduction with Raney nickel, to give compound XLI. A Friedel-Crafts reaction on XLI with the reagent R[7]COCl and a Lewis acid catalyst such as AlCl₃ yields the 3-acyl derivative XLII, hydrolysis of which yields XI. In the Friedel-Crafts reaction, carbon monoxide may be lost and compound XLIII is formed; hydrolysis under standard conditions then yields XLIV. The formation of XLIII occurs when the cation R[7]+ is especially stable and when the reagents R⁷COCl and the Lewis acid are mixed before adding XLI. If the Lewis acid is added last, the main product is usually the acylated compound XLII. If a milder Lewis acid such as TiCl₄ is used, the main product is also XLII.

It will be obvious to one skilled in the art that the reagent R⁷COCl can often be replaced by R⁷CO-Hal (Hal=F, Br or I) or (R⁷CO)₂O.

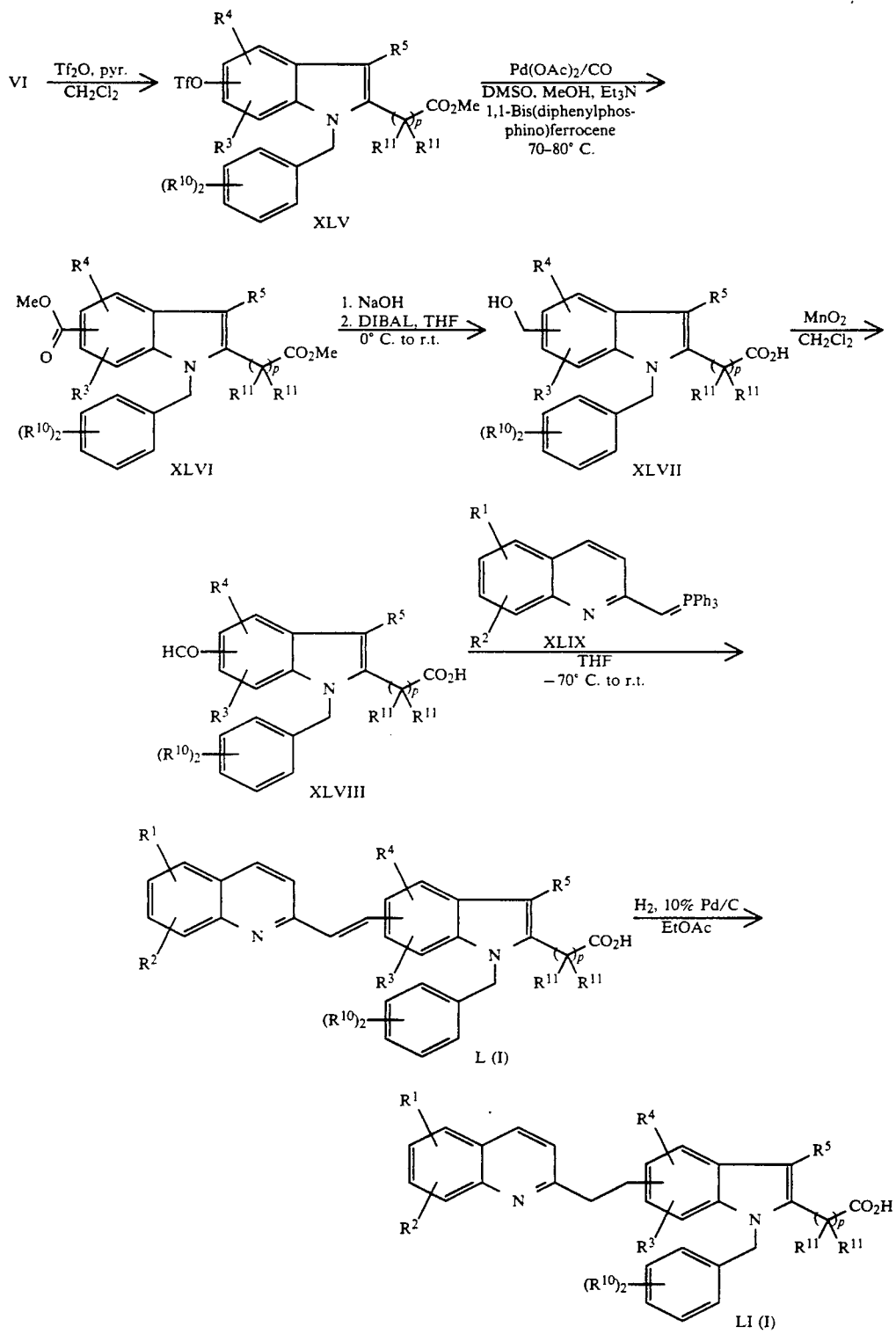

Method 9

Indole phenol VI which may be prepared according to Methods 1 or 2 is transformed to a phenol triflate XLV by treatment with trifluoromethyl sulfonic anhydride (Tf$_2$O) in a solvent like pyridine in dichloromethane. The phenol triflate may be carboxymethylated to a compound like XLVI under palladium acetate catalysis in an atmosphere of carbon monoxide, a phosphine ligand like 1,1-bis(diphenylphosphinoferrocene) enhances this reaction. Reduction of the carboxymethylated indole may be effected with a variety of hydride reducing agents. Conveniently diisobutylaluminumhydride is used in THF on the hydrolysed ester. The reduced carbinol product XLVII is conveniently oxidized to a formylated derivative XLVIII with manganese dioxide in methylene chloride as a typical solvent. Aldehyde XLVIII can then be homologated under carbanion conditions, typically using Wittig reagent XLIX (see U.S. Pat. No. 4,851,409) as shown in the method, under anydrous conditions in an etherial solvent like THF. The temperature of this reaction is typically from $-70°$ C. to room temperature. Indole styryl quinoline analogues (trans) L are thus formed. Further transformation of the styryl system may be effected by catalytic reduction using H$_2$ and Pd/C in an organic solvent like ethyl acetate to yield the saturated compound LI.

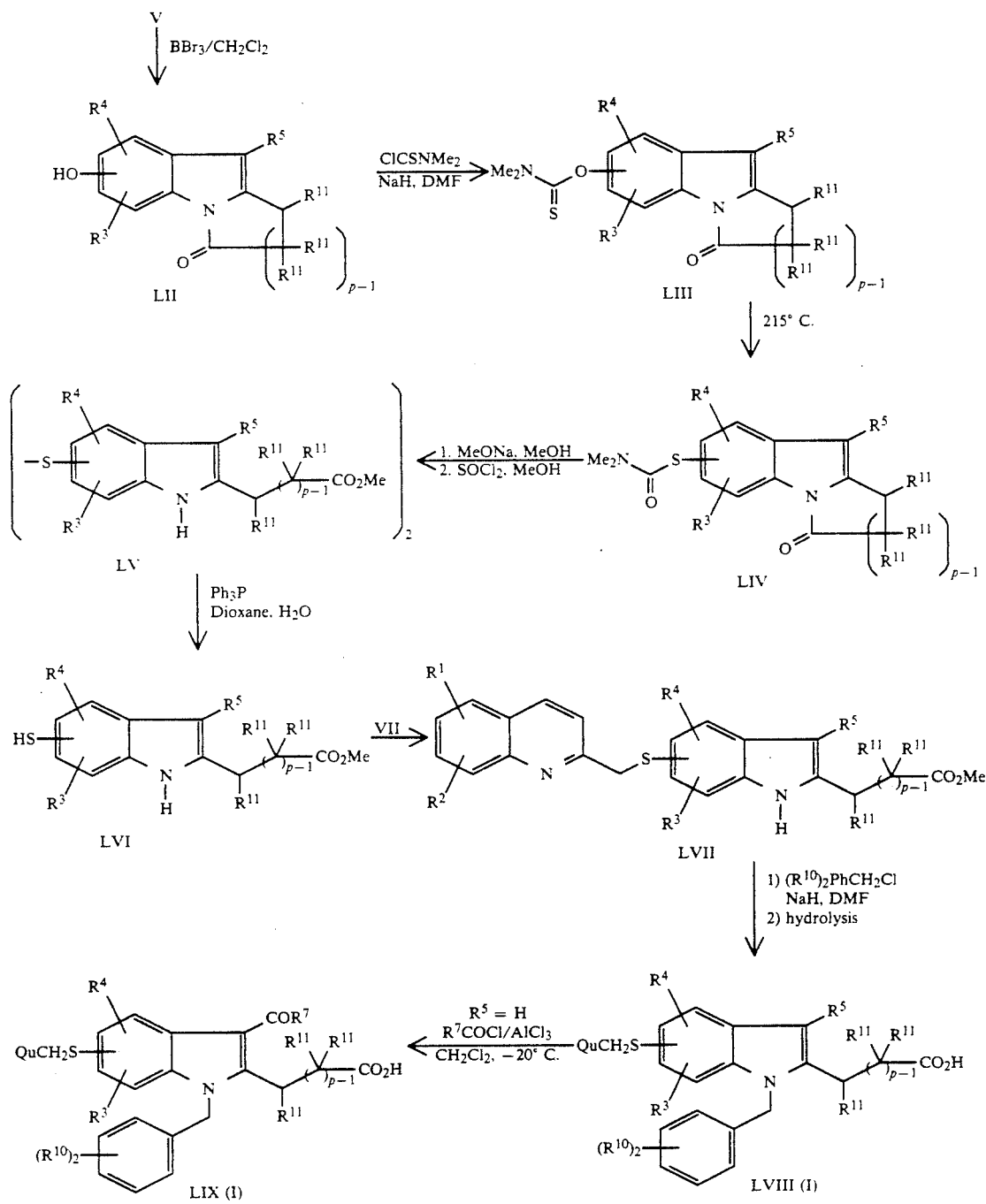

Method 10

-continued
Method 10

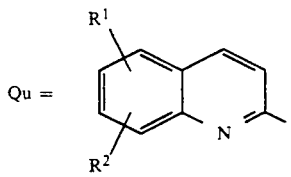

Method 10

Indole thio analogues of I such as LIX are conveniently prepared by the sequence shown in Method 10. The treatment of compound V with BBr$_3$ in a chlorinated solvent such as CH$_2$Cl$_2$ cleaves both the methyl ether and the indole N-benzyl group and cyclizes the product to an indole lactam LII. Derivatization of this compound as an N,N-dimethylthiocarbamoyl indole LIII followed by thermal rearrangement at >200° C. gives rise to an N,N-dimethylcarbamoylthioindole derivative LIV. Depending on the duration of heating, dethiolation (R$^5$=-S-t-Bu→R$^5$=H) may also take place. The hydrolysis of LIV may be effected using strong base, typically sodium methoxide in methanol is used. Spontaneous formation of disulfide LV may occur in this reaction. The reduction of LV can be achieved using triphenylphosphine in aqeuous dioxane to produce LVI. Coupling of LVI to an appropriately substituted quinoline derivative VII takes place under organic base catalysis; typically trimethylamine, in an organic solvent such as methylene chloride, is used. Transformation of indole LVII to an N-benzylated derivative LIX is achieved under standard conditions described in Method 2 or by benzylation with an appropriate benzyl halide using a base such as sodium hydride in a non-protic solvent such as dimethylformamide.

—CN group can serve as the starting material to prepare the amide and carboxylic acid functional groups. The reactions depicted in Method 11 as well as methods for synthesis of the sulfonamide group (—S(O)$_2$NHR$^{15}$) are well-know in the art. See, for instance the following text books:

1. J. March, *Advanced Organic Chemistry*, 3rd ed., J. Wiley and Sons, Toronto, 1985.
2. S. R. Sandler and W. Karo, *Organic Functional Group Preparations*, I & II, Academic Press, Toronto, 1983 and 1986.

Method 12

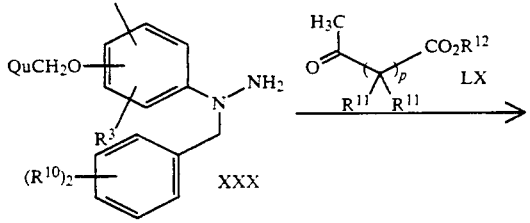

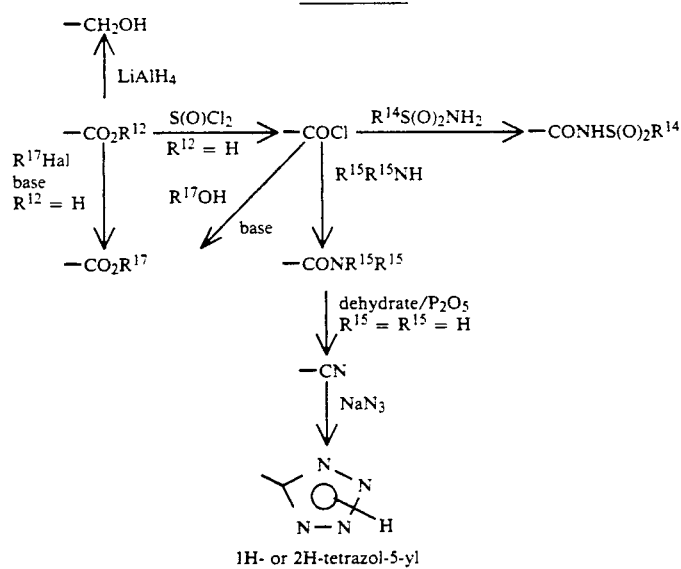

1H- or 2H-tetrazol-5-yl

Method 11

The preparation of the various definitions of Q is outline in Method 11, starting from the readily available carboxylic acid derivative —CO$_2$R$^{12}$. It will be obvious to one skilled in the art that many of the reactions indicated are reversible. Thus, by way of illustration, the

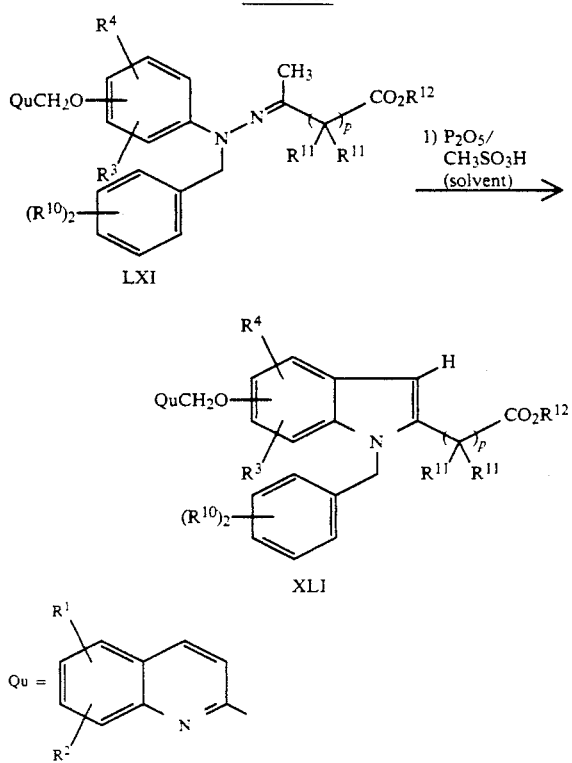

Method 12

3-Unsubstituted indole analog XLI, described in Method 8, may be more conveniently prepared by the process illustrated in Method 12 and described in greater detail in copending application Ser. No. 642,778, filed Jan. 16, 1991 now U.S. Pat. No. 5,157,102. Thus, the suitably substituted hydrazine XXX is reacted with the suitably substituted methyl ketone LX to provide the hydrazone LXI. The hydrazone LXI is treated with a combination of phosphorous pentoxide and methane sulfonic acid, optionally in the presence of a suitable co-solvent, such as sulfolane, dichloromethane and the like, to provide the 3-unsubstituted indole XLI.

Representative Compounds

Table I, and Table II and Table III illustrate compounds having the formulae Ia, Ib and Ie respectively representative of the present invention. "Attach point" is the position on the indole nucleus where the quinolylmethoxy moiety is attached.

TABLE I

Ia

| Ex No. | $R^1,R^2$ | $R^3$ | ATTACH POINT | $R^8$ | $R^5$ | $Y-(CR^{11}R^{11})_p$ |
|---|---|---|---|---|---|---|
| 1 | H,H | H | 5 | $-CH_2Ph-4-Cl$ | $-S-t-Bu$ | $C(Me)_2$ |
| 2 | H,H | H | 5 | $-CH_2Ph-4-Cl$ | Me | $C(Me)_2$ |
| 3 | H,H | H | 5 | $-CH_2Ph-4-S-t-Bu$ | $-S-t-Bu$ | $C(Me)_2$ |
| 4 | H,H | H | 5 | $-CH_2Ph-4-Cl$ | $-SPh$ | $C(Me)_2$ |
| 6 | H,H | H | 5 | $-CH_2Ph-4-Cl$ | $-S(O)_2Ph$ | $C(Me)_2$ |
| 7 | H,H | H | 5 | $-CH_2Ph-4-Cl$ | $-S(O)Ph$ | $C(Me)_2$ |
| 8 | H,H | H | 5 | $-CH_2Ph-4-Cl$ | H | $C(Me)_2$ |
| 9 | H,H | H | 5 | $-CH_2Ph-4-Cl$ | $-C(O)Ph$ | $C(Me)_2$ |
| 10 | H,H | H | 5 | $-CH_2Ph-4-Cl$ | $-CH_2Ph$ | $C(Me)_2$ |
| 11 | H,H | H | 5 | $-CH_2Ph-4-Cl$ | $-C(O)CH_2-t-Bu$ | $C(Me)_2$ |
| 12 | H,H | H | 5 | $-CH_2Ph-4-Cl$ | $-S-t-Bu$ | $CH_2OCH_2$ |
| 13 | H,H | H | 5 | $-CH_2Ph-4-Cl$ | $-CH_2CH_2-t-Bu$ | $C(Me)_2$ |
| 14 | H,H | H | 5 | $-CH_2Ph-4-Cl$ | $-S-t-Bu$ | CH(Me) |
| 15 | 6-Cl, 7-Cl | H | 5 | $-CH_2Ph-4-Cl$ | Me | $C(Me)_2$ |
| 16 | H, 7-Cl | H | 5 | $-CH_2Ph-4-Cl$ | Me | $C(Me)_2$ |
| 17 | H,H | 4-allyl | 5 | $-CH_2Ph-4-Cl$ | $-S-t-Bu$ | $C(Me)_2$ |
| 18 | H,H | 4-allyl | 5 | $-CH_2Ph-4-Cl$ | H | $C(Me)_2$ |

TABLE II

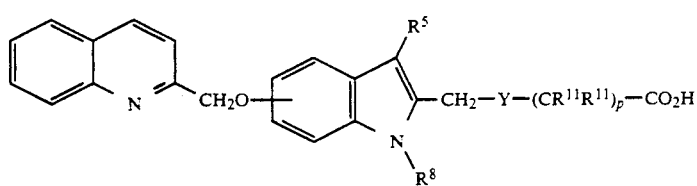

| Ex No. | ATTACH POINT | R⁸ | R⁵ | Y—(CR¹¹R¹¹)$_p$ |
|---|---|---|---|---|
| 19 | 6 | —CH$_2$Ph-4-Cl | —S-t-Bu | C(Me)$_2$ |
| 20 | 4 | —CH$_2$Ph-4-Cl | —S-t-Bu | C(Me)$_2$ |
| 21 | 7 | —CH$_2$Ph-4-Cl | —S-t-Bu | C(Me)$_2$ |
| 22 | 5 | —CH$_2$Ph-4-Cl | —S-t-Bu | CH$_2$OCH(Me) |
| 23 | 4 | —CH$_2$Ph-4-Cl | H | C(Me)$_2$ |
| 24 | 6 | Me | —C(O)Ph-4-Cl | C(Me)$_2$ |
| 25 | 6 | Me | —CH$_2$Ph-4-Cl | C(Me)$_2$ |
| 26 | 5 | —CH$_2$Ph-4-Cl | —O-i-Pr | C(Me)$_2$ |
| 27 | 5 | —CH$_2$Ph-4-Cl | —S-t-Bu | CH(Et) |
| 28 | 5 | —CH$_2$Ph-4-Cl | —C(O)—CF$_3$ | C(Me)$_2$ |
| 29 | 5 | —CH$_2$Ph-4-Cl | —C(O)CH$_2$-t-Bu | CH(Me) |
| 30 | 5 | H | —C(O)CH$_2$-t-Bu | C(Me)$_2$ |
| 31 | 5 | —CH$_2$Ph-4-CF$_3$ | —C(O)CH$_2$-t-Bu | C(Me)$_2$ |
| 32 | 5 | —CH$_2$Ph | —C(O)CH$_2$-t-Bu | C(Me)$_2$ |
| 33 | 5 | —CH$_2$Ph-3-OMe | —C(O)CH$_2$-t-Bu | C(Me)$_2$ |
| 34 | 5 | —CH$_2$CHCH$_2$ | —C(O)CH$_2$-t-Bu | C(Me)$_2$ |
| 35 | 5 | —CH$_2$Ph-4-OMe | —C(O)CH$_2$-t-Bu | C(Me)$_2$ |
| 36 | 5 | Me | —C(O)CH$_2$-t-Bu | C(Me)$_2$ |
| 37 | 6 | H | —CH$_2$Ph-4-Cl | C(Me)$_2$ |
| 38 | 6 | —S(O)$_2$Ph | —CH$_2$Ph-4-Cl | C(Me)$_2$ |
| 39 | 6 | —CH$_2$Ph | —CH$_2$Ph-4-Cl | C(Me)$_2$ |
| 40 | 5 | —CH$_2$Ph-4-Cl | —S(O)$_2$-t-Bu | C(Me)$_2$ |
| 41 | 5 | —CH$_2$Ph-4-Cl | —S(O)-t-Bu | C(Me)$_2$ |
| 42 | 6 | —CH$_2$CHCH$_2$ | —CH$_2$Ph-4-Cl | C(Me)$_2$ |
| 43 | 6 | —(CH$_2$)$_2$CH$_3$ | —CH$_2$Ph-4-Cl | C(Me)$_2$ |
| 44 | 6 | —CH$_2$CH$_3$ | —CH$_2$Ph-4-Cl | C(Me)$_2$ |
| 45 | 5 | —CH$_2$Ph-4-Cl | —C(O)Ph-4-t-Bu | C(Me)$_2$ |
| 46 | 5 | —CH$_2$Ph-4-Cl | —C(O)Ph-4-Cl | C(Me)$_2$ |
| 47 | 5 | —CH$_2$Ph-4-Cl | -t-Bu | C(Me)$_2$ |
| 48 | 5 | —CH$_2$Ph-4-Cl | —C(O)Me | C(Me)$_2$ |
| 49 | 5 | —CH$_2$Ph-4-Cl | —C(O)-c-Pr | C(Me)$_2$ |
| 50 | 5 | —CH$_2$Ph-4-Cl | —C(O)CH$_2$CH$_2$-c-C$_5$H$_9$ | C(Me)$_2$ |
| 51 | 5 | —CH$_2$Ph-4-Cl | —C(O)CH$_2$CH(Me)$_2$ | C(Me)$_2$ |
| 52 | 5 | —CH$_2$Ph-4-Cl | —C(O)Et | C(Me)$_2$ |
| 53 | 5 | —CH$_2$Ph-4-Cl | —C(O)CH(Me)$_2$ | C(Me)$_2$ |
| 54 | 5 | —CH$_2$Ph-4-Cl | —C(O)C(Me)$_3$ | C(Me)$_2$ |
| 55 | 5 | —CH$_2$Ph-4-Cl | —C(O)CH$_2$Ph | C(Me)$_2$ |
| 56 | 5 | —CH$_2$Ph-4-F | —C(O)CH$_2$-t-Bu | C(Me)$_2$ |
| 57 | 5 | —CH$_2$Ph-4-Br | —C(O)CH$_2$-t-Bu | C(Me)$_2$ |
| 58 | 5 | —CH$_2$Ph-4-I | —C(O)CH$_2$-t-Bu | C(Me)$_2$ |
| 59 | 5 | —CH$_2$Ph-4-Cl | —C(Me)$_2$Pr | C(Me)$_2$ |
| 60 | 5 | —CH$_2$Ph-4-Cl | —C(Me)$_2$Et | C(Me)$_2$ |
| 61 | 5 | —CH$_2$Ph-3-F | -t-Bu | C(Me)$_2$ |
| 62 | 5 | —CH$_2$Ph-4-Cl | —CH(Me)$_2$ | C(Me)$_2$ |
| 63 | 5 | —CH$_2$Ph-4-Cl | -c-Pr | C(Me)$_2$ |
| 64 | 5 | —CH$_2$Ph-4-Cl | -(1-Me)-c-Pr | C(Me)$_2$ |
| 65 | 5 | —CH$_2$Ph-4-Cl | -c-C$_5$H$_9$ | C(Me)$_2$ |
| 66 | 5 | —CH$_2$Ph-4-Cl | -c-C$_6$H$_{11}$ | C(Me)$_2$ |
| 67 | 5 | —CH$_2$Ph-4-Cl | —C(Me)$_2$Ph | C(Me)$_2$ |
| 68 | 5 | —CH$_2$Ph-4-Cl | —C(Me)$_2$Ph-4-Cl | C(Me)$_2$ |
| 69 | 5 | —CH$_2$Ph-4-Cl | -1-Ad | C(Me)$_2$ |
| 70 | 5 | —CH$_2$Ph-4-Cl | —CH$_2$-1-Ad | C(Me)$_2$ |
| 71 | 6 | -t-Bu | —CH$_2$Ph-4-Cl | C(Me)$_2$ |
| 72 | 6 | —C(Me)$_2$Et | —CH$_2$Ph-4-Cl | C(Me)$_2$ |
| 73 | 5 | —CH$_2$Ph-4-Cl | —C(O)CH$_2$-t-Bu | C(Et)$_2$ |

TABLE III

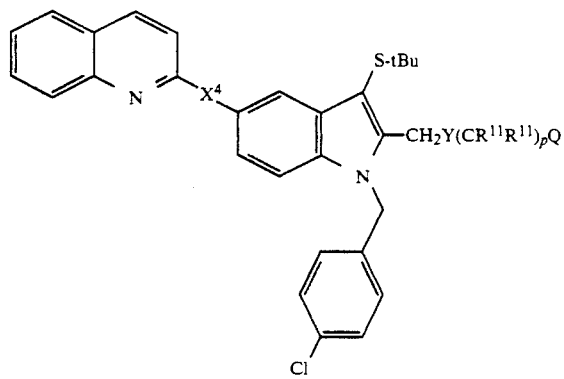

Ie

| Ex. No. | $X^4$ | $Y-(CR^{11}R^{11})_p$ | Q |
|---|---|---|---|
| 76 | $CH_2O$ | $C(Me)_2$ | $-C(O)NHS(O)_2Me$ |
| 77 | $CH_2O$ | $C(Me)_2$ | $-NHS(O)_2Ph-4-Me$ |
| 78 | $CH_2O$ | $C(Me)_2$ | $-C(O)NH-t-Bu$ |
| 79 | $CH_2O$ | $OCH_2CH(Me)$ | $-CO_2H$ |
| 80 | $CH_2O$ | $CH_2CH_2$ | Tz |
| 81 | $CH_2O$ | $OCH(Me)$ | Tz |
| 82 | $CH_2O$ | $C(Me)_2$ | $-S(O)_2NH-Et$ |
| 83 | $CH_2O$ | $C(Me)_2$ | $-CO_2CH_2C(O)NMe_2$ |
| 84 | $CH_2O$ | $C(Me)_2$ | $-C(O)NHCH_2CO_2H$ |
| 85 | $CH_2O$ | $C(Me)_2$ | $-CH_2OH$ |
| 86 | (E)-CH=CH | $C(Me)_2$ | $-CO_2H$ |
| 87 | $CH_2CH_2$ | $C(Me)_2$ | $-CO_2H$ |
| 88 | $CH_2S$ | $C(Me)_2$ | $-CO_2H$ |
| 89 | $CH_2S(O)_2$ | $C(Me)_2$ | $-CO_2H$ |

Assays for Determining Biological Activity

Compounds of Formula I can be tested using the following assays to determine their mammalian leukotriene biosynthesis inhibiting activity.

Rat Peritoneal Polymorphonuclear (PMN) Leukocyte Assay

Rats under ether anesthesia are injected (i.p.) with 8 mL of a suspension of sodium caseinate (6 grams in ca. 50 mL water). After 15-24 hr. the rats are sacrificed ($CO_2$) and the cells from the peritoneal cavity are recovered by lavage with 20 mL of buffer (Eagles MEM containing 30 mM HEPES adjusted to pH 7.4 with NaOH). The cells are pelleted (350×g, 5 min.), resuspended in buffer with vigorous shaking, filtered through lens paper, recentrifuged and finally suspended in buffer at a concentration of 10 cells/mL. A 500 mL aliquot of PMN suspension and test compound are preincubated for 2 minutes at 37° C., followed by the addition of 10 mM A-23187. The suspension is stirred for an additional 4 minutes then bioassayed for $LTB_4$ content by adding an aliquot to a second 500 mL portion of the PMN at 37° C. The $LTB_4$ produced in the first incubation causes aggregation of the second PMN, which is measured as a change in light transmission. The size of the assay aliquot is chosen to give a submaximal transmission change (usually −70%) for the untreated control. The percentage inhibition of $LTB_4$ formation is calcuated form the ratio of transmission change in the sample to the transmission change in the compound-free control.

Human Polymorphonuclear (PMN) Leukocyte $LTB_4$ Assay

A. Preparation of Human PMN

Human blood was obtained by antecubital venepuncture from consenting volunteers who had not taken medication within the previous 7 days. The blood was immediately added to 10% (v/v) trisodium citrate (0.13M) or 5% (v/v) sodium heparin (1000 IU/mL). PMNs were isolated from anticoagulated blood by dextran sedimentation of erythrocytes followed by centrifugation through Ficoll-Hypaque (specific gravity 1.077), as described by Boyum (Scand. J. Clin. Lab. Invest., 21 (Supp. 97), 77(1968)). Contaminating erythrocytes were removed by lysis following exposure to ammonium chloride (0.16M) in Tris buffer (pH 7.65), and the PMNs resuspended at $5 \times 10^5$ cells/mL in HEPES (15 mM)-buffered Hanks balanced salt solution containing $Ca^{2+}$ (1.4 mM) and $Mg^{2+}$ (0.7 mM). pH 7.4. Viability was assessed by Trypan blue exclusion and was typically greater than 98%.

B. Generation and Radioimmunoassay of $LTB_4$

PMNs (0.5 mL; $2.5 \times 10^5$ cells) were placed in plastic tubes and incubated (37° C., 2 min) with test compounds at the desired concentration or vehicle (DMSO, final concentration 0.2%) as control. The synthesis of $LTB_4$ was initiated by the addition of calcium ionophore A23187 (final concentration 10 mM) or vehicle in control samples and allowed to proceed for 5 minutes at 37° C. The reactions were then terminated by the addition of cold methanol (0.25 mL) and samples of the entire PMN reaction mixture were removed for radioimmunoassay of $LTB_4$.

Samples (50 mL) of authentic $LTB_4$ of known concentration in radioimmunoassay buffer (RIA buffer (potassium phosphate 1 mM; disodium EDTA 0.1 mM; Thimerosal 0.025 mM; gelatin 0.1%, pH 7.3) or PMN reaction mixture diluted 1:1 with RIA buffer were added to reaction tubes. Thereafter [$^3$H]-LTB$_4$ (10 nCi in 100 mL RIA buffer) and LTB$_4$-antiserum (100 mL of a 1:3000 dilution in RIA buffer) were added and the tubes vortexed. Reactants were allowed to equilibrate by incubation overnight at 4° C. To separate antibody-bound from free LTB$_4$, aliquots (50 mL) of activated charcoal (3% activated charcoal in RIA buffer containing 0.25% Dextran T-70) were added, the tubes vortexed, and allowed to stand at room temperature for 10 minutes prior to centrifugation (1500×g; 10 min; 4° C.). The supernatants containing antibody-bound LTB$_4$ were decanted into vials and Aquasol 2 (4 mL) was added. Radioactivity was quantified by liquid scintillation spectrometry. Preliminary studies established that the amount of methanol carried into the radioimmunoassay did not influence the results. The specificity of the antiserum and the sensitivity of the procedure have been described by Rokach et al. (*Prostaglandins Leukotrienes and Medicine* 1984, 13, 21.) The amount of LTB$_4$ produced in test and control (approx. 20 ng/10$^6$ cells) samples were calculated. Inhibitory dose-response curves were constructed using a four-parameter algorithm and from these the IC$_{50}$ values were determined.

Asthmatic Rat Assay

Rats are obtained from an inbred line of asthmatic rats. Both female (190-250 g) and male (260-400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate was supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynowraph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 mgm/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1-4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an ED$_{50}$ is determined. This is defined as the dose (mg/kg) which would inhibit the duration of symptoms by 50%.

The invention is further defined by reference to the following examples, which are intended to be illustrative and not limiting. All temperatures are in degrees Celsius.

EXAMPLE 1

3-[N-(p-Chlorobenzyl)-3-(t-butylthio)-5-(quinolin-2-ylmethoxy)indol-2-yl]-2,2-dimethylpropanoic acid Step A:
3-[N-p-Chlorobenzyl-3-(t-butylthio)-5-methoxyindol-2-yl]-2,2-dimethylpropanoic acid methyl ester To a solution of 39 g of methyl 5-(t-butylthio)-2,2-dimethyl-4-oxopentanoate in a mixture of 300 mL of toluene and 150 mL of glacial acetic acid was added 15 g of NaOAc and 50 g of 1-(4-methoxyphenyl)-1-(p-chlorobenzyl)hydrazine hydrochloride. The reaction was maintained with stirring at room temperature for 3 days under argon in the dark. The mixture was poured into 3 L of H$_2$O and extracted with 3×500 mL of EtOAc. The ethyl acetate was washed with 3×500 mL of water then solid NaHCO$_3$ was added. The mixture was filtered and the filtrate washed twice with water. The organic phase was dried over MgSO$_4$ and evaporated to dryness to provide the title compound. m.p. 102°-103° C.

Step B:
3-[N-(p-Chlorobenzyl)-3-(t-butylthio)-5-methoxyindol-2-yl]-2,2-dimethylpropanoic acid The compound from Step A was hydrolysed using 325 mL of THF, 600 mL of MeOH and 325 mL of 1.0M LiOH. The solution was heated to 80° C. for 3 h. The solution was acidified with 1N HCl and extracted with 3×200 mL of EtOAc. The organic phase was washed with 0ater (2×150 mL) and dried over MgSO$_4$. The solution was evaporated to dryness to provide the title compound. m.p. 190°-191° C.

Anal C, H, N: Calc. C 65.27; H 6.57; N 3.04, Found C 65.28; H 6.58; N 3.04.

Step C: Methyl 3-[N-(p-chlorobenzyl)-5-hydroxy-3-(t-butylthio)indol-2-yl]-2,2-dimethylpronanoate A solution of 61 mL of t-butylthiol in 650 mL of dry HMPA at 0° C. was treated portionwise with 26 g of 50% NaH in mineral oil after removal of oil with hexane. The reaction was stirred at RT for 30 mins and 46 g of the compound from Step B was added.

The reaction was then heated under N$_2$ at 175° C. for 5 hours. The solution was cooled, and poured onto crushed ice, after which it was treated with 2N HCl to pH 5 and extracted with EtOAc (3×500 mL). The organic phase was washed with H$_2$O (3×200 mL) dried (MgSO$_4$) and evaporated. The residue was dissolved in 300 mL of ether and ethereal diazomethane was added until all acid was consumed. The excess solvent was removed and the oily residue triturated with hexane to leave a crystalline mass which was recrystallized from EtOAc/hexane to provide the title compound as a white crystalline solid, m.p. 170°–171° C. From the mother liquors was isolated methyl 3-[N-(p-t-butylthiobenzyl)-5-hydroxy-3-(t-butylthio)indol-2-yl]-2,2-dimethyl propanoate which was used as such in Example 3.

Step D: Methyl 3-[N-(p-chlorobenzyl)-3-(t-butylthio)-5-(quinolin-2-ylmethoxy)indol-2-yl]-2,2-dimethylpropanoate Methyl 3-[N-(p-chlorobenzyl)-5-hydroxy-3-(t-butylthio)indol-2-yl]-2,2-dimethylpropanoate (33.6 g) from Step C was dissolved in 500 mL of dry DMF and the solution was charged with 2.4 g of KI, 30.3 g of $K_2CO_3$, 4.77 g of $Cs_2CO_3$ and 23.5 g of 2-(chloromethyl)quinoline hydrochloride. The reaction was stirred at RT, under $N_2$, for 72 hours then it was poured into water (1.5 L), acidified with 1N HCl and extracted (3×200 mL) with $CH_2Cl_2$. The organic phase was washed with $H_2O$ (3×150 mL), dried and evaporated. The residue was dissolved in hot EtOAc and upon cooling crystallized to deposit 22.0 g of the title compound, m.p. 166°–167° C.

Step E: 3-[N-(p-Chlorobenzyl)-3-(t-butylthio)-5-(quinolin-2-ylmethoxy)indol-2-yl]-2,2-dimethylpropanoic acid Using the hydrolytic procedure of Step B but substituting the ester of Step D for the ester of Step A provided the title compound, which was recrystallized from 1:1 EtOAc/hexane. m.p. 208° C.
Anal C, H, N: Calc. C 69.55; H 6.01; N 4.77, Found C 69.77; H 6.05; N 4.70.

EXAMPLE 1A

3-[N-(p-Chlorobenzyl)-3-(t-butylthio)-5-(quinolin-2-ylmethoxy)indol-2-yl]-2,2-dimethylpropanoic acid Step A: N-Acetyl-4-(quinolin-2-ylmethoxy)aniline A mixture containing 2-(chloromethyl)quinoline-hydrochloride (100.0 g), 4-acetamidophenol (70.69 g) and milled anhydrous potassium carbonate (194 g) was stirred in DMF (1.2 L) using a mechanical stirrer for 48 hours. The mixture was carefully poured onto ice/water (3 L) with vigourous stirring. After the ice had melted, the solid was filtered and rinsed thoroughly with water. It was recrystallized from 95% ethanol and filtered to give the title compound in three crops.

Step B: 4-(Quinolin-2-ylmethoxy)aniline

A suspension of N-acetyl-4-(quinolin-2-yl-methoxy)aniline (Step A, 108.9 g) in 1 L of 95% ethanol containing 10M KOH (120 mL) was heated at reflux under nitrogen in a heating mantle. When the hydrolysis was complete (approx. 36 h), the reaction mixture was cooled and ethanol was partially removed under vacuum. The mixture was then diluted with water (200 mL) and the fine off-white crystals were collected and thoroughly rinsed with water. The material, after air-drying, yielded the title compound which was used as such in the next step.

Step C: 4-(Quinolin-2-ylmethoxy)phenylhydrazine

A quantitiy of 84 g of 4-(quinolin-2-ylmethoxy)aniline from Step B was suspended in 300 mL of deionized $H_2O$ and 84 mL of 12M HCl. The suspension was stirred vigourously to obtain a fine particle suspension. Then a precooled solution (5° C.) of 23.88 g of sodium nitrite dissolved in 75 mL of deionized $H_2O$ was added dropwise to the suspension at 5° C. over 25 minutes. The solution was stirred at 5° C. for 60 min to obtain the diazonium salt as a clear brown solution. The presence of excess $HNO_2$ was confirmed by KI-starch paper, and the pH of the solution was about 3.0. If a white suspension persisted after 1 h, the mixture was filtered through a glass wool plug, to give the diazonium salt in the filtrate.

In the meantime a sodium hydrosulfite solution was prepared by dissolving 321 g of sodium hydrosulfite (approx. 85% purity) in 2 L of deionized water, and cooled at 0° to 5° C. To this solution were added 15 mL of 2N NaOH and 2 L of ether. The biphasic solution was kept near 0° C. by addition of crushed ice and was stirred vigorously. To this solution was added dropwise the diazonium salt solution with stirring maintained throughout. At the end of the addition an orange solid was formed and 600 mL of NaOH (2N) was added over 30 minutes. The reaction was finally stirred for 60 minutes at 25° C. The solid was collected, suspended in ether (1 L) and filtered. The process was repeated with 2 L of water to yield the title compound as a pale yellow solid after freeze-drying overnight. m.p. 73°–85° C. (dec).

Step D: 1-(p-Chlorobenzyl)-1-[4-(quinolin-2-yl-methoxy)-phenyl]hydrazine

A quantity of 10 g of 4-(quinolin-2-ylmethoxy)-phenylhydrazine from Step C was added to a solution of 10.5 mL of diisopropylethylamine and 150 mL of $CH_2Cl_2$. To the yellow suspension was added 9.11 g of p-chlorobenzyl chloride followed by 3.64 g of $Bu_4NBr$ and 50 mL of $CH_2Cl_2$. The reaction was stirred for approximately 24 hours. When no starting material remained, the reaction was diluted with $H_2O$ and extracted 3 times with $CH_2Cl_2$. The combined organic phase was washed once with water and dried ($MgSO_4$), filtered and evaporated to dryness. The solid residue was dried under vacuum overnight prior to being swished in ether/methanol 90/10 to give the title compound as a pale yellow solid. m.p. 130° C.

Step E: 3-[N-(p-Chlorobenzyl)-3-(t-butylthio)-5-(quinolin-2-ylmethoxy)indol-2-yl]-2,2-dimethylpropanoic acid The methyl ester of the title compound was prepared according to the method described in Step A of Example 1 but using the phenylhydrazine from Step D of Example 1A as starting material.

The title compound was prepared under the conditions described in Step B of Example 1.

EXAMPLE 2

3-[N-(p-Chlorobenzyl)-3-methyl-5-(quinolin-2-yl-methoxy)indol-2-yl]-2,2-dimethylpropanoic acid The title compound was prepared according to the method of Example 1, but using methyl 2,2-dimethyl-4-oxohexanoate as starting material in Step A in place of methyl 5-t-butylthio-2,2-dimethyl-4-oxopentanoate. m.p. 215°–217° C.

EXAMPLE 3

3-[N-(p-t-Butylthiobenzyl)-3-(t-butylthio)-5-(quinolin-2-ylmethoxy)indol-2-yl]-2,2-dimethylpropanoic acid The methyl ester byproduct from Step C of Example 1 was reacted 2-(chloromethyl)quinoline according to the conditions of Steps D & E of Example 1 to provide the title compound. m.p. 172°–173° C.

EXAMPLE 4

3-[N-(p-Chlorobenzyl)-3-(phenylthio)-5-(quinolin-2-ylmethoxy)indol-2-yl]-2,2-dimethylpropanoic acid The title compound was prepared according to the method described for Example 1, but substituting methyl-5-phenylthio-2,2-dimethyl-4-oxopentanoate for methyl 5-t-butylthio-2,2-dimethyl-4-oxopentonoate in Example 1 (Step A).

Anal. C, H, N for sodium salt . 2 $H_2O$: Calc. C 64.91; H 5.30; N 4.20, Found C 64.94; H 5.04; N 4.15.

EXAMPLE 5

3-[N-(p-Chlorobenzyl)-3-(phenylsulfonyl)-5-(quinolin-2-ylmethoxy)indol-2-yl]-2,2-dimethylpropanoic acid, N-oxide Methyl 3-[N-(p-chlorobenzyl)-3-(phenylthio)-5-(quinolin-2-ylmethoxy)indol-2-yl]-2,2-dimethyl propanoate 430 mg) from Step D of Example 4 was dissolved in 5 mL cold $CH_2Cl_2$ and treated with a solution of 448 mg of 80% m-chloroperbenzoic acid (MCPBA) in $CH_2Cl_2$. After 24 hours, the solution was poured onto 10 mL of sat. aqueous $NaHCO_3$ solution, extracted with 3×10 mL of $CH_2Cl_2$, washed with 2×10 mL of $H_2O$, dried with magnesium sulfate and evaporated to dryness. The residue was crystallised from 2:1 $CH_2Cl_2$/EtOAc to yield 280 mg of the title compound as its methyl ester. Hydrolysis using the conditions described in Example 1 (Step B) provided the title compound, m.p. 197° C. (dec.)

Anal. C, H, N: Calc. C 66.0; H 4.77; N 4.28, Found C 66.06; H 4.77; N 4.19.

EXAMPLES 6 AND 7

3-[N-(p-Chlorobenzyl)-3-(phenylsulfonyl)-5-(quinolin-2-ylmethoxy)indol-2-yl]-2,2-dimethylpropanoic acid
and
3-[N-(p-Chlorobenzyl)-3-(phenylsulfinyl)-5-(quinolin-2-ylmethoxy)indol-2-yl]-2,2-dimethylpropanoic acid Methyl 3-[N-p-chlorobenzyl-3-(phenyl thio)-5-(quinolin-2-methoxy)indol-2-yl]-2,2-dimethyl propanoate (430 mg) from Example 4 (Step D) was dissolved in 5 mL of cold methylene chloride and a solution of 150 mg of 80% (MCPBA) in methylene chloride was added. After 24 hours, the reaction solution was poured onto 10 mL of saturated aqueous sodium bicarbonate solution and this mixture was extracted 3 times with 10 mL of methylene chloride. The combined organic phases were washed twice with 10 mL of water, dried with magnesium sulfate and evaporated under vacuum.

Chromatography over silica gel (2 hexane:1 ethyl acetate) provided two compounds which were separately hydrolyzed using the procedure described in Example 1 (Step B).

3-[N-(p-Chlorobenzyl)-3-(phenylsulfonyl)-5-(quinolin-2-ylmethoxy)indol-2-yl]-2,2-dimethylpropanoic acid Anal. C, H, N for sodium salt $H_2O$: Calc. C 63.57; H 4.89; N 4.12, Found C 63.28; H 4.77; N 3.90.

3-[N-(p-Chlorobenzyl)-3-(phenylsulfinyl)-5-(quinolin-2-ylmethoxy)indol-2-yl]-2,2-dimethylpropanoic acid Anal. C, H, N for sodium salt . $H_2O$: Calc C 63.38; H 5.17; N 4.11, Found C 63.28; H 4.89; N 3.97.

EXAMPLE 8

3-[N-(p-Chlorobenzyl)-5-(quinolin-2-ylmethoxy)indol-2-yl]-2,2-dimethylpropanoic acid

Step A: Methyl 3-[N-(p-chlorobenzyl)-5-hydroxyindol-2-yl]-2,2-dimethylpropanoate A suspension of 1.0 g of 3-[N-(p-chlorobenzyl)-3-(t-butylthio)-5-methoxyindol-2-yl]-2,2-dimethylpropanoic acid (from Example 1 Step B) in 50 mL of $CH_2Cl_2$ was treated with 1.3 mL of ethanethiol and 3.47 g of $AlCl_3$ at 0° C. under argon. After 40 min the mixture was poured onto 50 mL 1N HCl, extracted with 3×50 mL of $CH_2Cl_2$ washed with 2×50 mL of $H_2O$, dried with $MgSO_4$ and the solvent removed. The residue was dissolved in 10 mL ether and ethereal diazomethane added until all the acid was consumed. The excess solvent was removed and the residue chromatographed on silica gel to afford the title compound.

Step B: 3-[N-(p-Chlorobenzyl)-5-(quinolin-2-yl-methoxy)indol-2-yl]-2,2-dimethylpropanoic acid The title compound was prepared by treating the ester from Step A with 2-(choromethyl)quinoline hydrochloride under the conditions of Step D and effecting hydrolysis under the conditions of Example 1 (Step B), m.p. 193°–194° C.

EXAMPLE 9

3-[N-(p-Chlorobenzyl)-3-benzoyl-5-(quinolin-2-ylmethoxy)indol-2-yl]-2,2-dimethylpropanoic acid

Step A: Methyl 3-[N-(p-chlorobenzyl)-3-benzoyl-5-benzoyloxyindol-2-yl]-2,2-dimethylpropanoate Methyl 3-[N-(p-chlorobenzyl)-5-hydroxy indol-2-yl]-2,2-dimethylpropanoate (609 mg) from Example 8 (Step A) was dissolved in 10 mL of 1,2-dichloroethane and the solution charged with 0.5 mL of benzoyl chloride and 680 mg of $AlCl_3$. The reaction was heated to 80° C. under argon for 1.5 h, then quenched with 20 mL of 0.5N Na, K tartrate solution, extracted with 3×20 mL of ether, washed with 10 mL of $H_2O$ and dried ($MgSO_4$). Removal of solvent provided an oily residue which was chromatographed on silica gel to give the title compound.

Step B: Methyl 3-[N-(p-chlorobenzyl)-3-benzoyl-5-hydroxyindol-2-yl]-2,2-dimethylpropanoate The compound from Step A (300 mg) was dissolved in 4 mL of MeOH and treated with 1 mL of a 1.4M solution of NaOMe in MeOH under argon for 3 hrs. The mixture was poured onto 20 mL of $NH_4OAc$ (25% solution), extracted with 3×15 mL of ether, washed with 10 mL of $H_2O$, dried over $MgSO_4$ and the solvent removed under vacuum. The resulting oil was purified by chromatography on silica gel to afford the title compound.

Step C:
3-[N-(p-Chlorobenzyl)-3-benzoyl-5-(quinolin-2-ylmethoxy)indol-2-yl]-2,2-dimethylpropanoic acid The title compound was prepared using the conditions described in Step D and Step E of Example 1, but substituting the ester from Step B for the ester of Example 1, Step C; m.p. 165°–166° C.

EXAMPLE 10

3-[N-(p-Chlorobenzyl)-3-benzyl-5-(quinolin-2-ylmethoxy)indol-2-yl]-2,2-dimethylpropanoic acid Step A: Methyl 3-[N-(p-Chlorobenzyl)-3-benzyl-5-(benzoyloxy)indol-2-yl]-2,2-dimethylpropanoate Methyl 3-[N-(p-chlorobenzyl)-3-benzoyl-5-(benzoyloxy)indol-2-yl]-2,2-dimethylpropanoate (360 mg) (prepared in Step A of Example 9), 800 mg of $ZnI_2$, and 500 mg of sodium cyanoborohydride were stirred in 5 mL of dichloroethane at RT under argon for 30 min. The temperature was then raised to 65° C. for 3 hr. After the solution had cooled, it was poured onto 10 mL of $NH_4OAc$ (25% solution), extracted with $3 \times 15$ mL of ether, washed with 10 mL of $H_2O$ and dried ($MgSO_4$). The solution was evaporated to dryness and the residue was chromatographed on silica gel to yield the title compound as a white foam.

Step B:
3-[N-(p-Chlorobenzyl)-3-benzyl-5-(quinolin-2-ylmethoxy)indol-2-yl]-2,2-dimethylpropanoic acid The title compound was prepared under the conditions described in Step B and Step C of Example 9 but substituting the ester from Example 10 (Step A) for the ester of Example 9 (Step A), m.p. 178° C.

EXAMPLE 11

3-[N-(p-Chlorobenzyl)-3-(3,3-dimethyl-1-oxo-1-butyl)-5-(quinolin-2-ylmethoxy)indol-2-yl]-2,2-dimethylpropanoic acid The title compound was prepared according to the method described in Example 9, but using t-butylacetylchloride in place of benzoyl chloride in Step A, m.p. 183°–184° C.

EXAMPLE 12

2-[N-(p-Chlorobenzyl)-3-(t-butylthio)-5-(quinolin-2-ylmethoxy)indol-2-yl]ethoxyethanoic acid Step A: Methyl 2-[N-(p-Chorobenzyl)-3-(t-butylthio)-5-(quinolin-2-ylmethoxy)indol-2-yl]ethanoate The title compound was prepared according to the method outlined in Steps A-D of Example 1, but using methyl 4-t-butylthio-3-oxo-butanoate in Step A instead of methyl 5-t-butylthio-2,2-dimethyl-4-oxopentanoate.

Step B:
2-[N-(p-Chlorobenzyl)-3-(t-butylthio)-5-(quinolin-2-ylmethoxy)indol-2-yl]ethanol The compound from Step A (192 mg) was dissolved in 3 mL of THF at RT under an argon atmosphere and treated with 30 mg of lithium aluminum hydride. After 1 hr, the reaction was poured onto 10 mL of 0.5N Na,K tartrate solution and extracted with $3 \times 10$ mL of EtOAc. The organic layer was washed with 10 mL of $H_2O$, dried ($MgSO_4$) and evaporated to dryness to yield the title compound.

Step C:
2-[N-(p-Chlorobenzyl)-3-(t-butylthio)-5-(quinolin-2-ylmethoxy)indol-2-yl]ethoxyethanoic acid To 91 mg of 2-[N-(p-chlorobenzyl)-3-(t-butylthio)-5-(quinolin-2-ylmethoxy)indol-2-yl]ethanol from Step B in 2 mL THF at 0° C. under an argon atmosphere was added 40 mg of 80% sodium hydride over 30 min. Ethyl bromoacetate (0.3 ml) was added to the solution and the reaction stirred at RT overnight. The reaction was poured onto 10 mL of $NH_4OAc$ (25% solution), extracted with $3 \times 10$ mL of EtOAc, washed with 20 mL of $H_2O$ and dried over $MgSO_4$. Removal of the solvent followed by column chromatography on silica gel afforded the ethyl ester of title compound. Hydrolysis of this ester under the conditions described in Step B of Example 1 provided the title compound, m.p. 185° C. (dec.).

EXAMPLE 13

3-[N-(p-Chlorobenzyl)-3-(3,3-dimethyl-1-butyl)-5-(quinolin-2-ylmethoxy)indol-2-yl]-2,2-dimethylpropanoic acid The title compound was prepared according to the method described in Example 10 but using methyl 3-[N-(p-chlorobenzyl)-3-(3,3-dimethy-1-oxo-1-butyl)-5-(t-butylacetyloxy)-indol-2-yl]-2,2-dimethylpropanoate (obtained as an intermediate from Example 11) as starting material, m.p. 188° C. (dec.).

EXAMPLE 14

3-[N-(p-Chlorobenzyl)-3-(t-butylthio)-5-(quinolin-2-ylmethoxy)indol-2-yl]-2-methylpropanoic acid The title compound was prepared according to the method of Example 1 using methyl 5-t-butylthio-2-methyl-4-oxopentanoate as starting material in Step A in place of methyl 5-t-butylthio-2,2-dimethyl-4-oxopentanoate.

$^1H$ NMR (250 MHz, acetone-$d_6$) δ1.05 (3H, d, J=6Hz), 1.15 (9H, s), 2.7 (1H, m), 3.2 (2H, d, J=7Hz), 5.4 (2H, s), 5.6 (2H, s), 6.9 (1H, dd), 7.0 (2H, d), 7.3 (4H, m), 7.6 (1H, td), 7.7 (1H, d), 7.8 (1H, td), 7.9 (1H, d), 8.1 (1H, d), 8.3 ppm (1H, d).

EXAMPLE 15

3-[N-(p-Chlorobenzyl)-3-methyl-5-(6,7-dichloroquinolin-2-ylmethoxy)indol-2-yl]-2,2-dimethylpropanoic acid The title compound was prepared according to the method described in Example 1 but using methyl 2,2-dimethyl-4-oxohexanoate as starting material in Step A and 2-(bromomethyl)-6,7-dichloroquinoline in Step D.

Anal. C, H, N: Calc. C 63.21; H 4.74; N 4.91, Found C 63.47; H 4.94; N 4.67.

EXAMPLE 16

3-[N-(p-Chlorobenzyl)-3-methyl-5-(7-chloroquinolin-2-ylmethoxy)indol-2-yl]-2,2-dimethylpropanoic acid The title compound was prepared according to the method described in Example 15 but using 2-(bromomethyl)-7-chloroquinoline instead of 2-(bromomethyl)-6,7-dichloroquinoline. m.p. 105°–107° C.

Anal. C, H, N: Calc. C 67.41; H 5.24; N 5.24, Found C 67.82; H 5.12; N 4.32.

EXAMPLE 17

3-[N-(p-Chlorobenzyl)-4-allyl-5-(quinolin-2-ylmethoxy)-3-(t-butylthio)indol-2-yl]-2,2-dimethylpropanoic acid Step A: Methyl 3-{N-(p-chlorobenzyl)-5-allyloxy-3-(t-butylthio)indol-2-yl]-2,2-dimethylpropanoic acid 500 mg. of methyl 3-[N-(p-chlorobenzyl)-5-hydroxy-3-(t-butylthio)indol-2-yl]-2,2-dimethylpropanoate from Step C of Example 1 was dissolved in 5 mL of DMF and 20 mg of $K_2CO_3$ and 150 mg of allyl bromide were added. The reaction was stirred for 16 hrs. Water was added and the organic phase extracted with EtOAc (3×5mL). The organic phase was dried with $MgSO_4$ and evaporated to yield, after chromatography on silica gel (EtOAc:hexane 1:5), the title compound.

Step B: Methyl 3-[N-(p-chlorobenzyl)-3-(t-butylthio)-4-allyl-5-hydroxyindol-2-yl]-2,2-dimethylpropanoate 500 mg of the ester of Step A was converted to the title compound by heating to 180° in m-xylene for 4 hours.

Step C: 3-[N-(p-Chlorobenzyl)-4-allyl-5-(quinolin-2-ylmethoxy)-3-(t-butylthio)indol-2-yl]-2,2-dimethylpropanoic acid The title compound was prepared from the compound of Step B using the methodology of Example 1, (Steps D and E), m.p. 103°–105° C.

Anal. C, H, N: Calc. C 69.09; H 6.11; N 4.35, Found C 70.55; H 6.31; N 4.29.

EXAMPLE 18

3-[N-(p-Chlorobenzyl)-4-allyl-5-(quinolin-2-yl-methoxy)indol-2-yl]-2,2-dimethylpropanoic acid The methyl ester of the title compound was prepared according to the method of Example 17 but substituting methyl 3-[N-(p-chlorobenzyl)-5-hydroxyindol-2-yl]-2,2-dimethylpropanoate as starting material (obtained in Step A Example 8) for the ester in Example 17 (Step A). Hydrolysis was then effected according to the conditions of Step B of Example 1 to provide the title compound, m.p. 196°–197° C. (dec.).

EXAMPLE 19

3-[N-(p-Chlorobenzyl)-6-(quinolin-2-ylmethoxy)-3-(t-butylthio)indol-2-yl]-2,2-dimethylpropanoic acid The title compound was prepared according to the conditions of Example 1, Steps A to E, but substituting 1-(3-methoxyphenyl)-1-(p-chlorobenzyl)hydrazine hydrochloride for the starting material in Example 1 (Step A). Chromatographic separation of the desired regioisomer was achieved at Step A by isolating the most polar product, methyl 3-[N-(p-chlorobenzyl)-3-(t-butylthio)-6-methoxyindol-2-yl]-2,2-dimethylpropanoate. The properties of the title compound were as follows: m.p. 165°–167° C.

Anal C, H, N: Calc. C 69,54; H 6.01; N 4.77, Found C 69.46; H 6.18; N 4.96.

EXAMPLE 20

3-[N-(p-Chlorobenzyl)-4-(quinolin-2-ylmethoxy)-3-(t-butylthio)indol-2-yl]-2,2-dimethylpropanoic acid Methyl 3-[N-(p-chlorobenzyl)-3-(t-butylthio)-4-methoxyindol-2-yl]-2,2-dimethylpropanoate was obtained as a by-product from Step A of Example 19 and isolated by chromatography as the less polar product. The compound was used as starting material for the preparation of the title product using the methodology of Steps B to E of Example 1.

Anal C, H, N: Calc. C 69.54; H 6.01; N 4.77; Found C 69.80; H 6.24; N 4.86.

EXAMPLE 21

3-[N-(p-Chlorobenzyl)-3-(t-butylthio)-7-(quinolin-2-ylmethoxy)indol-2-yl]-2,2-dimethylpropanoic acid The title product was prepared according to Steps A to E of Example 1 but substituting 1-(2-methoxyphenyl)-1-(p-chlorobenzyl)hydrazine hydrochloride for 1-(4-methoxyphenyl)-1-(p-chlorobenzyl) hydrazine hydrochloride in Example 1 (Step A), m.p. 206° C.

Anal. C, H, N: Calc. C 69.54; H 6.01; N 4.77, Found C 69.40; H 5.88; N 4.65.

EXAMPLE 22

2-[2-[N-(p-Chlorobenzyl)-3-(t-butylthio)-5-(quinolin-2-ylmethoxy)indol-2-yl]ethoxy]propanoic acid sodium salt dihydrate Step A: Methyl 2-[2-[N-(p-chlorobenzyl)-3-(t-butylthio)-5-quinolin-2-ylmethoxy)indol-2-yl]ethoxy]propanoate The title compound was prepared from 251 mg of 2-[N-(p-chlorobenzyl)-3-(t-butylthio)-5-(quinolin-2-ylmethoxy)indol-2-yl]ethanol (Step B of Example 12) under the conditions described in Step C of Example 12 using methyl D,L-2-bromopropanoate instead of ethyl bromoacetate.

Step B: 2-[2-[N-(p-Chlorobenzyl)-3-(t-butylthio)-5-(quinolin-2-ylmethoxy)indol-2-yl]ethoxy]propanoic acid sodium salt dihydrate The acid corresponding to the title compound of Example 22 was prepared from the ester of Step A of Example 22 under the conditions described in Step B of Example 1. A quantity of 204 mg of the acid was suspended in 1.5 mL of EtOH and treated with 1 equiv. of 1N aq. NaOH and freezed dried for 2 days to afford the title compound.

Anal. C, H, N: Calc. C 61.25; H 5.61; N 4.33, Found C 61.75; H 5.70; N 3.97.

EXAMPLE 23

3-[N-(p-Chlorobenzyl)-4-(quinolin-2-ylmethoxy)indo-2-yl]-2,2-dimethylpropanoic acid Step A: Methyl 3-[N-(p-chlorobenzyl)-4-hydroxyindol-2-yl]-2,2-dimethylpropanoate The title compound was prepared using methodology from Step A of Example 8 but substituting 3-[N-(p-chlorobenzyl)-3-(t-butylthio)-4-methoxy indol-2-yl]-2,2-dimethylpropanoic acid (Step B of Example 20) for the propanoic acid in Example 8 (Step A).

Step B:
3-[N-(p-Chlorobenzyl)-4-(quinolin-2-yl-methoxy)indol-2-yl]-2,2-dimethylpropanoic acid The title product was prepared according to conditions described in Steps D and E of Example 1 substituting methyl 3-[N-(p-chlorobenzyl)-4-hydroxy indol-2-yl]-2,2-dimethylpropanoate for the propanoate in Example 1 (Step D), m.p. 158°–160° C.

Anal. C, H, N: Calc. C 72.20; H 5.45; N 5.61, Found C 72.25; H 5.60; N 5.75.

EXAMPLE 24

3-[N-Methyl-3-(p-chlorobenzoyl)-6-(quinolin-2-yl-methoxy)indol-2-yl]-2,2-dimethylpropanoic acid

Step A: Methyl 3-[6-methoxy-3-(t-butylthio)indol-2-yl]-2,2-dimethylpropanoate A mixture of 4.2 g of 3-methoxyphenylhydrazine hydrochloride and 4.9 g of methyl 5-(t-butylthio)-2,2-dimethyl-4-oxopentanoate in 100 mL of t-butanol was refluxed for 18 hours. The mixture was cooled to R.T., and evaporated to dryness. The residue was suspended in ether (150 ml) and stirred for 30 min. The salts were filtered and the filtrate evaporated to dryness to give a residue which was chromatographed on flash silica gel using as eluant ethyl acetate:toluene (1:99) to isolate the title compound as the most polar product; m.p. 133° C.

Step B: Methyl 3-[N-methyl-3-(t-butylthio)-6-methoxyinidol-2-yl]-2,2-dimethylpropanoate A solution of 1.75 g of the indole from Step A in 30 mL of THF and 3 mL HMPA was cooled to −78° C. and to this solution was slowly added a solution of 0.54M KHMDS in toluene (10.2 mL). The mixture was stirred at this temperature for 15 min. and treated with 0.34 mL of iodomethane. The mixture was stirred at −78° C. for 5 h, quenched with 1N HCl (100 mL), extracted with ethyl acetate, and the organic layer washed with H₂O, dried over Na₂SO₄ and evaporated to dryness. The residue was chromatographed on flash silica gel using ethyl acetate:hexane (20:80) as eluant to afford the title compound as a solid; m.p. 97°–98° C.

Step C: Methyl 3-[N-methyl-6-hydroxyindol-2-yl]-2,2-dimethyl-propanoate

To a cold solution of 940 mg of the indole ester from Step B and 1.6 mL of ethanethiol in CH₂Cl₂ (50 mL) was added portion-wise 4.3 g of AlCl₃. After complete addition, the mixture was stirred at R.T. for 2 h. The mixture was then cooled to 0° C. and carefully quenched with a solution of 0.5M Na,K tartrate (200 mL) and extracted with CH₂Cl₂. The organic layer was dried over Na₂SO₄ and evaporated to dryness to give a solid which was chromatographed on flash silica gel using ethyl acetate:hexane (30:70) as eluant to afford the title compound; m.p. 125°–126° C.

Step D: Methyl 3-[N-methyl-6-(p-chlorobenzoyloxy)-3-(p-chlorobenzoyl)indol-2-yl]-2,2-dimethylpropanoate To a cold solution of 393 mg of hydroxy indole from Step C in 5 mL of THF were added 0.31 mL of Et₃N followed by 0.21 mL of p-chlorobenzoyl chloride. The mixture was stirred at R.T for 15 min and quenched with H₂O. The mixture was extracted with ethyl acetate which was dried over Na₂SO₄ and evaporated to dryness to give a solid which was dissolved in 10 mL of 1,2-dichloroethane. To this mixture were added successively at R.T. 0.38 mL of p-chlorobenzoyl chloride and 803 mg of AlCl₃. The mixture was heated at 80° C. for 3 h, cooled to R.T. and quenched with 50 mL of 0.5N HCl. The mixture was extracted with CH₂Cl₂, washed with H₂O, dried over Na₂SO₄ and evaporated to dryness. The residue was chromatographed on flash silica gel using ethyl acetate:hexane (20:80) as eluant to afford the title compound as a white solid. m.p. 138° C.

Step E: Methyl 3-[N-methyl-3-(p-chlorobenzoyl)-6-hydroxyindol-2-yl]-2,2-dimethylpropanoate To a suspension of 270 mg of the p-chlorobenzoate from Step D in 3 mL of MeOH was added 1.2 mL of a solution of 1.3M NaOMe in MeOH and the mixture was stirred at R.T. for 2 hr. The reaction mixture was poured onto 25% aq. NH₄OAc and extracted with ethyl acetate. The organic extract was dried over Na₂SO₄, evaporated to dryness and the residue chromatographed on flash silica gel using ethyl acetate:hexane (40:60) as eluant to afford the title compound as a yellow foam.

Step F: Methyl 3-[N-methyl-3-(p-chlorobenzoyl)-6-(quinolin-2-ylmethoxy)indol-2-yl]-2,2-dimethylpropanoate To a solution of 180 mg of the phenol from Step E in 5 mL of DMF were added 124 mg of milled K₂CO₃ followed by 150 mg of 2-(bromomethyl) quinoline. The mixture was stirred at R.T. for 18 h, poured onto 25% aq. NH₄OAc and extracted with ethyl acetate. The extract was dried over Na₂SO₄ and evaporated to dryness to give an oil which was chromatographed on flash silica gel using ethyl acetate:hexane (30:70) as eluant to give the title compound as a foam.

Step G: 3-[N-Methyl-3-(p-chlorobenzoyl)-6-(quinolin-2-ylmethoxy)indol-2-yl]-2,2-dimethylpropanoic acid To a solution of 230 mg of ester from Step F in 1.5 mL of THF and 3 mL of MeOH was added 1M aq. LiOH and the mixture stirred at 80° C. for 4 h. The mixture was cooled to R.T. and evaporated to dryness in vacuo. The residue was dissolved in a mixture of 20 mL of 25% aq. NH₄OAc and 20 mL of ethyl acetate using vigourous stirring. The organic layer was separated, dried over Na₂SO₄ and evaporated to dryness to give a yellow solid (216 mg). This solid was swished for 2 h in 5 mL of a mixture of Et₂O:hexane (1:1). The solid was filtered and rinsed with a 1:2 mixture of Et₂O:hexane to give the title product as a yellow solid, m.p. 203°–205° C.

Anal. C, H, N: Calc. C 70.65; H 5.16; N 5.32; Found C 70.42; H 5.25; N 5.40.

EXAMPLE 25

3-[N-Methyl-3-(p-chlorobenzyl)-6-(quinolin-2-yl-methoxy)indol-2-yl]-2,2-dimethylpropanoic acid, sodium salt hemihydrate

Step A: Methyl 3-[N-methyl-3-(p-chlorobenzyl)-6-(p-chlorobenzoyloxy)indol-2-yl]-2,2-dimethylpropanoate To a solution of 500 mg of the benzoyl derivative from Step D of Example 24 in 10 mL of 1,2-dichloroethane were added 1.19 g of ZnI₂ and 700 mg of NaBH₃CN. The mixture was heated at 65° C. for 5 hours and cooled to R.T. The mixture was quenched with 1N aq. HCl and extracted with CH₂Cl₂. The extracts were washed with brine, dried over Na₂SO₄ and evaporated to dryness to give an oil which was chromatographed on flash silica gel using ethyl acetate:hexane (15:85) as eluant to isolate the title compound as a white foam.

Step B: Methyl
3-[N-methyl-3-(p-chlorobenzyl)-6-hydroxyindol-2-yl]-2,2-dimethylpropanoate To a suspension of 425 mg of p-chlorobenzoate from Step A in 3 mL of MeOH was added 1.9 mL of a solution of 1.3M NaOMe in MeOH. The mixture was stirred at R.T. for 1 h, poured into 20 mL of 25% aq. NH₄OAc, and extracted with ethyl acetate. The organic extract was dried over Na₂SO₄ and evaporated to dryness to give an oil which was chromatographed on flash silica gel using ethyl acetate:hexane (30:70 as eluant to give the title compound as a white foam.

Step C: Methyl
3-[N-methyl-3-(p-chlorobenzyl)-6-(quinolin-2-ylmethoxy)indol-2-yl]-2,2-dimethylpropanoate To a solution of 315 mg of the ester from Step B in 3 mL of DMF were added 225 mg of milled K₂CO₃ and 272 mg of 2-(bromomethyl)quinoline. The mixture was stirred at R.T. for 18 h, poured into 25% aq NH₄OAc, and extracted with ethyl acetate. The organic extract was dried over Na₂SO₄ and evaporated to dryness to give an oil which was chromatographed on flash silica gel using ethyl acetate:hexane (30:70) as eluant to give the title compound as a foam.

Step D:
3-[N-Methyl-3-(p-chlorobenzyl)-6-(quinolin2-ylmethoxy)indol-2-yl]-2,2-dimethyl propanoic acid, sodium salt hemihydrate To a solution of 367 mg of the ester from Step C in 3 mL of THF and 6 mL of MeOH was added 1M aq. LiOH and the mixture was heated at 80° C. for 2 h. The mixture was cooled to R.T. and evaporated to dryness. The residue was dissolved in a mixture of 20 mL of 25% aq. NH₄OAc and 20 mL of ethyl acetate (vigourous stirring required). The organic layer was separated, dried over Na₂SO₄ and evaporated to dryness to give a white solid (346 mg). The solid was swished at R.T. for 2 h with 10 mL of a mixture of Et₂O:hexane (1:1), filtered, rinsed with a mixture of (1:2) Et₂O:hexane and the solid collected to give the title compound as its free acid, a white solid: m.p. 185° C.

The title compound was prepared by dissolving the above acid in 1 mL of EtOH to which 0.63 mL of 1N aq. NaOH was added. The mixture was freeze dried for 2 days to give the title product as a white solid.

Anal. C, H, N: Calc. C 67.32; H 5.29; N 5.07; Found C 67.15; H 5.35; N 5.17.

EXAMPLE 26

3-[N-(4-Chlorobenzyl)-3-i-propoxy-5-(quinolin-2-ylmethoxy)indol-2-yl]-2,2-dimethylpropanoic acid The title compound is prepared according to the method of Example 1, but using methyl 5-i-propoxy2,2-dimethyl-4-oxopentanoate as starting material in Step A in place of methyl 5-t-butylthio-2,2-dimethyl-4-oxopentanoate.

EXAMPLE 27

3-[N-(4-Chlorobenzyl)-3-(t-butylthio)-5-(quinolin-2-ylmethoxy)indol-2-yl]-2-ethylpropanoic acid Step A: Methyl 4-chloro-2-ethyl-4-pentenoate A 2L 3-necked flask equipped with a mechanical stirrer, pressure equalizing addition funnel, and nitrogen inlet was charged with diisopropylamine (28 mL, 200 mmol) and dry THF (400 mL). The mixture was cooled to 0° C. and a 1.6M solution of butyl lithium in hexane (125 mL, 200 mmol) was then added over a 15 minute period and stirring was continued for an additional 45 minutes.

The resultant solution of lithium diisopropylamide (200 mmol) was cooled to −78° C. and then butyric acid (9.1 mL, 100 mmol) was added over a 15 minute period. The reaction was allowed to warm to room temperature (1 hour) and then heated at 55° C. for 3.5 hours. The resultant gel was cooled to −78° C. and then treated 2,3-dichloro-1-propene (10.1 mL, 110 mmol) over a 15 minute period. The mixture was then allowed to warm to room temperature and stirred for 18 hours.

The reaction mixture was diluted with Et₂O (400 mL), extracted with H₂O (400 mL) and with NaOH 1N (300 mL). The aqueous layers were combined, acidified with HCl (2N, until pH 1–2) and the product was extracted with EtOAc (2×300 mL). The organic layers were combined, washed with brine (200 mL) and dried over MgSO₄. Filtration and concentration gave a yellow oil which was dissolved in dry MeOH (150 mL) and acetyl chloride (1 mL) was added dropwise. The resultant solution was gently refluxed for 20 hours. The reaction was allowed to cool to room temperature and it was concentrated. The resultant residue was diluted with Et₂O (600 mL), washed with NaHCO₃ sat. (200 mL), washed with brine (200 mL), and dried over MgSO₄. Filtration and concentration gave a yellow oil which was purified by Kugelrohr distilation (bp 110° C. at 0.2 mm Hg) to give pure (250 MHz NMR) methyl 4-chloro-2-ethyl-4-pentenoate.

Step B: Methyl 5-bromo-2-ethyl-4-oxopentanoate

To a cold (0° C.) solution of methyl 4-chloro-2-ethyl-4-pentenoate from Step 2 (1.67 g, 9.5 mmol) in MeOH (31 ml) and H₂O (16 ml) was added Br₂ dropwise (0.60 mL, 11.6 mmol). The resulting yellow solution was stirred at room temperature for 1 hour. EtOAc (300 mL) and H₂O (200 mL) were added. The organic layer was separated, washed with H₂O, 1N NaOH, H₂O, brine and dried over MgSO₄. Filtration and concentration gave a yellow liquid which was purified by flash chromatography (EtOAc/Hexane (1:9)) to give pure (NMR 250 MHz) methyl 5-bromo-2-ethyl-4-oxopentanoate.

Step C: Methyl 5-(t-butylthio)-2-ethyl-4-oxopentanoate

To a cold (0° C.) stirred solution of the bromoketone from Step 2 (490 mg, 2.07 mmol), in 10 mL of dry THF, were sequentially added 2-methyl-2-propyl thiol (0.30 mL) and triethylamine (0.40 mL, 2.9 mmol). The reaction mixture was then allowed to warm to room temperature. After 18 hours the white solid was removed by filtration and the filtrate was concentrated. The resulting yellow residue was purified by flash chromatography (Et₂O/Hexane (9:50)) to give the pure title compound (250 MHz NMR).

Step D:
3-[N-(4-Chlorobenzyl)-3-(t-butylthio)-5-(quinolin-2-ylmethoxy)indol-2-yl]-2-ethylpropanoic acid The title compound was prepared according to the method of Example 1, but using methyl 5-t-butylthio-2-ethyl-4-oxopentanoate as starting material in Step A in place of methyl 5-t-butylthio-2,2-dimethyl-4-oxopentanoate.

Anal. C, H, N, for sodium salt . 2H₂O: Calc. C 63.30; H 5.94; N 4.34, Found. C 63.29; H 5.87; N 4.37.

The sodium salt of the title compound in this and other Examples was prepared by the method of Example 25.

EXAMPLE 28

3-[N-(4-Chlorobenzyl)-3-trifluoroacetyl-5-(quinolin-2-ylmethoxy)indol-2-yl]-2,2-dimethylpropanoic acid Step A: Methyl 3-[N-(4-chlorobenzyl)-3-trifluoroacetyl-5-hydroxyindol-2-yl]-2,2-dimethylpropanoate Methyl 3-[N-(4-chlorobenzyl)-5-hydroxy indol-2-yl]-2,2-dimethylpropanoate (310 mg) from Example 8 (Step A) was dissolved in 3 ml of 1,2-dichloroethane and the solution charged with 0.6 ml of trifluoroacetic anhydride and 500 mg of AlCl₃. The reaction was stirred at RT, under argon for 4h, then quenched with 20 mL of 0.5N Na, K tartrate solution, extracted with 3×20 ml of Et₂O, washed with 10 mL of H₂O and dried over MgSO₄. Removal of solvent provided an oily residue which was chromatographed on silica gel to give the title compound.

Step B:
3-[N-(4-Chlorobenzyl)-3-trifluoroacetyl-5-(quinolin-2-ylmethoxy)indol-2-yl]-2,2-dimethylpropanoic acid The title compound was prepared using the conditions described in Step D and Step E of Example 1, but substituting the ester from Step A for the ester of Example 1, Step C.

Anal. C, H, N for sodium salt . 7H₂O Calc. C 51.72; H 5.29; N 3.76, Found. C 51.81; H 5.19; N 3.73.

EXAMPLE 29

3-[N-(4-Chlorobenzyl-3-(3,3-dimethyl-1-oxo-1-butyl)-5-(quinolin-2-ylmethoxy)indol-2-yl]-2-methylpropanoic acid Step A: Methyl 5-(t-butylthio)-2-methyl-4-oxopentanoate The title compound was prepared according to the method described in Example 27, but using propionic acid as starting material in Step A in place of butyric acid.

Step B:
3-[N-(4-Chlorobenzyl)-3-(3,3-dimethyl-1-oxo-1-butyl)-5-(quinolin-2-ylmethoxy)indol-2-yl]-2-methylpropanoic acid The title compound was prepared according to the method described in Example 11, but substituting 5-t-butylthio-2-methyl-4-oxopentanoate as starting material in Example 1 Step A in place of methyl 5-t-butylthio-2,2-dimethyl-4-oxopentanoate.

Anal C, H, N, for sodium salt . 1.5 H₂O Calc. C 66.50; H 5.90; N 4.43, Found. C 66.58; H 5.87; N 4.40.

EXAMPLE 30

3-[3-(3,3-Dimethyl-1-oxo-1-butyl-5-(quinolin-2-ylmethoxy)indol-2-yl]-2,2-dimethylpropanoic acid Step A: Methyl 3-[3-(t-butylthio)-5-methoxy indol-2-yl]-2,2-dimethylpropanoate A mixture containing 4-methoxyphenyl hydrazine . HCl (70.66 g, 0.405 mol) and methyl 5-(t-butylthio)-2,2-dimethyl-4-oxopentanoate (99.54 g, 0.405 mol) in ᵗBuOH (400 ml) was heated at a gentle reflux for 48 hours. The mixture was allowed to cool to RT and the precipitated NH₄Cl was removed by filtration. The residue was concentrated and fractionated on a plug of silica using EtOAc/hexane (1:3) as eluent. Evaporation of the appropriate fraction gave an orange-brown solid which was crystallized from EtOH (100 ml). Yield from two crops afforded 55.6g of the title compound.

1H NMR (CD₃COCD₃): δ1.20(s, 6H); 1.25 (s, 9H) 3.33 (s, 2H); 3.62 (s, 3H); 3.81 ppm (s, 3H); in addition to aromatic protons.

Step B: Methyl 3-[5-hydroxyindol-2-yl]-2,2-dimethylpropanoate

To a solution of the compound from step A (25.50 g, 73 mmol) in CH₂Cl₂ (250 ml) at 0° C. was added AlCl₃ (87.70 g, 9 mol eq.) portion-wise. When the addition was complete, the ice-bath was removed and the mixture was stirred at RT for 3 hours. EtSH (27 ml, 5 mol eq.) was added and the resulting mixture was stirred for a further 5 hours. It was then slowly poured onto an ice-cold 1M solution of Na, K tartrate. The product was extracted into CH₂Cl₂ (×2) and the organic phase was washed with aq. NaCl (×3). Conventional work-up followed chromatography on silica gel using EtOAc/hexane 1:5 to 3:2 afforded 13.60 g of the title compound, 75% yield.

1H NM (CDCl₃): δ1.26 (s, 6H); 2.95 (s, 2H); 3.72 (s, 3H); 6.11 (s, 1H); 6.71 (bd, 1H); 6.95 (s, 1H); 7.16 (d, 1H); 7.26 ppm (s, 1H).

Step C: Methyl 3-[5-(quinolin-2-ylmethoxy)-indol-2-yl]-2,2-dimethylpropanoate

A mixture of the phenol from step B (13.62 g, 55.14 mmol) and 2-bromomethylquinoline (12.85 g, 1.05 mol eq.) and anhydrous K₂CO₃ (15.22 g, 2 mol. eq.) in DMF (40 ml) was stirred at RT for 48 hours. The mixture was then poured onto ice/water and after all the ice had melted, the brown solid was collected and air-dried. The dried material was passed through a plug of silica (using EtOAc/hexane (1:3) as eluent) to remove the color; yield: 19 g, 88%. Recrystallization from EtOH afforded 14.17g of pure title compound, m.p. 131°-132° C.

Step D: Methyl 3-[3-(3,3-dimethyl-1-oxo-1-butyl)-5-(quinolin-2-ylmethoxy)indol-2-yl]-2,2-dimethyl-propanoate To a suspension of AlCl3 (5.7 g, 42 mmol) in CH₂Cl₂ (30 mL) at 0° C. was added 3,3-dimethylbutanoyl chloride (2.4 mL, 17 mmol). After 15 minutes at 0° C., a solution of the ester from step C (3.0 g, 7.7 mmol) in CH₂Cl₂ (10 mL) was added by double-tipped needle. The mixture was stirred a further 20 minutes, at which point it was poured into a mixture of 0.5M Na, K tartrate (150 mL) and ice (100 g). The product was extracted with EtOAc, and the organic layer was washed successively with 0.5M NaK tartrate, H₂O, and brine. The solvent was then removed and yellow/orange oil (3.5 g) was used without purification in the following step.

Step E:
3-[3-(3,3-Dimethyl-1-oxo-1-butyl)-5-(quinolin-2-ylmethoxy)indol-2-yl]-2,2-dimethylpropanoic acid The crude ester from step D was dissolved in a mixture of MeOH (20 mL), THF (20 mL), and H₂O (5 mL). To this was added 10M NaOH (2.3 mL, 23 mmol). After stirring for 3 hours, the solution was cooled to 0° C., and HOAc (1.5 mL) was added dropwise. The solution was partly concentrated to remove the THF and MeOH, and the product was then extracted into EtOAc. The organic layer was washed with H₂O and brine. After drying (MgSO₄), the solution was filtered and evaporated to give a pale orange solid. The product was stirred vigourously with a mixture of isopropanol (30 ml) and H₂O (3 mL) to give the title compound as an off-white amourphous solid (2.6 g). mp=193°-196° C. (dec)

EXAMPLE 31

3-[N-(4-Triflouromethylbenzyl)-3-(3,3-dimethyl-1-oxo-1-butyl)-5-(quinolin-2-yl-methoxy)indol-2-yl]-2,2-dimethylpropanoic acid The product from Example 30 (100 mg, 0.21 mmol) and 4-trifluoromethylbenzyl bromide (98 mg, 0.41 mmol), and methyltrioctylammonium chloride (83 mg. 0.21 mmol) were dissolved in a mixture of 50% NaOH (2 mL) and benzene (0.5 mL). After vigourous stirring for 3.5 hours, the reaction mixture was cooled to 0° C. and was acidified with HOAc (2 mL). The product was extracted with EtOAc, and the organic layer was washed with H₂O and brine. Following evaporation of the solvent, the residue was purified by flash chromatography on silica gel, eluting with 1:5 EtOAc/hexane containing 1% HOAc. The resulting yellow foam was triturated with 1:4 Et₂O/hexane to give the title compound as a pale yellow solid (37 mg, 28%).

¹H NMR (CDCl₃) δ8.22 (1H, d, J=8.5 Hz), 8.13 (1H, d, J=8.5 Hz), 7.87-7.70 (3H, m), 7.62-7.45 (4H, m), 7.00-6.85 (4H, m), 5.45 (4H, s), 3.58 (2H, brs), 2.87 (2H, s), 1.30 (6H, s), 1.03 ppm (9H, s).

EXAMPLE 32

3-[N-Benzyl-3-(3,3-dimethyl-1-oxo-1-butyl)-5-(quinolin-2-ylmethoxy)indol-2-yl]-2,2-dimethylpropanoic acid Following the method of Example 31, with benzyl bromide as the alkylating agent, the title compound was obtained as an off-white solid (mp=180°-183 ° C. (dec)).

EXAMPLE 33

3-[N-(3-Methoxybenzyl)-3-(3,3-dimethyl-1-oxo-1-butyl)-5-(quinolin-2-ylmethoxy)indol-2-yl]-2,2-dimethylpropanoic acid Following the method of example 31, with 3-methoxybenzyl bromide as the alkylating agent, the title compound was obtained as an off-white solid. (mp=173°-175 ° C. (dec)).

EXAMPLE 34

3-[N-Allyl-3-(3,3-dimethyl-1-oxo-1-butyl)-5-(quinolin-2-ylmethoxy)indol-2-yl]-2,2-dimethylpropanoic acid Step A: Allyl 3-[N-allyl-3-(3,3-dimethyl-1-oxo-1-butyl)-5-(quinolin-2-ylmethoxy)indol-2-yl]-2,2-dimethylpropanoate To a solution of the product from Example 30 (100 mg, 0.21 mmol) in dry DMF 2 mL) was added 80% NaH (14 mg, 0.47 mmol), followed 15 minutes later by allyl bromide (0.35 mL, 4 mmol). After 2½ hours, saturated NH₄Cl solution was added, and the product was extracted with EtOAC. The organic layer was washed with H₂O and brine, dried over MgSO₄, filtered and was then evaporated to give the title compound as a yellow oil which was used as such in the next step.

Step B:
3-[N-Allyl-3-(3,3-dimethyl-1-oxo-1-butyl)-5-(quinolin-2-ylmethoxy)indol-2-yl]-2,2-dimethylpropanoic acid The crude ester from step 1 was treated as in the method of Example 30, Step 2 to give the title compound as an off-white solid (mp=146°-148° C. (dec)).

EXAMPLE 35

3-[N-(4-Methoxybenzyl)-3-(3,3-dimethyl-1-oxo-1-butyl)-5-(quinolin-2-ylmethoxy)indol-2-yl]-2,2-dimethylpropanoic acid Following the method of Example 34, with 4 methoxybenzyl chloride as the alkylating agent, the title compound was obtained as a white solid.

¹H NMR (250 MHz, acetone-d₆) δ1.05 (9H, s), 1.27 (6H, s) 2.38 (2H, s), 3.73(3H, s), 3.78 (2H, s) 5.46(2H, s), 5.48(2H, s), 6.70-8.40 ppm (13H, aromatics).

EXAMPLE 36

3-[N-Methyl-3-(3,3-dimethyl-1-oxo-1-butyl)-5-(quinolin-2-ylmethoxy)indol-2-yl]-2,2-dimethylpropanoic acid Following the method of Example 34, with methyl iodide as the alkylating agent, the title compound was obtained as a white solid.

Anal C, H, N for sodium salt . 1 H₂O Calc. C 68.42; H 6.70; N 5.32, Found. C 68.36; H 6.81; N 5.44.

EXAMPLE 37

3-[3-(4-Chlorobenzyl)-6-(quinolin-2-ylmethoxy)indol-2-yl]-2,2-dimethylpropanoic acid Step A: 3-(Quinolin-2-ylmethoxy)phenylhydrazine The title compound was prepared using the conditions described in Step A, Step B and Step C of Example 1A, but replacing the phenol in Step A with 3-acetamidophenol; m.p. 55°-70° C. (dec).

Step B: Ethyl (4-chlorobenzene)propanoate

A solution of 4-chlorobenzaldehyde (28 g) and (carboethoxymethylene)triphenylphosphorane (73 g) in toluene (500 mL) was refluxed for 2 hours. The reaction was cooled to room temperature and concentrated under vacuum to a total volume of 150 mL. Then pure hexane (500 mL) was added and the mixture was left for 18 hours at room temperature. The solid (triphexylphosphine oxide) was filtered, rinsed with hexane and the filtrate evaporated to give crude product which was distilled at 0.5 mm Hg, and the fraction boiling at 130° C. was collected to give ethyl 4-chlorocinnamate, which was reduced as follows: the cinnamate (21 g) was hydrogenated in EtoAc (300 mL) in the presence of 5% Pd on C (2 g) for 3 hours at atmospheric pressure. After completion, the reaction mixture was filtered through a celite pad, rinsed with EtOAc and the filtrate evaporated to dryness to give the title product as an oil.

Step C: Methyl 6-(4-chlorophenyl)-2,2-dimethyl-4-oxohexanoate

To a solution of ethyl (4-chlorobenzene)propanoate (Step B, 10 g) in dry THF (500 mL) at −78° C. was added 0.58M potassium hexamethyldisilazane in toluene (243 mL). The mixture was stirred at −60° C. for one hour. Then a solution of 2,2-dimethylsuccinic anhydride (6 g) in THF (100 mL) was added slowly and the mixture was slowly warmed to room temperature and finally stirred for 18 hours. Water (1000 mL) was added and the organic layer separated. The aqueous layer was washed with EtOAc (3×250 ml) and acidified with 1N HCl. The aqueous layer was extracted with EtOAc, the extract was dried (Na$_2$SO$_4$) and evaporated to give a residue which was dissolved in THF (100 mL) and MeOH (200 mL) and treated at reflux with 1N LiOH (100 mL) for 4 hours. The mixture was cooled to room temperature and concentrated under vacuum until H$_2$O distilled off. Water (500 mL) was added, the mixture acidified with 1N aq. HCl, extracted with EtOAc, the extract was dried (Na$_2$SO$_4$) and evaporated to give the title product as its carboxylic acid. The compound was treated with diazomethane in ether, evaporated to dryness and chromatographed over silica gel, eluting with EtOAc-hexane (10:90) to give the title product as a white solid; m.p. 52°–54° C.

Step D: Methyl 3-[3-(4-chlorobenzyl)-6-(quinolin-2-ylmethoxy)indol-2-yl]-2,2-dimethylpropanoate To a solution of methyl 6-(4-chlorophenyl)-2,2-dimethyl-4-oxohexanoate (Step C, 2.8 g) in toluene (30 mL) and glacial HOAc (15 mL) was added portion-wise solid 3-(quinolin-2-ylmethoxy)phenylhydrazine (Step A, 3.2 g) and stirred at room temperature for 2 hours. The reaction mixture was diluted with Et$_2$O (200 mL), washed with 1N NaOH, H$_2$O, dried (Na$_2$SO$_4$) and evaporated to give crude hydrazone which was immediately treated as follows: the crude hydrazone was dissolved in a mixture of PPE(15 mL) and 1,2-dichloroethane (30 mL) and stirred at 40° C. for 18 hours. The reaction mixture was cooled to 0° C. and carefully treated with 1N NaOH to bring to pH 9. The mixture was then extracted with ether, the extract was washed with H$_2$O, dried (Na$_2$SO$_4$) and evaporated to give a residue, which was chromatographed in a column of flash silica gel (eluting with EtOAc-hexane 25:75) and isolating the most polar component as the title product as a foam.

Step E: 3-[3-(4-Chlorobenzyl)-6-(quinolin-2-ylmethoxy)indol-2-yl]-2,2-dimethylpropanoic acid The title compound was prepared using the conditions described in Step B of Example 1, but substituting the ester from Step D for the ester of Example 1, Step A.

Anal C, H, N for sodium salt . 1½ H$_2$O Calc. C 65.75; H 5.33; N 5.11, Found. C 66.08; H 5.31; N 5.08.

EXAMPLE 38

3-[N-(Phenylsulfonyl)-3-(4-chlorobenzyl)-6-(quinolin-2-ylmethoxy)indol-2-yl]-2,2-dimethylpropanoic acid

Step A: Methyl 3-[N-(phenylsulfonyl)-3-(4-chlorobenzyl)-6-(quinolin-2-ylmethoxy)indol-2-yl]-2,2-dimethylpropanoate To a solution of methyl 3-[3-(4-chlorobenzyl)-6-(quinolin-2-ylmethoxy)indol-2-yl]-2,2-dimethylpropanoate (Step D, Example 37) (208 mg) in dry THF (5 mL) and HMPA (0.5 mL) at −78° C. was added 0.58M potassium hexamethyldisilazane in toluene (0.77 mL) and the solution then stirred at −78° C. for 15 minutes. Then freshly distilled benzenesulfonyl chloride (0.062 mL) was added and stirred at −78° C. for 2.5 hours. The reaction mixture was quenched with 25% aq. NH$_4$OAc, extracted with EtOAc, dried over Na$_2$SO$_4$ and evaporated to give crude product. Chromatography of the residue in a column of flash silica gel (eluting with EtOAc-hexane 25:75) afforded the title product as an oil.

Step B: 3-[N-Phenylsulfonyl)-(3-(4-chlorobenzyl)-6-(quinolin-2-ylmethoxy)indol-2-yl]-2,2-dimethyl propanoic acid The title compound was prepared under the conditions described in Step B of Example 1, but substituting the ester from Step A for the ester of Example 1, Step A.

Anal. C, H, N for sodium salt. Calc. C 67.65; H 4.89; N 4.38, Found. C 68.07; H 5.18; N 4.32.

EXAMPLE 39

3-[N-Benzyl-3-(4-chlorobenzyl)-6-(quinolin-2-ylmethoxy)indol-2-yl]-2,2-dimethylpropanoic acid The title compound was prepared under the conditions described in Step A and Step B of Example 38, but substituting benzyl chloride for the benzenesulfonyl chloride from Example 38 (Step A).

Anal. C, H, N for sodium salt . ½ H$_2$O Calc. C 71.66; H 5.36; N 4.52, Found. C 71.65; H 5.49; N 4.44.

EXAMPLES 40 AND 41

3-[N-(4-Chlorobenzyl)-3-(t-butylsulfonyl)-5-(quinolin-2-ylmethoxy)indol-2-yl]-2,2-dimethylpropanoic acid
and
3-[N-(4-chlorobenzyl)-3-(t-butylsulfinyl)-5-(quinolin-2-ylmethoxy)indol-2-yl]-2,2-dimethylpropanoic acid The title compounds were prepared using the conditions described for Examples 6 and 7, but substituting the ester of Example 4 (Step D) for the ester of Example 1 (Step D).

3-[N-(4-chlorobenzyl)-3-(t-butylsulfonyl)-5-(quinolin-2-ylmethoxy)indol-2-yl]-2,2-dimethylpropanoic acid Anal. C, H, N for sodium salt . 1½ H$_2$O Calc. C 61.12; H 5.58; N 4:19, Found C 61.31; H 5.39; N 4.19.

3-[N-(4-chlorbenzyl)-3-(t-butylsulfinyl)-5-(quinolin-2-ylmethoxy)indol-2-yl]-2,2-dimethylpropanoic acid Anal. C, H, N for sodium salt . 2 H$_2$O Calc. C 61.76; H 5.79; N 4.24, Found C 61.44; H 5.68; N 4.19.

EXAMPLE 42

3-[N-Allyl-3-(4-chlorobenzyl)-6-(quinolin-2-ylmethoxy)-indol-2-yl]-2,2-dimethylpropanoic acid The title compound was prepared under the conditions described in Step A and Step B of Example 38, but substituting allyl bromide for the benzenesulfonyl chloride from Example 38 (Step A).

Anal. C, H, N for sodium salt . 2 H$_2$O Calc. C 66.38; H 5.74; N 4.69, Found C 66.57; H 5.75; N 4.73.

EXAMPLE 43

3-[N-(n-Propyl)-3-(4-chlorobenzyl)-6-(quinoline-2-ylmethoxy)indol-2-yl]-2,2-dimethylpropanoic acid A solution of methyl 3-[N-allyl-3-(4-chlorobenzyl)-6-(quinolin-2-ylmethoxy)indol-2-yl]-2,2-dimethylpropanoate (Example 42, methyl ester) (190 mg) was hydrogenated in EtOAc (4 mL) in the presence of 5% Pd on charcoal at atmospheric pressure for 1 hour. Filtration on Celite pad and evaporation of liquors afforded the methyl ester of the title product. Hydrolysis of this ester under the conditions described in Step B of Example 1 provided the title compound.

Anal. C, H, N for sodium salt . 1½ H$_2$O Calc. C 67.17; H 5.98; N 4.75, Found C 67.38; H 5.44; N 4.85.

EXAMPLE 44

3-[N-Ethyl-3-(4-chlorobenzyl)-6-(quinolin-2-ylmethoxy)-indol-2-yl]-2,2-dimethylpropanoic acid The title product was prepared under the conditions described in Step A and Step B of Example 38, but substituting iodoethane for the benzenesulfonyl chloride from Example 38 (Step A).

Anal C, H, N for sodium salt . 2 H$_2$O Calc. C 65.69; H 5.86 N 4.79, Found C 65.81; H 5.21; N 4.77.

EXAMPLE 45

3-[N-(4-Chlorobenzyl)-3-(4-t-butylbenzoyl)-5-quinolin-2-yl-methoxy)indol-2-yl]-2,2-dimethylpropanoic acid The title compound was prepared according to the method described in Example 9, but using 4-t-butylbenzoyl chloride in place of benzoyl chloride in Step A.

Anal. C, H, N, for sodium salt . 2½ H$_2$O Calc. C 67.81; H 5.97; N 3.86, Found. C 67.91; H 6.01; N 3.64.

EXAMPLE 46

3-[N-(4-chlorobenzyl)-3-(4-chlorobenzoyl)-5-(quinolin-2-ylmethoxy)indol-2-yl]-2,2-dimethylpropanoic acid The title compound was prepared according to the method described in Example 9, but using 4-chlorobenzoyl chloride in place of benzoyl chloride in Step A.

Anal. C, H, N for sodium salt . 2 H$_2$O Calc. C 63.89; H 4.78; N 4.03; Found C 64.20; H 4.61; N 3.99.

EXAMPLE 47

3-[N-(4-Chlorobenzyl)-3-(1,1-dimethylethyl)-5-(quinolin-2-ylmethoxy)indol-2-yl]-2,2-dimethylpropanoic acid Step A: Methyl 3-[N-(4-chlorobenzyl)-5-(quinolin-2-ylmethoxy)indol-2-yl]-2,2-dimethylpropanoate Methyl 3-[N-(4-chlorobenzyl)-3-(t-butylthio)-5-(quinolin-2-ylmethoxy)indol-2-yl]-2,2-dimethylpropanoate (3.77 g, 6.27 mmol) from Step D of Example 1, was dissolved in 75 mL of dry CH$_2$Cl$_2$ and the solution was charged with 6.27 g (47.0 mmol) of AlCl$_3$ and the mixture was stirred at RT, under Ar, for 1.75 hours. The reaction was then quenched by the addition of 0.5N Na, K tartrate (150 mL) and the resulting mixture was extracted with EtOAc (3×). The organic extracts were washed with 0.5N Na, K tartrate (1×) and with brine (1×), and dried (MgSO$_4$). Filtration and removal of solvents provided a brown oily residue which was chromatographed on silica gel using EtOAc-hexane (1:3) to give the title compound.

Step B: Methyl 3-[N-(4-chlorobenzyl)-3-(1,1-dimethylethyl)-5-(quinolin-2-ylmethoxy)-indol-2-yl]-2,2-dimethylpropanoate Trimethylacetyl chloride (4.23 g, 4.32 mL, 35.09 mmol) was added to a cold suspension (0° C.) of AlCl$_3$ (11.7 g, 87.7 mmol) in dry CH$_2$Cl$_2$ (60 mL) under Ar. The yellow mixture was stirred at 0° C. for 15 minutes, and a solution of 9.00 g (17.54 mmol) of methyl 3-[N-(4-chlorobenzyl)-5-(quinolin-2-ylmethoxy)indol-2-yl]-2,2-dimethylpropanoate (prepared in Step A) in CH$_2$Cl$_2$ (40 mL) was added dropwise (over 10 minutes) at 0° C. The reaction mixture was stirred for 10 minutes and slowly poured onto an ice-cold and vigourously stirred mixture of 0.5M aqueous Na, K tartrate (500 mL) and EtOAc (400 mL). After 20 minutes, the aqueous layer was extracted with EtOAc (2×) and the combined organic extracts were washed with H$_2$O (2×), with 1N aqueous NaOH (2×), with H$_2$O (2×) and dried (MgSO$_4$). Filtration and removal of solvents provided a yellow oily residue which was chromatographed on silica gel using EtOAc-hexane (1:4) to give the title compound.

Step C: 3-[N-(4-chlorobenzyl)-3-(1,1-dimethylethyl)-5-(quinolin-2-ylmethoxy)indol-2-yl]-2,2-dimethylpropanoic acid The title compound was prepared according to the conditions described in Step B of Example 1, but substituting the ester from Step B for the ester of Example 1. The title compound was recrystallized from EtOAc-EtOH; m.p. 201°–202° C.

Anal. Calc. C 73.57 H 6.36 N 5.05, Found C 73.75 H 6.37 N 5.03.

EXAMPLE 48

3-[N-(4-Chlorobenzyl)-3-acetyl-5-(quinolin-2-ylmethoxy)indol-2-yl]-2,2-dimethylpropanoic acid The title compound was prepared according to the conditions described in Step B and Step C of Example 47, from methyl 3-[N-(4-chlorobenzyl)-5-(quinolin-2-ylmethoxy)indol-2-yl]-2,2-dimethylpropanoate (prepared in Step A of Example 47) but using acetyl chloride in place of trimethylacetyl chloride in Step B.

$^1$H NMR (CD$_3$COCD$_3$) δ1.20 (6H, s), 2.64 (3H,s), 3.62 (2H, br s), 5.47 (2H, s) 5.57 (2H, s), 6.90–6.99 (3H, m), 7.28–7.37 (3H, m), 7.56–7.83 (4H, m), 7.97 (1H, d) 8.05 (1H, d), 8.39 ppm (1H,d).

EXAMPLE 49

3-[N-(4-Chlorobenzyl)-3-cyclopropanecarbonyl-5-(quinolin-2-ylmethoxy)indol-2-yl]-2,2-dimethylpropanoic acid The title compound was prepared according to the conditions described in Step B and Step C of Example 47, from methyl 3-[N-(4-chlorobenzyl)-5-(quinolin-2-ylmethoxy)indol-2-yl]-2,2-dimethylpropanoate (prepared in Step A of Example 47), but using cyclopropanecarbonyl chloride in place of trimethylacetyl chloride in Step B.

Anal. C, H, N for sodium salt . 1 H₂O: Calc. C 67.27; H 5.31; N 4.61, Found C 67.27; H 5.16; N. 4.58.

EXAMPLE 50

3-[N-(4-Chlorobenzyl)-3-(3-cyclopentylpropanoyl)-5-(quinolin-2-ylmethoxy)indol-2-yl]-2,2-dimethylpropanoic acid The title compound was prepared according to the conditions described in Step B and Step C of Example 47, from methyl 3-[N-(4-chlorobenzyl)-5-(quinolin-2-ylmethoxy)indol-2-yl]-2,2-dimethylpropanoate (prepared in Step A of Example 47), but using 3-cyclopentylpropanoyl chloride in place of trimethylacetyl chloride in Step B.

¹H NMR (CD₃COCD₃) δ1.09 (2H, m) 1.22 6H, s), 1.40-1.91 (9H, m), 2.94 (2H, t), 3.68 (2H, br s), 5.46(2H, s), 5.58 (2H, s), 6.91-6.99 (3H, m), 7.30(3H, m), 7.53-7.63 (2H, m) 7.72-7.82 (2H, m), 7.96 (1H, d), 8.06 (1H, d), 8.34 ppm, (1h, d).

EXAMPLE 51

3-[N-(4-Chlorobenzyl)-3-(3-methylbutanoyl)-5-(quinolin-2-yl-methoxy)indol-2-yl]-2,2-dimethylpropanoic acid The title compound was prepared according to the conditions described in Step B and Step C of Example 47, from methyl 3-[N-(4-chlorobenzyl)-5-(quinolin-2-ylmethoxy)indol-2-yl]-2,2-dimethyl propanoate (prepared in Step A of Example 47), but using 3-methylbutanoyl chloride in place of trimethylacetyl chloride in Step B.

¹H NMR (CD₃COCD₃): δ0.98 (6H, d), 1.24 (6H, s), 2.30 (1H, m), 2.85 (2H, d), 3.70 (2H, br s), 5.46 (2H, s), 5.58 (2H, s), 6.96 (3H, m), 7.30 (3H, m), 7.55-7.63 (2H, m), 7.73-7.82 (2H, m), 7.95 (1H, d), 8.07 (1H, d), 8.36 ppm (1H, d).

EXAMPLE 52

3-[N-(4-Chlorobenzyl)-3-propanol-5-(quinolin-2-ylmethoxy)indol-2-yl]-2,2-dimethylpropanoic acid The title compound was prepared according to the conditions described in Step B and Step C of Example 47, from methyl 3-[N-(4-chlorobenzyl)-5-(quinolin-2-ylmethoxy)indol-2-yl]-2,2-dimethylpropanoate (prepared in Step A of Example 47), but using propanoyl chloride in place of trimethylacetyl chloride in Step B.

Anal. C, H, N for sodium salt . 1H₂O Calc. C 66.61; H 5.42; N 4.71, Found C 66.87; H 5.45; N 4.69.

EXAMPLE 53

3-[N-(4-Chlorobenzyl)-3-(2-methylpropanoyl)-5-(quinolin-2-ylmethoxy)indol-2-yl]-2,2-dimethylpropanoic acid The title compound was prepared according to the conditions described in Step B and Step C of Example 47, from methyl 3-[N-(4-chlorobenzyl)-5-(quinolin-2-ylmethoxy)indol-2-yl]-2,2-dimethylpropanoate (prepared in Step A of Example 47), but using 2-methylpropanoyl chloride in place of trimethylacetyl chloride in Step B.

¹H-NMR (CD₃COCD₃): δ1.07 (6H, d), 1.16 6H, s), 3.34 (1H, m), 3.64 (2H, br s), 5.46 (2H, s), 5.57 (2H, s), 6.95 (3H, m), 7.32 (3H, m), 7.45 (1H, br s), 7.60 (1H, br t), 7.71-7.83 (2H, m), 7.97 (1H, d), 8.07 (1H, d), 8.36 ppm (1H, d).

EXAMPLE 54

3-[N-(4-Chlorobenzyl)-3-trimethylacetyl-5-(quinolin-2-ylmethoxy)indol-2-yl]-2,2-dimethylpropanoic acid, sodium salt Step A: Methyl 3-[N-(4-chlorobenzyl)-3-trimethylacetyl-5-(quinolin-2-ylmethoxy)indol-2-yl]-2,2-dimethylpropanoate

Method A

The indole from Example 47, Step A (2.00 g, 3.9 mmol) and trimethylacetyl chloride (0.86 g, 7.1 mmol) were dissolved in sieve-dried CH₂Cl₂ (15 mL). The mixture was cooled to −25° C. and AlCl₃ (1.64 g, 12.3 mmol) was added in two portions 5 minutes apart. After 10 minutes at −20° to −25° C., 7 mL of 2.5M aqueous HOAc was added to the mixture such that the temperature stayed below −20° C. The mixture was then warmed to RT and the layers were separated. The organic layer was washed with H₂O, saturated aqueous NaHCO₃, and H₂O, and then evaporated to dryness. The resulting oil was crystalized from MeOH (20 mL) to give 1.4 g (60%) of the title compound.

Method B

A solution of TiCl₄ (6 mL of a 1.0M solution in CH₂Cl₂, 6.0 mmol) and trimethylacetyl chloride (0.491 g, 4.1 mmol) was cooled to −5° C. To the cooled solution was added a solution of the indole from Example 47, Step A (1.025 g, 2.0 mmol) in 2 mL of CH₂Cl₂ over a 5 minute period. After 30 minutes, the reaction was quenched by the addition of 3 mL of 2.5M aqueous HOAc. The mixture was warmed to RT and the layers separated. The organic layer was washed with H₂O, saturated aqeuous NaHCO₃, and H₂O, and then evaporated to dryness. The residual oil was crystallized from 10 mL of MeOH to give 625 mg (53%) of the title compound.

¹H-NMR (CDCl₃) δ1.22 (6H, s), 1.30 (9H, s , 3.29 (2H, s), 3.61 (3H, s), 5.28 (2H, s), 5.47 (2H, s), 6.7-8.2 ppm (13H, m).

IR(Nujol mull) 1636, 1730 cm−1.

Step B

3-[N-(4-Chlorobenzyl)-3-trimethylacetyl-5-(quinolin-2-ylmethoxy)indol-2-yl]-2,2-dimethylpropanoic acid, sodium salt The acylated methyl ester from Step A (401 mg, 0.67 mmol), absolute EtOH (1.62 g), and NaOH (64.2 mg of a 50.9% aq. solution, 0.82 mmol) were refluxed 42 hours. During the latter stages of the reaction, product crystallized. At the end of the reflux, the product was filtered and washed with EtOH to give 288 mg (74%) orange solid. The material was slurried in 3 mL EtOH for 8 hours at RT to give 190 mg of the title compound as a pale orange solid.

¹H-NMR (CD₃OD) δ1.08 (6H, s), 1.15 (9H, s), 3.23 (2H, s), 5.40 (2H, s), 5.55 (2H, s), 6.7-8.2 ppm (13H, m). IR (Nujol mull) 1680, 1575 cm−1.

EXAMPLE 55

3-[N-(4-Chlorobenzyl)-3-phenylacetyl-5-(quinolin-2-yl methoxy)indol-2-yl]-2,2-dimethylpropanoic acid The title compound was prepared according to the conditions described in Step B and Step C of Example 47, from methyl 3-[N-(4-chlorobenzyl)-5-(quinolin-2-ylmethoxy)indol-2-yl]-2,2-dimethylpropanoate (prepared in Step A of Example 47), but using phenylacetyl chloride in place of trimethylacetyl chloride in Step B.

Anal. C, H, N for sodium salt . 1H$_2$O Calc. C 69.46; H 5.22; N 4.26, Found C 69.71; H 5.25; N 4.11.

EXAMPLE 56

3-[N-(4-Fluorobenzyl)-3-(3,3-dimethyl-1-oxo-1-butyl)-5-(quinolin-2-ylmethoxy)indol-2-yl]-2,2-dimethylpropanoic acid Using the procedure of Example 31, but replacing 4-trifluoromethylbenzyl bromide with 4-fluorobenzyl bromide, the title compound is obtained.

EXAMPLE 57

3-[N-(4-Bromobenzyl)-3-(3,3-dimethyl-1-oxo-1-butyl)-5-(quinolin-2-ylmethoxy)indol-2-yl]-2,2-dimethylpropanoic acid Using the procedure of Example 31, but replacing 4-trifluoromethylbenzyl bromide with 4-bromobenzyl bromide, the title compound is obtained.

EXAMPLE 58

3-[N-(4-Iodobenzyl)-3-(3,3-dimethyl-1-oxo-1-butyl)-5-(quinolin-2-ylmethoxy)indol-2-yl]-2,2-dimethylpropanoic acid Using the procedure of Example 31, but replacing 4-trifluoromethylbenzyl bromide with 4-iodobenzyl bromide, the title compound is obtained.

EXAMPLES 59-72

Operating as described in the previous examples, the following compounds are prepared:

(0.80 mL, 5.7 mmol) in THF (5 mL) was added a 1.6M solution of butyllithium in hexane (3.4 mL, 5.4 mmol) over a 5 minute period and stirring was continued for an additional 45 min. Then a solution of methyl 4-chloro-2-ethyl-4-pentenoate (800 mg, 5 mmol) from Example 27, Step A, in THF (2 mL) was added and the reaction was stirred at 0° C. for another 30 minutes. Then ethyl iodide (440 µL, 5.5 mmol) was added and the reaction was allowed to proceed at room temperature for 2 hours. The reaction was quenched with NH$_4$OAc buffer (50 mL of 25% w/v) and extracted with EtOAc. The organic layer was separated, dried over MgSO$_4$, filtered and concentrated. The crude product was purified by Kugelrohr distillation (b.p. 120° C. at 0.1 mm Hg) to give the title compound.

Step B: Methyl 5-(t-butylthio)-2,2-diethyl-4-oxopentanoate

The title compound was prepared according to the method of Example 27, Step B and Step C, but using methyl 4-chloro-2,2-diethyl-4-pentenoate as starting material in Step B in place of methyl 4-chloro-2-ethyl-4-pentenoate.

Step C: Methyl 3-[N-(4-chlorobenzyl)-3-(t-butylthio)-5-(quinolin-2-ylmethoxy)indol-2-yl]-2,2-diethylpropanoate To a mixture of 1-(4-chlorobenzyl)-1-[4-(quinolin-2-ylmethoxy)phenyl]hydrazine from Example 1A, Step D, (660 mg, 1.7 mmol) and anhydrous NaOAc (160 mg, 1.95 mmol) in toluene (3 mL) was added glacial HOAc (1.5 mL). After 30 minutes, a solution containing methyl 5-(t-butylthio)-2,2-diethyl-4-oxopentanoate from Step B (402 mg, 1.47 mmol) in toluene (1 mL) was added and the reaction mixture stirred for 24 hours at room temperature and for 48 hours at 65° C. The reaction was then diluted with EtOAc, washed with NH$_4$OAc buffer (25% w/v) and dried over MgSO$_4$. Filtration and concentration gave a viscous oil which was purified by flash chromatography on silica gel (eluant: EtOAc-hexane 15:85) to give the title compound.

$^1$H NMR (250 MHz acetone-d$_6$); δ0.85 (6H, t), 1.1 (9H, s), 1.7 (4H, q), 3.2 (2H, s), 3.6 (3H, s), 5.4 (2H, s),

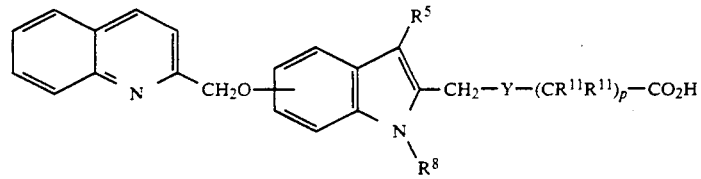

| Ex. No. | ATTACH POINT | R$^8$ | R$^5$ | Y—(CR$^{11}$R$^{11}$)$_p$ |
|---|---|---|---|---|
| 59 | 5 | —CH$_2$Ph-4-Cl | —C(Me)$_2$Pr | C(Me)$_2$ |
| 60 | 5 | —CH$_2$Ph-4-Cl | —C(Me)$_2$Et | C(Me)$_2$ |
| 61 | 5 | —CH$_2$Ph-3-F | —C(Me)$_3$ | C(Me)$_2$ |
| 62 | 5 | —CH$_2$Ph-4-Cl | —CH(Me)$_2$ | C(Me)$_2$ |
| 63 | 5 | —CH$_2$Ph-4-Cl | -c-Pr | C(Me)$_2$ |
| 64 | 5 | —CH$_2$Ph-4-Cl | -(1-Me)-c-Pr | C(Me)$_2$ |
| 65 | 5 | —CH$_2$Ph-4-Cl | -c-C$_5$H$_9$ | C(Me)$_2$ |
| 66 | 5 | —CH$_2$Ph-4-Cl | -c-C$_6$H$_{11}$ | C(Me)$_2$ |
| 67 | 5 | —CH$_2$Ph-4-Cl | —C(Me)$_2$Ph | C(Me)$_2$ |
| 68 | 5 | —CH$_2$Ph-4-Cl | —C(Me)$_2$Ph-4-Cl | C(Me)$_2$ |
| 69 | 5 | —CH$_2$Ph-4-Cl | -1-Ad | C(Me)$_2$ |
| 70 | 5 | —CH$_2$Ph-4-Cl | —CH$_2$-1-Ad | C(Me)$_2$ |
| 71 | 6 | -t-Bu | —Ch$_2$Ph-4-Cl | C(Me)$_2$ |
| 72 | 6 | —C(Me)$_2$Et | —Ch$_2$Ph-4-Cl | C(Me)$_2$ |

EXAMPLE 73

3-[N-(4-Chlorobenzyl)-3-(3,3-dimethyl-1-oxo-1-butyl)-5-(quinolin-2-ylmethoxy)indol-2-yl]-2,2-diethylpropanoic acid Step A: Methyl 4-chloro-2,2-diethyl-4-pentenoate To a cold solution (0° C.) of diisopropylamine 5.5 (2H, s) 6.9 (3H, m), 7.3 (4H, m), 7.6 (1H, dd), 7.7 (1H, d), 7.8 (1H, td), 7.9 (1H, d), 8.1 (1H, d), 8.3 ppm (1H, d).

Step D: Methyl 3-[N-(4-chlorobenzyl)-5-(quinolin-2-ylmethoxy)indol-2-yl]-2,2-diethylpropanoate The title compound was prepared according to the method of Example 47, Step A, but using methyl 3-[N-(4-chlorobenzyl -3-(t-butylthio)-5-(quinolin-2-ylmethoxy)indol-2-yl]-2,2-diethylpropanoate from Step C in place of methyl 3-[N-(4-chlorobenzyl)-3-(t-butylthio)-5-(quinolin-2-ylmethoxy)indol-2-yl]-2,2-dimethylpropanoate.

Step E: Methyl 3-[N-(4-chlorobenzyl)-3-(3,3-dimethyl-1-oxo-1-butyl)-5-(quinolin-2-ylmethoxy)indol-2-yl]-2,2-diethylpropanoate To a cold solution (0° C.) of methyl 3-[N-(4-chlorobenzyl)-5-(quinolin-2-ylmethoxy)indol-2-yl]-2,2-diethylpropanoate (from Step D) (177 mg, 0.33 mmol) in CH$_2$Cl$_2$ (3 mL) was added AlCl$_3$ (220 mg, 1.65 mmol) followed by t-butylacetyl chloride (82 μL, 0.66 mmol). The reaction was stirred at 0° C. for 20 minutes and then quenched with 30 mL of 0.5 N Na, K tartrate solution, and extracted with 3×30 mL of EtOAc. The organic layers were combined and dried over MgSO$_4$. Filtration and concentration gave an oily residue which was purified by flash chromatography (eluant: EtOAc-hexane 17:83) to give the title compound.

Step F: 3-[N-(4-Chlorobenzyl)-3-(3,3-dimethyl-1-oxo-1-butyl)-5-(quinolin-2-ylmethoxy)-indol-2-yl]-2,2-diethylpropanoic acid The compound from Step E was hydrolysed using THF (2.5 mL), MeOH (0.6 mL) and NaOH (1N, 1.5 mL). The solution was heated at 70° C. for 2 weeks. The reaction was neutralized by addition of Na$_4$OAc buffer (20 mL of 25% w/v) and extracted with EtOAc (3×30 mL). The organic layers were combined, dried over MgSO$_4$, filtered and concentrated. The resulting residue was purified by flash chromatography (eluant: EtOAc-hexane-HOAc (250:750:1)) to give the title compound.

Anal. C, H, N for sodium salt.1¼ H$_2$O; Calc. C, 67.70; H, 6.43; N, 4.15, Found C, 67.67; H, 6.31; N, 4.06.

EXAMPLE 74

Methyl 3-[N-(4-chlorobenzyl)-3,6-bis(acetyl)-5-(quinolin-2-ylmethoxy)indol-2-yl]-2,2-dimethylpropanoate The title compound was isolated in Step B of Example 48 from a chromatography on silica gel (EtOAc-Hexane 2:3).

$^1$H NMR (CD$_3$COCD$_3$): δ1.22 6H, s), 2.63 3H, s), 2.66 (3H, s), 3.58 (3H, s), 3.65 (2H, s), 5.61 (2H, s), 5.65 (2H, s), 6.95 (2H, d), 7.31 (2H, d), 7.62 (1H, br t), 7.71–7.85 (4H, m), 7.97 (1H, d), 8.08 (1H, d) 8.40 ppm (1H, d).

EXAMPLE 75

Methyl 3-[N-(4-chlorobenzyl)-3,6-bis(cyclopropanecarbonyl)-5-(quinolin-2-ylmethoxy)indol-2-yl]-2,2-dimethylpropanoate The title compound was isolated in Step B of Example 49 from a chromatography on silica gel (EtOAc-hexane 3:7) and was recrystallized from EtOAc-EtOH; m.p. 166°–167° C.

EXAMPLES 76–89

Using the techniques of Methods 1 through 12 as required, the following compounds are prepared:

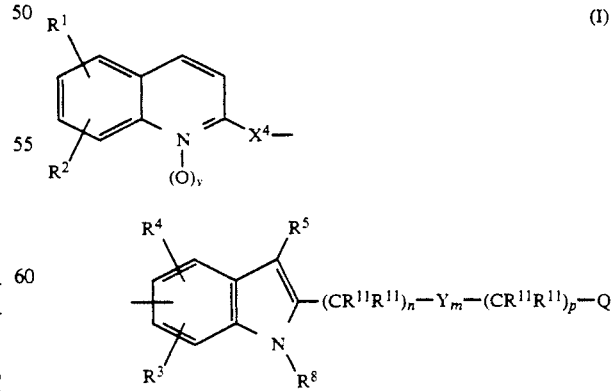

ID #1066 (Ie)

| Ex. No. | X$^4$ | Y—(CR$^{11}$R$^{11}$)$_p$ | Q |
|---|---|---|---|
| 76 | CH$_2$O | C(Me)$_2$ | —C(O)NHS(O)$_2$Me |
| 77 | CH$_2$O | C(Me)$_2$ | —NHS(O)$_2$Ph-4-Me |
| 78 | CH$_2$O | C(Me)$_2$ | —C(O)NH-t-Bu |
| 79 | CH$_2$O | OCH$_2$CH(Me) | —CO$_2$H |
| 80 | CH$_2$O | CH$_2$CH$_2$ | Tz |
| 81 | CH$_2$O | OCH(Me) | Tz |
| 82 | CH$_2$O | C(Me)$_2$ | —S(O)$_2$NH—Et |
| 83 | CH$_2$O | C(Me)$_2$ | —CO$_2$CH$_2$C(O)NMe$_2$ |
| 84 | CH$_2$O | C(Me)$_2$ | —C(O)NHCH$_2$CO$_2$H |
| 85 | CH$_2$O | C(Me)$_2$ | —CH$_2$OH |
| 86 | (E)—CH=CH | C(Me)$_2$ | —CO$_2$H |
| 87 | CH$_2$CH$_2$ | C(Me)$_2$ | —CO$_2$H |
| 88 | CH$_2$S | C(Me)$_2$ | —CO$_2$H |
| 89 | CH$_2$S(O)$_2$ | C(Me)$_2$ | —CO$_2$H |

What is claimed is:

1. A compound of the formula I:

(I)

wherein:

R$^1$, R$^2$, R$^3$, R$^4$ and R$^{10}$ are independently hydrogen, halogen, lower alkyl, lower alkenyl, lower alkynyl, —CF₃, —CN, —NO₂, —N₃, —C(OH)R¹¹R¹¹, —CO₂R¹², —SR¹⁴, —S(O)R¹⁴, —S(O)₂R¹⁴, —S(O)₂NR¹⁵R¹⁵, —OR¹⁵, —NR¹⁵R¹⁵, —C(O)R¹⁶ or —(CH₂)ᵣR²¹;

R⁵ is hydrogen, —CH₃, —CF₃, —C(O)H, X¹—R⁶ or X²—R⁷;

R⁶ and R⁹ are independently: alkyl, —(CH₂)ᵤPh(R¹⁰)₂ or —(CH₂)ᵤTh(R¹⁰)₂;

R⁷ is —CF₃ or R⁶;

R⁸ is hydrogen or X³—R⁹;

each R¹¹ is independently hydrogen or lower alkyl, or two R¹¹'s on same carbon atom are joined to form a cycloalkyl ring of 3 to 6 carbon atoms;

R¹² is hydrogen, lower alkyl or —CH₂R²¹;

R¹³ is lower alkyl or —(CH₂)ᵣR²¹;

R¹⁴ is —CF₃ or R¹³;

R¹⁵ is hydrogen, —C(O)R¹⁶, R¹³, or two R¹⁵'s on the same nitrogen may be joined to form pyrrolidine, piperidine, morpholine, thiamorpholine, piperazine or N-methylpiperazine 2,5 dioxo-1-pyrrolidinyl, (3-pyridinylcarbonyl)amino, 1,3-dihydro-1,3-dioxo-2H-isoindol-2-yl, 1,3-dihydro-2H-isoindol-2-yl, 2,4-imidazolinedion-1-yl, 2,6-piperidinedion-1-yl, 2-imidazolyl, 2-oxo-1,3-dioxolen-4-yl, piperindin-1-yl, morpholin-1-yl or piperazin-1-yl;

R¹⁶ is hydrogen, —CF₃, lower alkyl, lower alkenyl, lower alkynyl or —(CH₂)ᵣR²¹;

R¹⁷ is —(CH₂)ₛ—C(R¹⁸R¹⁸)—(CH₂)ₛ—R¹⁹ or —CH₂-C(O)NR¹⁵R¹⁵;

R¹⁸ is hydrogen or lower alkyl;

R¹⁹ is a) pyrrolidine, piperidine, morpholine, thiamorpholine, piperazine or N-methylpiperazine 2,5 dioxo-1-pyrrolidinyl,(3-pyridinylcarbonyl)amino, 1,3-dihydro-1,3-dioxo-2H-isoindol-2-yl,1,3-dihydro-2H-isoindol-2-yl,2,4-imidazolinedion-1-yl,2,6-piperidinedion-1-yl,2-imidazolyl,2-oxo-1,3-dioxolen-4-yl,piperindin-1-yl,morpholin-1-yl or piperazin-1-yl, or b) the radical W-R²⁰;

R²⁰ is alkyl or C(O)R²³;

R²¹ is phenyl substituted with 1 or 2 R²² groups;

R²² is hydrogen, halogen, lower alkyl, lower alkoxy, lower alkylthio, lower alkylsulfonyl, lower alkylcarbonyl, —CF₃, —CN, —NO₂ or —N₃;

R²³ is alkyl, cycloalkyl, monocyclic tetrahydrofuran, tetrahydrothiophene, pyrrolidine, piperidine or tetrahydropyran;

R²⁴ is the residual structure of a standard amino acid, or R¹⁸ and R²⁴ attached to the same N can cyclize to form a proline residue;

m is 0 to 1;
n is 0 to 3;
p is 1 to 3 when m is 1;
p is 0 to 3 when m is 0;
r is 0 to 2;
s is 0 to 3;
t is 0 to 2;
u is 0 to 3;
v is 0 or 1;
W is O, S or NR¹⁵;
X¹ is O, or NR¹⁵;
X² is C(O), CR¹¹R¹¹, S, S(O) or S(O)₂;
X³ is C(O), CR¹¹R¹¹, S(O)₂ or a bond;
X⁴ is CH=CH, CH₂—Y¹ or Y¹—CH₂;
Y is X¹ or X²;
Y¹ is O, S, S(O)₂ or CH₂;
Q is —CO₂R¹², —C(O)NHS(O)₂R¹⁴, —NHS(O)₂R¹⁴, —S(O)₂NHR¹⁵ —C(O)NR¹⁵R¹⁵, —CO₂R¹⁷, —C(O)NR¹⁸R²⁴, —CH₂OH, or 1H- or 2H-tetrazol-5-yl;

and the pharmaceutically acceptable salts thereof.

2. The compound of claim 1 wherein X⁴ is CH₂—Y¹, Y¹ is O and the remaining sustituents are as defined for Formula I; and the pharmaceutically acceptable salts thereof.

3. The compound of claim 1 wherein
R¹, R², R³ and R⁴ are hydrogen;
R⁵ is X²—R⁷ or —OR⁶;
R⁷ is R⁶;
R⁸ is R⁹;
R¹⁰ is hydrogen or halogen;
m is 0;
n is 1 to 3;
u is 0 in R⁶ and 1 in R⁹;
v is 0;
X² is CR¹¹R¹¹ or S;
X⁴ is CH₂—Y¹;
Y¹ is O;
Q is —CO₂R¹²; and the remaining substituents are as defined for Formula I;

and the pharmaceutically acceptable salts thereof.

4. The compound of claim 1 wherein
R¹, R², R³ and R⁴ are hydrogen;
R⁵ is X²—R⁷ or —OR⁶;
R⁷ is R⁶;
R⁸ is R⁹;
R¹⁰ is hydrogen or halogen;
m is 0;
n is 1 to 3;
u is 0 in R⁶ and 1 in R⁹;
v is 0;
X² is CR¹¹R¹¹ or S;
X⁴ is CH₂—Y¹;
Y¹ is O;
Q is 1-H- or 2H-tetrazol-5-yl; and the remaining substituents are as defined for Formula I;
and the pharmaceutically acceptable salts thereof.

5. A compound of claim 1 of the formula Ia:

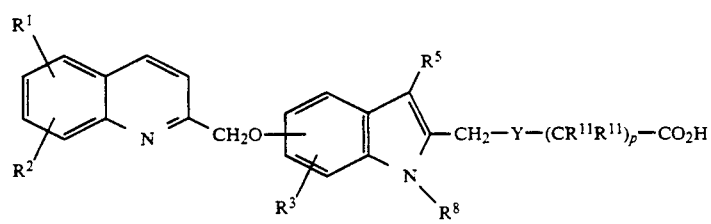

wherein the substituents are as defined in claim 1.

6. A compound of claim 1 of the formula Ic wherein the substituents are as follows:

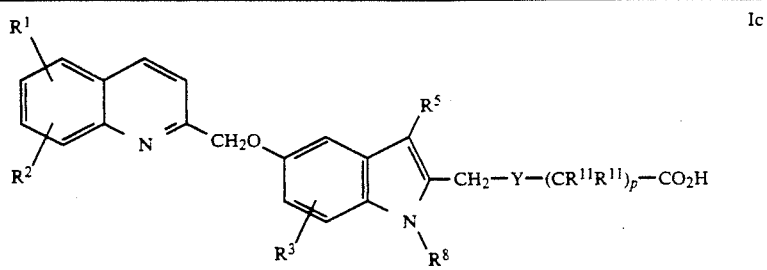

| $R^1$ | $R^2$ | $R^3$ | $R^5$ | $R^8$ | $Y-(CR^{11}R^{11})_p$ |
|---|---|---|---|---|---|
| 6-Cl | 7-Cl | H | Me | —CH$_2$Ph-4-Cl | C(Me)$_2$; |
| H | 7-Cl | H | Me | —Ch$_2$Ph-4-Cl | C(Me)$_2$; |
| H | H | 4-allyl | —S-t-Bu | —CH$_2$Ph-4-Cl | C(Me)$_2$; |
| H | H | 4-allyl | H | —CH$_2$Ph-4-Cl | C(Me)$_2$; |
| H | H | H | —O-i-Pr | —CH$_2$Ph-4-Cl | C(Me)$_2$; |
| H | H | H | —S-t-Bu | —CH$_2$Ph-4-Cl | CH$_2$OCH(Me); |
| H | H | H | —S-t-Bu | —CH$_2$Ph-4-Cl | CHMe; |
| H | H | H | —S-t-Bu | —CH$_2$Ph-4-S-t-Bu | C(Me)$_2$; |
| H | H | H | —S-t-Bu | —CH$_2$Ph-4-Cl | CH$_2$OCH$_2$; |
| H | H | H | —S-t-Bu | —CH$_2$Ph-4-Cl | CHEt; |
| H | H | H | —C(O)CH$_2$-t-Bu | —CH$_2$Ph-4-Cl | CHMe; |
| H | H | H | —C(O)CH$_2$-t-Bu | H | C(Me)$_2$; |
| H | H | H | —C(O)CH$_2$-t-Bu | —CH$_2$Ph-4-CF$_3$ | C(Me)$_2$; |
| H | H | H | —C(O)CH$_2$-t-Bu | —CH$_2$Ph | C(Me)$_2$; |
| H | H | H | —C(O)CH$_2$-t-Bu | —CH$_2$Ph-3-OMe | C(Me)$_2$; |
| H | H | H | —C(O)CH$_2$-t-Bu | —CH$_2$CHCH$_2$ | C(Me)$_2$; |
| H | H | H | —C(O)CH$_2$-t-Bu | —CH$_2$Ph-4-OMe | C(Me)$_2$; |
| H | H | H | —C(O)CH$_2$-t-Bu | Me | C(Me)$_2$; |
| H | H | H | —C(O)CH$_2$-t-Bu | —CH$_2$PH-4-F | C(Me)$_2$; |
| H | H | H | —C(O)CH$_2$-t-Bu | —CH$_2$Ph-4-Br | C(Me)$_2$; |
| H | H | H | —C(O)CH$_2$-t-Bu | —CH$_2$Ph-4-Cl | C(Et)$_2$; |
| H | H | H | —C(O)CH$_2$-t-Bu | —CH$_2$Ph-4-I | C(Me)$_2$ or |
| H | H | H | -t-Bu | —CH$_2$Ph-3-F | C(Me)$_2$. |

7. A compound of claim 1 of the formula Ib wherein the substituents are as follows:

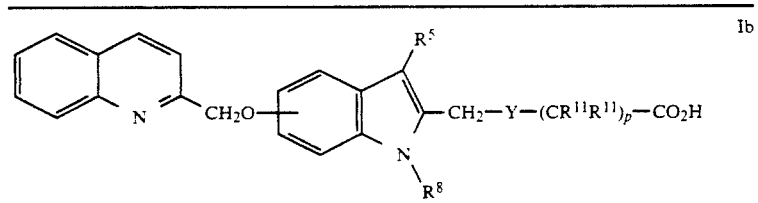

| ATTACH POINT | $R^8$ | $R^5$ | $Y-(CR^{11}R^{11})_p$ |
|---|---|---|---|
| 6 | —CH$_2$Ph-4-Cl | —S-t-Bu | C(Me)$_2$ |
| 4 | —CH$_2$Ph-4-Cl | —S-t-Bu | C(Me)$_2$ |
| 7 | —CH$_2$Ph-4-Cl | —S-t-Bu | C(Me)$_2$ |
| 4 | —CH$_2$Ph-4-Cl | H | C(Me)$_2$ |
| 6 | Me | —C(O)Ph-4-Cl | C(Me)$_2$ |
| 6 | Me | —CH$_2$Ph-4-Cl | C(Me)$_2$ |
| 6 | H | —CH$_2$Ph-4-Cl | C(Me)$_2$ |
| 6 | —S(O)$_2$Ph | —CH$_2$Ph-4-Cl | C(Me)$_2$ |
| 6 | —CH$_2$Ph | —CH$_2$Ph-4-Cl | C(Me)$_2$ |
| 6 | —CH$_2$CHCH$_2$ | —CH$_2$Ph-4-Cl | C(Me)$_2$ |
| 6 | —(CH$_2$)$_2$CH$_3$ | —CH$_2$Ph-4-Cl | C(Me)$_2$ |
| 6 | —CH$_2$CH$_3$ | —CH$_2$Ph-4-Cl | C(Me)$_2$ |
| 6 | -t-Bu | —CH$_2$Ph-4-Cl | C(Me)$_2$ or |
| 6 | —C(Me)$_2$Et | —CH$_2$Ph-4-Cl | C(Me)$_2$. |

8. A compound of claim 1 of the Formula Id:

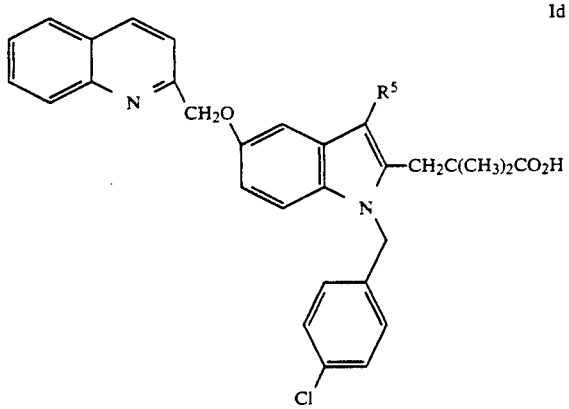

wherein the substituent R⁵ is as defined in claim 1.

9. A compound of claim 8 of the formula Id wherein the substituent R⁵ is: hydrogen, —Me, —S—t—Bu, —SPh, —S(O)₂Ph, —S(O)Ph, C(O)Ph, —CH₂Ph, —C(O)CH₂—t—Bu, —O—i—Pr, —C(O)—CF₃, —S(O)₂—t—Bu, —S(O)—t—Bu, —C(O)Ph—4—t—Bu, —C(O)Ph—4—Cl, t—Bu, —C(O)Me, —C(O)—c—Pr, —C(O)CH₂CH₂—c—C₅H₉, —C(O)CH₂CH(Me)₂, —C(O)Et, —C(O)CH(Me)₂, —C(O)C(Me)₃, —C(O)CH₂Ph, —C(Me)₂Pr, —C(Me)₂Et, —CH(Me)₂, —c—Pr, —(1—Me)—c—Pr, —c—C₅H₉, —c—C₆H₁₁, —C(Me)₂Ph, —C(Me)₂Ph—4—Cl, —1—Ad, —CH₂—1—Ad, or —CH₂CH₂—t—Bu.

10. A compound of claim 1 of the formula Ie wherein the substituents are as follows:

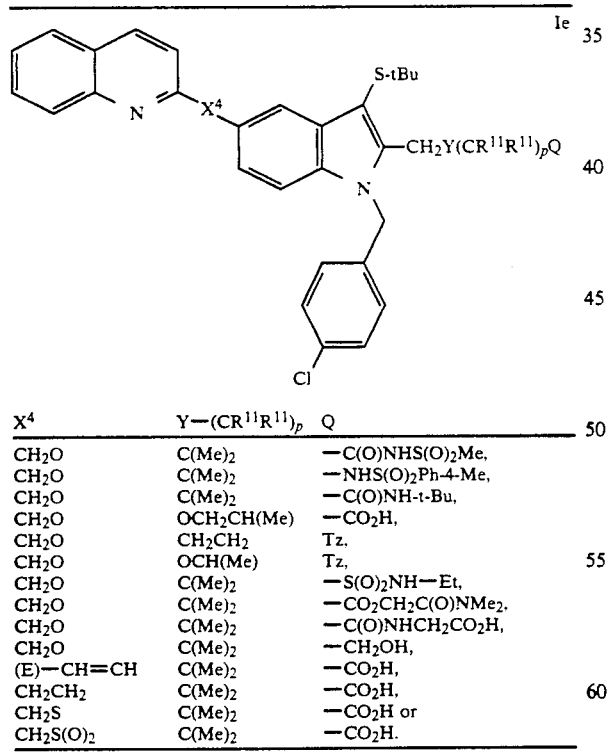

| X⁴ | Y—(CR¹¹R¹¹)ₚ | Q |
|---|---|---|
| CH₂O | C(Me)₂ | —C(O)NHS(O)₂Me, |
| CH₂O | C(Me)₂ | —NHS(O)₂Ph-4-Me, |
| CH₂O | C(Me)₂ | —C(O)NH-t-Bu, |
| CH₂O | OCH₂CH(Me) | —CO₂H, |
| CH₂O | CH₂CH₂ | Tz, |
| CH₂O | OCH(Me) | Tz, |
| CH₂O | C(Me)₂ | —S(O)₂NH—Et, |
| CH₂O | C(Me)₂ | —CO₂CH₂C(O)NMe₂. |
| CH₂O | C(Me)₂ | —C(O)NHCH₂CO₂H, |
| CH₂O | C(Me)₂ | —CH₂OH, |
| (E)—CH=CH | C(Me)₂ | —CO₂H, |
| CH₂CH₂ | C(Me)₂ | —CO₂H, |
| CH₂S | C(Me)₂ | —CO₂H or |
| CH₂S(O)₂ | C(Me)₂ | —CO₂H. |

11. The compound according to claim 1 which is:
3-[N-(p-chlorobenzyl)-3-(t-butylthio)-5-(quinolin-2-ylmethoxy)indol-2-yl]-2,2-dimethylpropanoic acid;
3-[N-(p-chlorobenzyl)-3-methyl-5-(quinolin-2-ylmethoxy)indol-2-yl]-2,2-dimethylpropanoic acid;
3-[N-(p-t-butylthiobenzyl)-3-(t-butylthio)-5-(quinolin-2-ylmethoxy)indol-2-yl]-2,2-dimethylpropanoic acid;
3-[N-(p-chlorobenzyl)-3-(phenylthio)-5-(quinolin-2-ylmethoxy)indol-2-yl]-2,2-dimethylpropanoic acid;
3-[N-(p-chlorobenzyl)-3-(phenylsulfonyl)-5-(quinolin-2-ylmethoxy)indol-2-yl]-2,2-dimethyl propanoic acid, N-oxide;
3-[N-(p-chlorobenzyl)-3-(phenylsulfonyl)-5-(quinolin-2-ylmethoxy)indol-2-yl]-2,2-dimethylpropanoic acid;
3-[N-(p-chlorobenzyl)-3-(phenylsulfinyl)-5-(quinolin-2-ylmethoxy)indol-2-yl]-2,2-dimethylpropanoic acid;
3-[N-(p-chlorobenzyl)-5-(quinolin-2-ylmethoxy)indol-2-yl]-2,2-dimethylpropanoic acid;
3-[N-(p-chlorobenzyl)-3-benzoyl-5-(quinolin-2-ylmethoxy)indol-2-yl]-2,2-dimethylpropanoic acid;
3-[N-(p-chlorobenzyl)-3-benzyl-5-(quinolin-2-ylmethoxy)indol-2-yl]-2,2-dimethylpropanoic acid;
3-[N-(p-chlorobenzyl)-3-(3,3-dimethyl-1-oxo-1-butyl)-5-(quinolin-2-ylmethoxy)indol-2-yl]-2,2-dimethylpropanoic acid;
2-[N-(p-chlorobenzyl)-3-(t-butylthio)-5-(quinolin-2-ylmethoxy)indol-2-yl]ethoxyethanoic acid;
3-[N-(p-chlorobenzyl)-3-(3,3-dimethyl-1-butyl)-5-(quinolin-2-ylmethoxy)indol-2-yl]-2,2-dimethylpropanoic acid;
3-[N-(p-chlorobenzyl)-3-(t-butylthio)-5-(quinolin-2-ylmethoxy)indol-2-yl]-2-methylpropanoic acid;
3-[N-(p-chlorobenzyl)-3-methyl-5-(6,7-dichloroquinolin-2-ylmethoxy)indol-2-yl]-2,2-dimethylpropanoic acid;
3-[N-(p-chlorobenzyl)-3-methyl-5-(7-chloroquinolin-2-ylmethoxy)indol-2-yl]-2,2-dimethylpropanoic acid;
3-[N-(p-chlorobenzyl)-4-allyl-5-(quinolin-2-ylmethoxy)-3-(t-butylthio)indol-2-yl]-2,2-dimethylpropanoic acid;
3-[N-(p-chlorobenzyl)-4-allyl-5-(quinolin-2-ylmethoxy)indol-2-yl]-2,2-dimethylpropanoic acid;
3-[N-(p-chlorobenzyl)-6-(quinolin-2-ylmethoxy)-3-(t-butylthio)indol-2-yl]-2,2-dimethylpropanoic acid;
3-[N-(p-chlorobenzyl)-4-(quinolin-2-ylmethoxy)-3-(t-butylthio)indol-2-yl]-2,2-dimethylpropanoic acid;
3-[N-(p-chlorobenzyl)-7-(quinolin-2-ylmethoxy)-3-(t-butylthio)indol-2-yl]-2,2-dimethylpropanoic acid;
2-[2-[N-(p-chlorobenzyl)-3-(t-butylthio)-5-(quinolin-2-ylmethoxy)indol-2-yl]ethoxy]propanoic acid;
3-[N-(p-chlorobenzyl)-4-(quinolin-2-ylmethoxy)indol-2-yl]-2,2-dimethylpropanoic acid;
3-[N-methyl-3-(p-chlorobenzoyl)-6-(quinolin-2-ylmethoxy)indol-2-yl]-2,2-dimethylpropanoic acid,
3-[N-methyl-3-(p-chlorobenzyl)-6-(quinolin-2-ylmethoxy)indol-2-yl]-2,2-dimethylpropanoic acid,
3-[N-(4-chlorobenzyl)-3-i-propoxy-5-(quinolin-2-ylmethoxy)indol-2-yl]-2,2-dimethylpropanoic acid,
3-[N-(4-chlorobenzyl)-3-(t-butylthio)-5-(quinolin-2-yl-methoxy)indol-2-yl]-2-ethylpropanoic acid,
3-[N-(4-chlorobenzyl)-3-trifluoroacetyl-5-(quinolin-2-ylmethoxy)-indol-2-yl]-2,2-dimethylpropanoic acid,
3-[N-(4-chlorobenzyl)-3-(3,3-dimethyl-1-oxo-1-butyl)-5-(quinolin-2-ylmethoxy)indol-2-yl]-2-methylpropanoic acid,
3-[3-(3,3-dimethyl-1-oxo-1-butyl-5-(quinolin-2-ylmethoxy)-indol-2-yl]-2,2-dimethylpropanoic acid, 3-[N-(4-triflouromethylbenzyl)-3-(3,3-dimethyl-1-oxo-1-butyl)-5-(quinolin-2-yl-methoxy)indol-2-yl]-2,2-dimethylpropanoic acid, 3-[N-benzyl-3-(3,3-dimethyl-1-oxo-1-butyl)-5-(quinolin-2-ylmethoxy)-indol-2-yl]-2,2-dimethylpropanoic acid, 3-[N-(3-methoxybenzyl)-3-(3,3-dimethyl-1-oxo-1-butyl)-5-(quinolin-2-ylmethoxy)indol-2-yl]-2,2-dumethyl-propanoic acid, 3-[N-allyl-3-(3,3-dimethyl-1-oxo-1-butyl)-5-(quinolin-2-ylmethoxy)-indol-2-yl]-2,2-dimethylpropanoic acid, 3-[N-(4-methoxybenzyl)-3-(,3-dimethyl-1-oxo-1-butyl)-5-(quinolin-2-ylmethoxy)indol-2-yl]-2,2-dimethylpropanoic acid, 3-[N-methyl-3-(3,3-dimethyl-1-oxo-1-butyl)-5-(quinolin-2-ylmethoxy)indol-2-yl]-2,2-dimethylpropanoic acid, 3-[3-(4-chlorobenzyl)-6-(quinolin-2-ylmethoxy)indol-2-yl]-2,2-dimethylpropanoic acid, 3-[N-(phenylsulfonyl)-3-(4-chlorobenzyl)-6-(quinolin-2-ylmethoxy)indol-2-yl]-2,2-dimethylpropanoic acid, 3-[N-benzyl-3-(4-chlorobenzyl)-6-(quinolin-2-ylmethoxy)indol-2-yl]-2,2-dimethylpropanoic acid, 3-[N-(4-chlorobenzyl)-3-(t-butylsulfonyl)-5-(quinolin-2-ylmethoxy)indol-2-yl]-2,2-dimethylpropanoic acid, 3-[N-(4-chlorobenzyl)-3-(t-butylsulfinyl)-5-(quinolin-2-ylmethoxy)indol-2-yl]-2,2-dimethylpropanoic acid, 3-[N-allyl-3-(4-chlorobenzyl)-6-(quinolin-2-ylmethoxy)indol-2-yl]-2,2-dimethylpropanoic acid, 3-[N-(n-propyl)-3-(4-chlorobenzyl)-6-(quinolin-2-ylmethoxy)indol-2-yl]-2,2-dimethylpropanoic acid, 3-[N-ethyl-3-(4-chlorobenzyl)-6-(quinolin-2-ylmethoxy)indol-2-yl]-2,2-dimethylpropanoic acid, 3-[N-(4-chlorobenzyl)-3-(4-t-butylbenzoyl)-5-quinolin-2-yl-methoxy)indol-2-yl]-2,2-dimethylpropanoic acid, 3-[N-(4-chlorobenzyl)-3-(4-chlorobenzoyl)-5-(quinolin-2-ylmethoxy)indol-2-yl]-2,2-dimethylpropanoic acid, 3-[N-(4-chlorobenzyl)-3-(1,1-dimethylethyl)-5-(quinolin-2-ylmethoxy)indol-2-yl]-2,2-dimethylpropanoic acid, 3-[N-(4-chlorobenzyl)-3-acetyl-5-(quinolin-2-ylmethoxy)indol-2-yl]-2,2-dimethylpropanoic acid, 3-[N-(4-chlorobenzyl)-3-cyclopropanecarbonyl-5-(quinolin-2-ylmethoxy)indol-2-yl]-2,2-dimethylpropanoic acid, 3-[N-(4-chlorobenzyl)-3-(3-cyclopentylpropanoyl)-5-(quinolin-2-ylmethoxy)indol-2-yl]-2,2-dimethylpropanoic acid, 3-[N-(4-chlorobenzyl)-3-(3-methylbutanoyl)-5-(quinolin-2-yl-methoxy)indol-2-yl]-2,2-dimethylpropanoic acid, 3-[N-(4-chlorobenzyl)-3-propanoyl-5-(quinolin-2-ylmethoxy)indol-2-yl]-2,2-dimethylpropanoic acid, 3-[N-(4-chlorobenzyl)-3-(2-methylpropanoyl)-5-(quinolin-2-ylmethoxy)indol-2-yl]-2,2-dimethylpropanoic acid, 3-[N-(4-chlorobenzyl)-3-trimethylacetyl-5-(quinolin-2-ylmethoxy)indol-2-yl]-2,2-dimethylpropanoic acid, 3-[N-(4-chlorobenzyl)-3-phenylacetyl-5-(quinolin-2-ylmethoxy)indol-2-yl]-2,2-dimethylpropanoic acid, 3-[N-(4-fluorobenzyl)-3-(3,3-dimethyl-1-oxo-1-butyl)-5-(quinolin-2-ylmethoxy)indol-2-yl]-2,2-dimethylpropanoic acid, 3-[N-(4-bromobenzyl)-3-(3.3-dimethyl-1-oxo-1-butyl)-5-(quinolin-2-yl-ethoxy)indol-2-yl]-2,2-dimethylpropanoic acid, 3-[N-(4-iodobenzyl)-3-(3,3-dimethyl-1-oxo-1-butyl)-5-(quinolin-2-ylmethoxy)indol-2-yl]-2,2-dimethylpropanoic acid, 3-[N-(4-chlorobenzyl)-3-(1,1-dimethylbutyl)-5-(quinolin-1-ylmethoxy)indol-2-yl]-2,2-dimethylpropanoic acid, 3-[N-(4-chlorobenzyl)-3-(1,1-dimethylpropyl)-5-(quinolin-2-ylmethoxy)indol-2-yl]-2,2-dimethylpropanoic acid, 3-[N-(3-fluorobenzyl)-3-(1,1-dimethylethyl)-5-(quinolin-2-ylmethoxy)indol-2-yl]-2,2-dimethylpropanoic acid, 3-[N-(4-chlorobenzyl)-3-(1-methylethyl)-5-(quinolin-2-ylmethoxy)indol-2-yl]-2,2-dimethylpropanoic acid, 3-[N-(4-chlorobenzyl)-3-cyclopropyl-5-(quinolin-2-ylmethoxy)indol-2-yl]-2,2-dimethylpropanoic acid, 3-[N-(4-chlorobenzyl)-3-(1-methyl-1-cyclopropyl)-5-(quinolin-2-ylmethoxy)indol-2-yl]-2,2-dimethylpropanoic acid, 3-[N-(4-chlorobenzyl)-3-cyclopentyl-5-(quinolin-2-ylmethoxy)indol-2-yl]-2,2-dimethylpropanoic acid, 3-[N-(4-chlorobenzyl)-3-cyclohexyl-5-(quinolin-2-ylmethoxy)indol-2-yl]-2,2-dimethylpropanoic acid, 3-[N-(4-chlorobenzyl)-3-(α,α-dimethylbenzyl)-5-(quinolin-2-ylmethoxy)indol-2-yl]-2,2-dimethylpropanoic acid, 3-[N-(4-chlorobenzyl)-3-(4-chloro-α,α-dimethylbenzyl)-5-(quinolin-2-ylmethoxy)indol-2-yl]-2,2-dimethylpropanoic acid, 3-[N-(4-chlorobenzyl)-3-(1-adamantyl)-5-(quinolin-2-ylmethoxy)indol-2-yl]-2,2-dimethylpropanoic acid, 3-[N-(4-chlorobenzyl)-3-((1-adamantyl)methyl)-5-(quinolin-2-ylmethoxy)indol-2-yl]-2,2-dimethylpropanoic acid, 3-[N-(1,1-dimethylethyl)-3-(4-chlorobenzyl)-6-quinolin-2-ylmethoxy)indol-2-yl]-2,2-dimethylpropanoic acid, 3-[N-(1,1-dimethylpropyl)-3-(4-chlorobenzyl)-6-(quinolin-2-y)methoxy)indol-2-yl]-2,2-dimethylpropanoic acid, 3-[N-(4-chlorobenzyl)-3-(3,3-dimethyl-1-oxo-1-butyl)-5-(quinolin-2-ylmethoxy)indol-2-yl]-2,2-diethylpropanoic acid, methyl 3-[N-(4-chlorobenzyl)-3,6-bis(acetyl)-5-(q}inolin-2-ylmethoxy)indol-2-yl]-2,2-dimethylpropanoate, or methyl 3-[N-(4-chlorobenzyl)-3,6-bis(cyclopropanecarbonyl)-5-(quinolin-2-ylmethoxy)indol-2-yl]-2,2-dimethyl propanoate.

12. A pharmaceutical composition comprising a therapeutically effective amount of a compound of claim 1 and a pharmaceutically acceptable carrier.

13. The pharmaceutical composition of claim 12 additionally comprising an effective amount of a second active ingredient selected from the group consisting of non-steroidal anti-inflammatory drugs; peripheral analgesic agents; cyclooxygenase inhibitors; leukotriene antagonists; leukotriene biosynthesis inhibitors; $H_2$-receptor antagonists; antihistaminic agents; prostaglandin antagonists; thromboxane antagonists; thromboxane synthetase inhibitors; and ACE antagonists.

14. A pharmaceutical composition according to claim 13, wherein the second active ingredient is a non-steroidal anti-inflammatory drug.

15. A pharmaceutical composition comprising a therapeutically effective amount of a compound of claim 1, an effective amount of a second active ingredient which is a non-steroidal anti inflammatory drug, and a pharmaceutically acceptable carrier, wherein the weight ratio of said compound of claim 1 to said second active ingredient ranges from about 1000:1 to 1:1000.

16. A method of preventing the synthesis, the action, or the release of SRS-A or leukotrienes in a mammal which comprises administering to said mammal an effective amount of a compound of claim 1.

17. The method of claim 16 wherein the mammal is man.

18. A method of treating asthma in a mammal comprising administering to a mammal in need of such treatment a therapeutically effective amount of a compound of claim 1.

19. A method of treating inflammatory diseases of the eye in a mammal which comprises administering to a mammal in need of such treatment a therapeutically effective amount of a compound of claim 1.

20. The method of claim 19 wherein the mammal is man.

21. A sodium salt of a compound of the Formula Id:

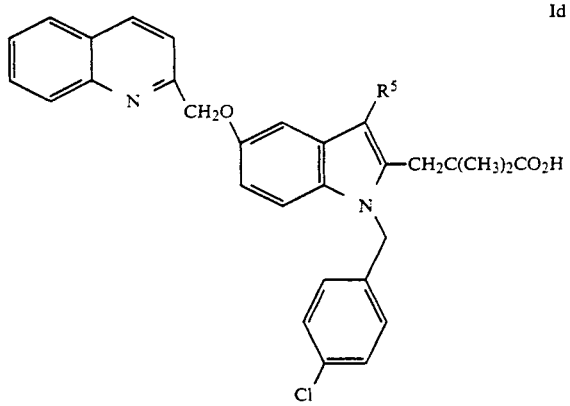

Id wherein $R^5$ is: hydrogen, —Me, —S—t—Bu, —SPh, —S(O)$_2$Ph, —S(O)Ph, C(O)Ph, —CH$_2$Ph, —C(O)CH$_2$—t—Bu, —O—i—Pr, —C(O)—CF$_3$, —S(O)$_2$—t—Bu, —S(O)—t—Bu, —C(O)Ph—4—t—Bu, —C(O)Ph—4—Cl, t—Bu, —C(O)Me, —C(O)—c—Pr, —C(O)CH$_2$CH$_2$—c—C$_5$H$_9$, —C(O)CH$_2$CH(Me)$_2$, —C(O)Et, —C(O)CH(Me)$_2$, —C(O)C(Me)$_3$, —C(O)CH$_2$Ph, —C(Me)$_2$Pr, —C(Me)$_2$Et, —CH(Me)$_2$, —c—Pr, —(1—Me)—c—Pr, —c—C$_5$H$_9$, —c—C$_6$H$_{11}$, —C(Me)$_2$Ph, —C(Me)$_2$Ph—4—Cl, —1—Ad, —CH$_2$—1—Ad, or —CH$_2$CH$_2$—t—Bu.

22. A sodium salt of a compound which is:
3-[N-(p-chlorobenzyl)-3-(t-butylthio)-5-(quinolin-2-ylmethoxy)indol-2-yl]-2,2-dimethylpropanoic acid;
3-[N-(p-chlorobenzyl)-3-methyl-5-(quinolin-2-ylmethoxy)indol-2-yl]-2,2-dimethylpropanoic acid;
3-[N-(p-t-butylthiobenzyl)-3-(t-butylthio)-5-(quinolin-2-ylmethoxy)indol-2-yl]-2,2-dimethylpropanoic acid;
3-[N-(p-chlorobenzyl)-3-(phenylthio)-5-(quinolin-2-ylmethoxy)indol-2-yl]-2,2-dimethylpropanoic acid;
3-[N-(p-chlorobenzyl)-3-(phenylsulfonyl)-5-(quinolin-2-ylmethoxy)indol-2-yl]-2,2-dimethyl propanoic acid, N-oxide;
3-[N-(p-chlorobenzyl)-3-(phenylsulfonyl)-5-(quinolin-2-ylmethoxy)indol-2-yl]-2,2-dimethylpropanoic acid;
3-[N-(p-chlorobenzyl)-3-(phenylsulfinyl)-5-(quinolin-2-ylmethoxy)indol-2-yl]-2,2-dimethylpropanoic acid;
3-[N-(p-chlorobenzyl)-5-(quinolin-2-ylmethoxy)indol-2-yl]-2,2-dimethylpropanoic acid;
3-[N-(p-chlorobenzyl)-3-benzoyl-5-(quinolin-2-ylmethoxy)indol-2-yl]-2,2-dimethylpropanoic acid;
3-[N-(p-chlorobenzyl)-3-benzyl-5-(quinolin-2-ylmethoxy)indol-2-yl]-2,2-dimethylpropanoic acid;
3-[N-(p-chlorobenzyl)-3-(3,3-dimethyl-1-oxo-1-butyl)-5-(quinolin-2-ylmethoxy)indol-2-yl]-2,2-dimethylpropanoic acid;
2-[N-(p-chlorobenzyl)-3-(t-butylthio)-5-(quinolin-2-ylmethoxy)indol-2-yl]ethoxyethanoic acid;
3-[N-(p-chlorobenzyl)-3-(3,3-dimethyl-1-butyl)-5-(quinolin-2-ylmethoxy)indol-2-yl]-2,2-dimethylpropanoic acid;
3-[N-(p-chlorobenzyl)-3-(t-butylthio)-5-(quinolin-2-ylmethoxy)indol-2-yl]-2-methylpropanoic acid;
3-[N-(p-chlorobenzyl)-3-methyl-5-(6,7-dichloroquinolin-2-ylmethoxy)indol-2-yl]-2,2-dimethylpropanoic acid;
3-[N-(p-chlorobenzyl)-3-methyl-5-(7-chloroquinolin-2-ylmethoxy)indol-2-yl]-2,2-dimethylpropanoic acid;
3-[N-(p-chlorobenzyl)-4-allyl-5-(quinolin-2-ylmethoxy)-3-(t-butylthio)indol-2-yl]-2,2-dimethylpropanoic acid;
3-[N-(p-chlorobenzyl)-4-allyl-5-(quinolin-2-ylmethoxy)indol-2-yl]-2,2-dimethylpropanoic acid;
3-[N-(p-chlorobenzyl)-6-(quinolin-2-ylmethoxy)-3-(t-butylthio)indol-2-yl]-2,2-dimethylpropanoic acid;
3-[N-(p-chlorobenzyl)-4-(quinolin-2-ylmethoxy)-3-(t-butylthio)indol-2-yl]-2,2-dimethylpropanoic acid;
3-[N-(p-chlorobenzyl)-7-(quinolin-2-ylmethoxy)-3-(t-butylthio)indol-2-yl]-2,2-dimethylpropanoic acid;
2-[2-[N-(p-chlorobenzyl)-3-(t-butylthio)-5-(quinolin-2-ylmethoxy)indol-2-yl]ethoxy]propanoic acid;
3-[N-(p-chlorobenzyl)-4-(quinolin-2-ylmethoxy)indol-2-yl]-2,2-dimethylpropanoic acid;
3-[N-methyl-3-(p-chlorobenzoyl)-6-(quinolin-2-ylmethoxy)indol-2-yl]-2,2-dimethylpropanoic acid,
3-[N-methyl-3-(p-chlorobenzyl)-6-(quinolin-2-ylmethoxy)indol-2-yl]-2,2-dimethylpropanoic acid,
3-[N-(4-chlorobenzyl)-3-i-propoxy-5-(quinolin-2-ylmethoxy)indol-2-yl]-2,2-dimethylpropanoic acid,
3-[N-(4-chlorobenzyl)-3-(t-butylthio)-5-(quinolin-2-yl-methoxy)indol-2-yl]-2-ethylpropanoic acid,
3-[N-(4-chlorobenzyl)-3-trifluoroacetyl-5-(quinolin-2-ylmethoxy)-indol-2-yl]-2,2-dimethylpropanoic acid,
3-[N-(4-chlorobenzyl)-3-(3,3-dimethyl-1-oxo-1-butyl)-5-(quinolin-2-ylmethoxy)indol-2-yl]-2-methylpropanoic acid,
3-[3-(3,3-dimethyl-1-oxo-1-butyl-5-(quinolin-2-ylmethoxy)-indol-2-yl]-2,2-dimethylpropanoic acid,
3-[N-(4-triflouromethylbenzyl)-3-(3,3-dimethyl-1-oxo-1-butyl)-5-(quinolin-2-yl-methoxy)indol-2-yl]-2,2-dimethylpropanoic acid,
3-[N-benzyl-3-(3,3-dimethyl-1-oxo-1-butyl)-5-(quinolin-2-ylmethoxy)-indol-2-yl]-2,2-dimethylpropanoic acid, 3-[N-(3-methoxybenzyl)-3-(3,3-dimethyl-1-oxo-1-butyl)-5-(quinolin-2-ylmethoxy)indol-2-yl]-2,2-dumethyl-propanoic acid,
3-[N-allyl-3-(3,3-dimethyl-1-oxo-1-butyl)-5-(quinolin-2-ylmethoxy)-indol-2-yl]-2,2-dimethylpropanoic acid,
3-[N-(4-methoxybenzyl)-3-(,3-dimethyl-1-oxo-1-butyl)-5-(quinolin-2-ylmethoxy)indol-2-yl]-2,2-dimethylpropanoic acid,
3-[N-methyl-3-(3,3-dimethyl-1-oxo-1-butyl)-5-(quinolin-2-ylmethoxy)indol-2-yl]-2,2-dimethylpropanoic acid,
3-[3-(4-chlorobenzyl)-6-(quinolin-2-ylmethoxy)indol-2-yl]-2,2-dimethylpropanoic acid,
3-[N-(phenylsulfonyl)-3-(4-chlorobenzyl)-6-(quinolin-2-ylmethoxy)indol-2-yl]-2,2-dimethylpropanoic acid,
3-[N-benzyl-3-(4-chlorobenzyl)-6-(quinolin-2-ylmethoxy)indol-2-yl]-2,2-dimethylpropanoic acid,
3-[N-(4-chlorobenzyl)-3-(t-butylsulfonyl)-5-(quinolin-2-ylmethoxy)indol-2-yl]-2,2-dimethylpropanoic acid,
3-[N-(4-chlorobenzyl)-3-(t-butylsulfinyl)-5-(quinolin-2-ylmethoxy)indol-2-yl]-2,2-dimethylpropanoic acid,
3-[N-allyl-3-(4-chlorobenzyl)-6-(quinolin-2-ylmethoxy)indol-2-yl]-2,2-dimethylpropanoic acid,
3-[N-(n-propyl)-3-(4-chlorobenzyl)-6-(quinolin-2-ylmethoxy)indol-2-yl]-2,2-dimethylpropanoic acid,
3-[N-ethyl-3-(4-chlorobenzyl)-6-(quinolin-2-ylmethoxy)indol-2-yl]-2,2-dimethylpropanoic acid,
3-[N-(4-chlorobenzyl)-3-(4-t-butylbenzoyl)-5-quinolin-2-yl-methoxy)indol-2-yl]-2,2-dimethyl-propanoic acid,
3-[N-(4-chlorobenzyl)-3-(4-chlorobenzoyl)-5-(quinolin-2-ylmethoxy)indol-2-yl]-2,2-dimethylpropanoic acid,
3-[N-(4-chlorobenzyl)-3-(1,1-dimethylethyl)-5-(quinolin-2-ylmethoxy)indol-2-yl]-2,2-dimethylpropanoic acid,
3-[N-(4-chlorobenzyl)-3-acetyl-5-(quinolin-2-ylmethoxy)indol-2-yl]-2,2-dimethylpropanoic acid,
3-[N-(4-chlorobenzyl)-3-cyclopropanecarbonyl-5-(quinolin-2-ylmethoxy)indol-2-yl]-2,2-dimethylpropanoic acid,
3-[N-(4-chlorobenzyl)-3-(3-cyclopentylpropanoyl)-5-(quinolin-2-ylmethoxy)indol-2-yl]-2,2-dimethylpropanoic acid,
3-[N-(4-chlorobenzyl)-3-(3-methylbutanoyl)-5-(quinolin-2-yl-methoxy)indol-2-yl]-2,2-dimethylpropanoic acid,
3-[N-(4-chlorobenzyl)-3-propanoyl-5-(quinolin-2-ylmethoxy)indol-2-yl]-2,2-dimethylpropanoic acid,
3-[N-(4-chlorobenzyl)-3-(2-methylpropanoyl)-5-(quinolin-2-ylmethoxy)indol-2-yl]-2,2-dimethylpropanoic acid,
3-[N-(4-chlorobenzyl)-3-trimethylacetyl-5-(quinolin-2-ylmethoxy)indol-2-yl]-2,2-dimethylpropanoic acid,
3-[N-(4-chlorobenzyl)-3-phenylacetyl-5-(quinolin-2-ylmethoxy)indol-2-yl]-2,2-dimethylpropanoic acid,
3-[N-(4-fluorobenzyl)-3-(3,3-dimethyl-1-oxo-1-butyl)-5-(quinolin-2-ylmethoxy)indol-2-yl]-2,2-dimethylpropanoic acid,
3-[N-(4-bromobenzyl)-3-(3.3-dimethyl-1-oxo-1-butyl)-5-(quinolin-2-yl-ethoxy)indol-2-yl]-2,2-dimethylpropanoic acid,
3-[N-(4-iodobenzyl)-3-(3,3-dimethyl-1-oxo-1-butyl)-5-(quinolin-2-ylmethoxy)indol-2-yl]-2,2-dimethylpropanoic acid,
3-[N-(4-chlorobenzyl)-3-(1,1-dimethylbutyl)-5-(quinolin-1-ylmethoxy)indol-2-yl]-2,2-dimethylpropanoic acid,
3-[N-(4-chlorobenzyl)-3-(1,1-dimethylpropyl)-5-(quinolin-2-ylmethoxy)indol-2-yl]-2,2-dimethylpropanoic acid,
3-[N-(3-fluorobenzyl)-3-(1,1-dimethylethyl)-5-(quinolin-2-ylmethoxy)indol-2-yl]-2,2-dimethylpropanoic acid,
3-[N-(4-chlorobenzyl)-3-(1-methylethyl)-5-(quinolin-2-ylmethoxy)indol-2-yl]-2,2-dimethylpropanoic acid,
3-[N-(4-chlorobenzyl)-3-cyclopropyl-5-(quinolin-2-ylmethoxy)indol-2-yl]-2,2-dimethylpropanoic acid,
3-[N-(4-chlorobenzyl)-3-(1-methyl-1-cyclopropyl)-5-(quinolin-2-ylmethoxy)indol-2-yl]-2,2-dimethylpropanoic acid,
3-[N-(4-chlorobenzyl)-3-cyclopentyl-5-(quinolin-2-ylmethoxy)indol-2-yl]-2,2-dimethylpropanoic acid,
3-[N-(4-chlorobenzyl)-3-cyclohexyl-5-(quinolin-2-ylmethoxy)indol-2-yl]-2,2-dimethylpropanoic acid,
3-[N-(4-chlorobenzyl)-3-(α,α-dimethylbenzyl)-5-(quinolin-2-ylmethoxy)indol-2-yl]-2,2-dimethylpropanoic acid,
3-[N-(4-chlorobenzyl)-3-(4-chloro-α,α-dimethylbenzyl)-5-(quinolin-2-ylmethoxy)indol-2-yl]-2,2-dimethylpropanoic acid,
3-[N-(4-chlorobenzyl)-3-(1-adamantyl)-5-(quinolin-2-ylmethoxy)indol-2-yl]-2,2-dimethylpropanoic acid,
3-[N-(4-chlorobenzyl)-3-((1-adamantyl)methyl)-5-(quinolin-2-ylmethoxy)indol-2-yl]-2,2-dimethylpropanoic acid,
3-[N-(1,1-dimethylethyl)-3-(4-chlorobenzyl)-6-quinolin-2-ylmethoxy)indol-2-yl]-2,2-dimethylpropanoic acid,
3-[N-(1,1-dimethylpropyl)-3-(4-chlorobenzyl)-6-(quinolin-2-y)methoxy)indol-2-yl]-2,2-dimethylpropanoic acid,
3-[N-(4-chlorobenzyl)-3-(3,3-dimethyl-1-oxo-1-butyl)-5-(quinolin-2-ylmethoxy)indol-2-yl]-2,2-diethylpropanoic acid.

* * * * *